(12) United States Patent
Blackburn et al.

(10) Patent No.: US 7,087,148 B1
(45) Date of Patent: Aug. 8, 2006

(54) BINDING ACCELERATION TECHNIQUES FOR THE DETECTION OF ANALYTES

(75) Inventors: Gary Blackburn, Glendora, CA (US); Jost G. Vielmetter, Pasadena, CA (US); Jon Faiz Kayyem, Pasadena, CA (US)

(73) Assignee: Clinical Micro Sensors, Inc., Pasedena, CA (US)

( * ) Notice: Subject to any disclaimer, the term of this patent is extended or adjusted under 35 U.S.C. 154(b) by 642 days.

(21) Appl. No.: 09/712,792

(22) Filed: Nov. 13, 2000

Related U.S. Application Data

(63) Continuation-in-part of application No. 09/440,371, filed on Nov. 12, 1999, now abandoned, and a continuation-in-part of application No. 09/338,726, filed on Jun. 23, 1999, now Pat. No. 6,264,825, and a continuation-in-part of application No. 09/134,058, filed on Aug. 14, 1998, now Pat. No. 6,290,839.

(60) Provisional application No. 60/171,981, filed on Dec. 23, 1999, provisional application No. 60/090,389, filed on Jun. 23, 1998.

(51) Int. Cl.
*G01N 27/327* (2006.01)
*G01N 21/447* (2006.01)
*G01N 27/453* (2006.01)

(52) U.S. Cl. .................. 205/452; 204/403.06; 205/603; 205/461; 205/612

(58) Field of Classification Search ........... 204/403.01, 204/403.03, 403.04, 403.05, 403.06, 403.07, 204/409, 411, 412, 603, 452, 461, 612
See application file for complete search history.

(56) References Cited

U.S. PATENT DOCUMENTS

| | | | |
|---|---|---|---|
| 4,415,732 A | 11/1983 | Caruthers et al. | |
| 4,683,195 A | 7/1987 | Mullis et al. | |
| 4,704,193 A | 11/1987 | Bowers et al. | |
| 4,707,352 A | 11/1987 | Stavrianopoulos | |
| 4,707,440 A | 11/1987 | Stavrianopoulos | |
| 4,711,955 A | 12/1987 | Ward et al. | |
| 4,713,347 A | 12/1987 | Mitchell et al. | |
| 4,735,907 A | 4/1988 | Schaeffer et al. | |
| 4,755,458 A | 7/1988 | Rabbani et al. | |
| 4,787,963 A | 11/1988 | MacConnell | |
| 4,819,658 A | 4/1989 | Kolodner | |

(Continued)

FOREIGN PATENT DOCUMENTS

CA    2090904    9/1993

(Continued)

OTHER PUBLICATIONS

Boon et al., "Mutation Detection by Electrocatalysis at DNA-Modified Electrodes," Nature Biotechnology, 18: 1096-1100 (Oct. 2000).

Fotin, A. et al., "Parallel Thermodynamic Analysis of Duplexes on Oligodeoxyribonucleotide Microchips," Nucleic Acids Research, 216(6):1515-1521 (1998).

Hess et al., "Base Pairing Properties of Novel Transition Metal PNA Conjugates," Journal of Inorganic Biochemistry, 74:161 (1999).

(Continued)

*Primary Examiner*—Alex Noguerola
(74) *Attorney, Agent, or Firm*—Dorsey & Whitney LLP; Robin M. Silva

(57) ABSTRACT

The invention relates to compositions and methods useful in the acceleration of binding of target analytes to capture ligands on surfaces. Detection proceeds through the use of an electron transfer moiety (ETM) that is associated with the target analyte, either directly or indirectly, to allow electronic detection of the ETM.

32 Claims, 26 Drawing Sheets

U.S. PATENT DOCUMENTS

| | | | |
|---|---|---|---|
| 4,908,319 A | 3/1990 | Smyczek et al. | |
| 4,840,890 A | 6/1989 | Hill et al. | |
| 4,840,893 A | 6/1989 | Hill et al. | |
| 4,849,513 A | 7/1989 | Smith et al. | |
| 4,868,103 A | 9/1989 | Stavrianopoulos et al. | |
| 4,877,830 A | 10/1989 | Döbeli et al. | |
| 4,894,325 A | 1/1990 | Englehardt et al. | |
| 4,920,047 A | 4/1990 | Giaever et al. | |
| 4,943,523 A | 7/1990 | Stavrianopoulos | |
| 4,945,045 A | 7/1990 | Forrest et al. | |
| 4,952,685 A | 8/1990 | Stavrianopoulos | |
| 4,964,972 A | 10/1990 | Sagiv et al. | |
| 4,994,373 A | 2/1991 | Stavrianopoulos | |
| 5,002,885 A | 3/1991 | Stavrianopoulos | |
| 5,013,831 A | 5/1991 | Stavrianopoulos | |
| 5,015,569 A | 5/1991 | Pontius | |
| 5,032,216 A | 7/1991 | Felten | |
| 5,064,618 A | 11/1991 | Baker et al. | |
| 5,066,372 A | 11/1991 | Weetall | |
| 5,071,531 A | 12/1991 | Soane | |
| 5,082,830 A | 1/1992 | Brakel et al. | |
| 5,089,112 A | 2/1992 | Skotheim et al. | |
| 5,098,781 A | 3/1992 | Minnick et al. | |
| 5,100,775 A | 3/1992 | Smyczek et al. | |
| 5,106,751 A | 4/1992 | Newman | |
| 5,110,745 A | 5/1992 | Kricka et al. | |
| 5,126,022 A | 6/1992 | Soane et al. | |
| 5,126,034 A | 6/1992 | Carter et al. | |
| 5,130,238 A | 7/1992 | Malek et al. | |
| 5,135,627 A | 8/1992 | Soane | |
| 5,147,607 A | 9/1992 | Mochida | |
| 5,156,810 A | 10/1992 | Ribi | |
| 5,175,269 A | 12/1992 | Stavrianopoulos | |
| 5,180,968 A | 1/1993 | Bruckenstein et al. | |
| 5,192,507 A | 3/1993 | Taylor et al. | |
| 5,194,133 A * | 3/1993 | Clark et al. ............ 204/608 | |
| 5,200,051 A | 4/1993 | Cozzette et al. | |
| 5,200,471 A | 4/1993 | Coleman et al. | |
| 5,238,808 A | 8/1993 | Bard et al. | |
| 5,241,060 A | 8/1993 | Engelhardt et al. | |
| 5,242,828 A | 9/1993 | Bergstrom et al. | |
| 5,262,035 A | 11/1993 | Gregg et al. | |
| 5,278,043 A | 1/1994 | Bannwarth et al. | |
| 5,296,375 A | 3/1994 | Kricka et al. | |
| 5,304,487 A | 4/1994 | Wilding et al. | |
| 5,308,754 A | 5/1994 | Kankare et al. | |
| 5,312,527 A | 5/1994 | Mikkelsen et al. | |
| 5,320,725 A | 6/1994 | Gregg et al. | |
| 5,324,457 A | 6/1994 | Zhang et al. | |
| 5,328,824 A | 7/1994 | Ward et al. | |
| 5,356,786 A | 10/1994 | Heller et al. | |
| 5,391,272 A | 2/1995 | O'Daly et al. | |
| 5,403,451 A | 4/1995 | Riviello et al. | |
| 5,436,161 A | 7/1995 | Bergstrom et al. | |
| 5,443,701 A | 8/1995 | Willner et al. | |
| 5,449,767 A | 9/1995 | Ward et al. | |
| 5,455,166 A | 10/1995 | Walker | |
| 5,472,881 A | 12/1995 | Beebe et al. | |
| 5,476,928 A | 12/1995 | Ward et al. | |
| 5,486,335 A | 1/1996 | Wilding et al. | |
| 5,491,097 A | 2/1996 | Ribi et al. | |
| 5,494,810 A | 2/1996 | Barany et al. | |
| 5,498,392 A | 3/1996 | Wilding et al. | |
| 5,505,321 A | 4/1996 | Caron et al. | |
| 5,512,131 A | 4/1996 | Kumar et al. | |
| 5,532,128 A | 7/1996 | Eggers et al. | |
| 5,552,270 A | 9/1996 | Khrapko et al. | |
| 5,565,322 A | 10/1996 | Heller | |
| 5,565,552 A | 10/1996 | Magda et al. | |
| 5,571,568 A | 11/1996 | Ribi et al. | |
| 5,573,906 A | 11/1996 | Bannwarth et al. | |
| 5,582,984 A | 12/1996 | Bieniarz et al. | |
| 5,585,069 A | 12/1996 | Zanzucchi et al. | |
| 5,585,646 A | 12/1996 | Kossovsky et al. | |
| 5,587,128 A | 12/1996 | Wilding et al. | |
| 5,591,578 A | 1/1997 | Meade et al. | |
| 5,593,838 A | 1/1997 | Zanzucchi et al. | |
| 5,595,908 A | 1/1997 | Fawcett et al. | |
| 5,601,982 A | 2/1997 | Sargent et al. | |
| 5,603,351 A | 2/1997 | Cherukuri et al. | |
| 5,605,662 A | 2/1997 | Heller et al. | |
| 5,620,850 A | 4/1997 | Bamdad et al. | |
| 5,622,821 A | 4/1997 | Selvin et al. | |
| 5,631,337 A | 5/1997 | Sassi et al. | |
| 5,632,876 A | 5/1997 | Zanzucchi et al. | |
| 5,632,957 A | 5/1997 | Heller et al. | |
| 5,635,358 A | 6/1997 | Wilding et al. | |
| 5,637,469 A | 6/1997 | Wilding et al. | |
| 5,643,738 A | 7/1997 | Zanzucchi et al. | |
| 5,653,939 A | 8/1997 | Hollis et al. | |
| 5,657,208 A | 8/1997 | Noe et al. | |
| 5,670,322 A | 9/1997 | Eggers et al. | |
| 5,681,484 A | 10/1997 | Zanzucchi et al. | |
| 5,694,932 A | 12/1997 | Michel | |
| 5,700,667 A | 12/1997 | Marble et al. | |
| 5,705,346 A | 1/1998 | Okamoto et al. | |
| 5,705,348 A | 1/1998 | Meade et al. | |
| 5,726,026 A | 3/1998 | Wilding et al. | |
| 5,727,548 A | 3/1998 | Hill et al. | |
| 5,728,352 A | 3/1998 | Ackley | |
| 5,728,532 A * | 3/1998 | Ackley .................... 435/6 | |
| 5,741,700 A | 4/1998 | Ershov et al. | |
| 5,750,015 A | 5/1998 | Soane et al. | |
| 5,755,942 A | 5/1998 | Zanzucchi et al. | |
| 5,756,050 A | 5/1998 | Ershov et al. | |
| 5,759,866 A | 6/1998 | Machida et al. | |
| 5,763,191 A | 6/1998 | Knoll et al. | |
| 5,770,029 A | 6/1998 | Nelson et al. | |
| 5,770,369 A | 6/1998 | Meade et al. | |
| 5,770,721 A | 6/1998 | Ershov et al. | |
| 5,776,672 A | 7/1998 | Hashimoto et al. | |
| 5,780,234 A | 7/1998 | Meade et al. | |
| 5,785,789 A | 7/1998 | Gagnon et al. | |
| 5,795,453 A | 8/1998 | Gilmartin | |
| 5,824,473 A | 10/1998 | Meade et al. | |
| 5,834,224 A | 11/1998 | Ruger et al. | |
| 5,837,859 A | 11/1998 | Teoule et al. | |
| 5,843,767 A | 12/1998 | Beattie | |
| 5,849,486 A | 12/1998 | Heller et al. | |
| 5,851,772 A | 12/1998 | Mirzabekov et al. | |
| 5,874,316 A | 2/1999 | Cornell et al. | |
| 5,922,183 A | 7/1999 | Rauh | |
| 5,942,388 A | 8/1999 | Willner et al. | |
| 5,942,397 A | 8/1999 | Tarlov et al. | |
| 5,945,286 A | 8/1999 | Krihak et al. | |
| 5,952,172 A | 9/1999 | Meade et al. | |
| 5,968,745 A | 10/1999 | Thorp et al. | |
| 5,972,199 A | 10/1999 | Heller et al. | |
| 5,976,802 A | 11/1999 | Ansorge et al. | |
| 6,013,170 A | 1/2000 | Meade | |
| 6,013,459 A | 1/2000 | Meade | |
| 6,020,047 A | 2/2000 | Everhart | |
| 6,051,380 A * | 4/2000 | Sosnowski et al. ............ 435/6 | |
| 6,060,023 A | 5/2000 | Maracas | |
| 6,060,327 A | 5/2000 | Keen | |
| 6,066,448 A | 5/2000 | Wohlstadter et al. | |
| 6,071,699 A | 6/2000 | Meade et al. | |
| 6,087,100 A | 7/2000 | Meade et al. | |
| 6,090,545 A | 7/2000 | Wohlstadter et al. | |
| 6,090,631 A | 7/2000 | Catterall et al. | |
| 6,090,933 A | 7/2000 | Kayyem et al. | |
| 6,096,273 A | 8/2000 | Kayyem et al. | |
| 6,096,497 A | 8/2000 | Bauer | |
| 6,096,500 A | 8/2000 | Oprandy et al. | |

| | | | |
|---|---|---|---|
| 6,096,825 A | 8/2000 | Garnier et al. | |
| 6,100,045 A | 8/2000 | Van Es | |
| 6,100,099 A | 8/2000 | Gordon et al. | |
| 6,107,080 A | 8/2000 | Lennox | |
| 6,153,737 A | 11/2000 | Manoharan et al. | |
| 6,177,250 B1 | 1/2001 | Meade et al. | |
| 6,180,352 B1 | 1/2001 | Meade et al. | |
| 6,197,515 B1 | 3/2001 | Bamdad et al. | |
| 6,200,761 B1 | 3/2001 | Meade et al. | |
| 6,203,758 B1 | 3/2001 | Marks et al. | |
| 6,207,369 B1 | 3/2001 | Wohlstadter et al. | |
| 6,211,356 B1 | 4/2001 | Wiessler et al. | |
| 6,238,870 B1 | 5/2001 | Meade et al. | |
| 6,258,545 B1 | 7/2001 | Meade et al. | |
| 6,265,155 B1 | 7/2001 | Meade et al. | |
| 6,268,149 B1 | 7/2001 | Meade et al. | |
| 6,268,150 B1 | 7/2001 | Meade et al. | |
| 6,277,576 B1 | 8/2001 | Meade et al. | |
| 6,291,188 B1 | 9/2001 | Meade et al. | |
| 6,300,141 B1 | 10/2001 | Segal et al. | |
| 6,306,584 B1 | 10/2001 | Bamdad | |
| 6,322,979 B1 * | 11/2001 | Bamdad et al. | 435/6 |
| 6,416,642 B1 * | 7/2002 | Alajoki et al. | 204/451 |
| 2001/0034033 A1 | 10/2001 | Meade et al. | |
| 2001/0046679 A1 | 11/2001 | Meade et al. | |

FOREIGN PATENT DOCUMENTS

| | | |
|---|---|---|
| EP | 0 063 879 | 11/1982 |
| EP | 0 234 938 | 2/1987 |
| EP | 0 213 825 A2 | 3/1987 |
| EP | 0 229 442 | 7/1987 |
| EP | 0 229 943 | 7/1987 |
| EP | 0 234 938 A1 | 9/1987 |
| EP | 0 439 036 A1 | 7/1991 |
| EP | 0 478 319 A1 | 4/1992 |
| EP | 0 515 615 A1 | 12/1992 |
| EP | 0 599 337 | 1/1994 |
| EP | 0 664 452 A2 | 7/1995 |
| EP | 0 637 998 B2 | 7/1996 |
| EP | 0515615 | 9/1996 |
| EP | 0 637 996 B2 | 7/1997 |
| EP | 0 668 502 B1 | 5/2002 |
| JP | 238166 | 10/1988 |
| JP | 6-41183 | 2/1994 |
| WO | 86/05815 | 3/1985 |
| WO | 90/05732 | 5/1990 |
| WO | WO 90/05303 A1 | 5/1990 |
| WO | 92/10757 | 6/1992 |
| WO | 93/10267 | 5/1993 |
| WO | 93/22678 | 11/1993 |
| WO | 93/23425 | 11/1993 |
| WO | WO 93/22053 A1 | 11/1993 |
| WO | WO 93/22678 A2 | 11/1993 |
| WO | WO 93/22678 A3 | 11/1993 |
| WO | WO 93/23425 A1 | 11/1993 |
| WO | 94/22889 | 10/1994 |
| WO | 95/11755 | 5/1995 |
| WO | 95/15971 | 6/1995 |
| WO | WO 95/34816 A1 | 12/1995 |
| WO | WO 95/35102 A1 | 12/1995 |
| WO | WO 96/10178 A1 | 4/1996 |
| WO | WO 96/15576 A1 | 5/1996 |
| WO | 96/40712 | 12/1996 |
| WO | WO 96/39252 A1 | 12/1996 |
| WO | WO 96/40712 A1 | 12/1996 |
| WO | 97/01646 | 1/1997 |
| WO | WO 97/12030 A1 | 4/1997 |
| WO | 98/57159 | 6/1997 |
| WO | 97/27329 | 7/1997 |
| WO | WO 97/31256 A2 | 8/1997 |
| WO | WO 97/31256 A3 | 8/1997 |
| WO | WO 97/32156 A3 | 8/1997 |
| WO | WO 97/36681 A1 | 10/1997 |
| WO | 97/44651 | 11/1997 |
| WO | WO 97/41425 A1 | 11/1997 |
| WO | WO 97/44651 A1 | 11/1997 |
| WO | WO 97/46568 A1 | 12/1997 |
| WO | WO 98/01758 A1 | 1/1998 |
| WO | 98/04740 | 2/1998 |
| WO | WO 98/05424 A1 | 2/1998 |
| WO | WO 98/12539 A1 | 3/1998 |
| WO | 98/20162 | 5/1998 |
| WO | 98/27229 | 6/1998 |
| WO | 98/28444 | 7/1998 |
| WO | WO 98/31839 A2 | 7/1998 |
| WO | WO 98/31839 A3 | 7/1998 |
| WO | 98/35232 | 8/1998 |
| WO | WO 98/51823 A1 | 11/1998 |
| WO | WO 98/57158 A1 | 12/1998 |
| WO | 99/14596 | 3/1999 |
| WO | WO 99/29711 A1 | 6/1999 |
| WO | WO 99/37819 A2 | 7/1999 |
| WO | WO 98/57319 A1 | 11/1999 |
| WO | WO 99/57317 A1 | 11/1999 |
| WO | 99/67425 | 12/1999 |

OTHER PUBLICATIONS

Mitchell et al., "Programmed Assembly of DNA Functionalized Quantum Dots," *J. Am. Chem. Soc.*, 121:8122-8123 (1999).

Timofeev, E. et al., "Methidium Intercalator Inserted into Synthetic Oligonucleotides," Tetrahedron Letters, 37(47):8467-8470 (1996).

Gao et al., "Sel assembled conducting polymer monolayers of poly(3-octlthiophene) on gold electrodes," Synthetic Metals, 75:5-10 (1995).

Albers, W. M., et al., "Design of Novel Molecular Wires for Realizing Long-Distance Electron Transfer," *Bioeletrochemistry*, 42:25-33 (1997).

Allerman, K.S., et al., "Eletrochemical Recitification at a Monolayer-Modified Electrode," *J. Phys. Chem*, 100:(42) 17050-17058 (1996).

Aizawa, M., et al., "Intergrated Molecular Systems for Biosensors," *Sensors and Actuators B*, B24 (Nos. 1/3) part 1:1-5 (Mar. 1995).

Arkin, M., et al., "Evidence for Photoelectron Transfer Through DNA Intercalation," *J. Inorganic Biochem.* Abstracts, 6th International Conference on Bioinorganic Chemistry, 51(1) & (2):526 (1993).

Barisci, et al., "Conducting Polymer Sensors," *TRIP*, 4(9):307-311 (1996).

Baum, R. M., "Views on Biological, Long-Range Electron Transfer Stir Debate," *C&EN*, pp. 20-23 (1993).

Bechtold, R., et al., "Ruthenium-Modified Horse Heart Cytochrome c: Effect of pH and Ligation on the Rate of Intramolecular Electron Transfer between Ruthenium(II) and Heme(III)," *J. Phys. Chem.*, 90(16):3800-3804 (1986).

Bidan, "Electroconducting conjugated polymers: new sensitive matrices to build up chemical or electrochemical sensors. A Review.," *Sensors and Actuators*, B6:45-56 (1992).

Biotechnology and Genetics: Genetic Screening Integrated Circuit, *The Economist* (Feb. 25-Mar. 3, 1995).

Boguslavsky, L. et al., "Applications of redox polymers in biosensors," *Solid State Ionics*, 60:189-197 (1993).

Bowler, B. E., et al., "Long-Range Electron Transfer in Donor (Spacer) Acceptor Molecules and Proteins," *Progress in Inorganic Chemistry: Bioinorganic Chemistry*, 38:259-322 (1990).

Brun, A. M., et al., "Photochemistry of Intercalated Quaternary Diazaaromatic Salts," *J. Am. Chem. Soc.*, 113:8153-8159 (1991).

Bumm, et al., "Are Single Molecular Wires Conducting!," *Science* 271:1705-1707 (1996).

Cantor, C.R. et al., "Report on the Sequencing by Hybridization Workshop," *Genomics*, 13:1378-1383 (1992).

Carr, J.D., et al., "Novel Electrochemical Sensors for neutral Molecules," *Chem. Commun.*, 1649-1550 (1997).

Carter, et al., "Voltammetric Studies of the Interaction of Metal chelates with DNA. 2. Tris- Chelated Complexes of Cobalt (III) and Iron (II) with 10-Phenanthorile and 2,3'-Bipyridine," *J. Am. Chem. Soc.*, 11 "8901-8911 (1989).

Chang, I-Jy et al., "High-Driving-Force Electron Transfer in Metalloproteins: Intramolecular Oxidation of Ferrocytochrome c by Ru(2,2'-bpy)$_2$ (im)(His-33)$^{3+}$," *J. Am. Chem. Soc.*, 113:7056-7057 (1991).

Chidsey, C.E.D., et al., "Free Energy and Temperature Dependence of Electron Transfer at the Metal Electrolyte Interface," *Science*, 251:919-923 (1991).

Chidsey, et al., "Coadsorption of Ferrocene-Terminated and Unsubstituted Alkanethiols on Gold Electroactive Self-Assembled Monolayers," *J. Am. Chem. Soc.*, 112:4301-4306 (1990).

Davis, L. M., et al., "Electron Donor Properties of the Antitumour Drug Amsacrine as Studied by Fluorescence Quenching of DNA-Bound Ethidium," *Chem.-Biol. Interactions*, 62:45-58 (1987).

Davis, L. M., et al., "Elements of biosensor construction," *Enzyme Microb. Technol.* 17:1030-1035 (1995).

Degani et al., "Direct Electrical Communication between Chemically Modified Enzymes and Metal Electrodes. 2. Methods for Bonding Electron-Transfer Relays to Glucose Oxidase and D-Amino-Acid Oxidase," *J. Am. Chem. Soc.* 110:2615-2620 (1988).

Degani, Y., et al., "Electrical Communication between Redox Centers of Glucose Oxidase and Electrodes via Electrostatically and Covalently Bound Redox Polymers,"*J. Am. Chem. Soc.*, 111:2357-2358 (1989).

Degani, Y., et al., "Direct Electrical Communication between Chemically Modified Enzymes and Metal Electrodes. 1. Electron Transfer from Glucose Oxidase to Metal Electrodes via Electron Relays, Bound Covalently to the Enzyme," *J. Phys. Chem.*, 91(6):1285-1288 (1987).

Deinhammer, R.S., et al., "Electronchemical Oxidation of Amine-containing compounds: A Route to the Surface Modification of glassy carbon electrodes," *Langmuir*, 10:1306-1313 (1994).

Dreyer, G. B., et al., "Sequence-specific cleavage of single-stranded DNA: Oligodeoxynucleotide-EDTA-Fe(II)," *Proc. Natl. Acad. Sci. USA*, 82:968-972 (1985).

Durham, B., et al., "Photoinduced Electron-Transfer Kinetics of Singly Labeled Ruthenium Bis(bipyridin) Dicarboxybipyridine Cytochrome c Derivatives," *Biochemistry*, 28:8659-8665 (1989).

Durham, B., et al., "Electron-Transfer Kinetics of Singly Labeled Ruthenium(II) Polypyridine Cytochrome c Derivatives," *American Chemical Society*, pp. 181-193 (1990).

Elias, H., et al., "Electron-Transfer Kinetics of Zn-Substituted Cytochrome c and Its Ru(NH$_3$)$_5$(Histidine-33) Derivative," *J. Am. Chem. Soc.*, 110:429-434 (1988).

Farver, O., et al., "Long-range intramolecular electron transfer in azurins," *Proc. Natl. Acad. Sci. USA*, 86:6968-6972 (1989).

Fox, L. S., et al., "Gaussian Free-Energy Dependence of Electron-Transfer Rates in Iridium Complexes," *Science*, 247:1069-1071 (1990).

Fox, M. A., et al., "Light-Harvesting Polymer Systems," *C&EN*, pp. 38-48 (Mar. 15, 1993).

Francois, J.-C., et al., "Periodic Cleavage of Poly(dA) by Oligothymidylates Covalently Linked to the 1,10-Phenanthroline-Copper Complex," *Biochemistry*, 27:2272-2276 (1988).

Friedman, A. E., et al., "Molecular 'Light Switch' for DNA: Ru(bpy)$_2$(dppz)$^{2+}$," *J. Am. Chem. Soc.*, 112:4960-4962 (1990).

Fromherz, P., et al., "Photoinduced Electron Transfer in DNA Matrix from Intercalated Ethidium to Condensed Methylviologen," *J. Am. Chem. Soc.*, 108:5361-5362 (1986).

Gregg, B. A., et al., "Redox Polymer Films Containing Enzymes. 1. A Redox-Conducting Epoxy Cement: Synthesis, Characterization, and Electrocatalytic Oxidation of Hydroquinone," *J. Phys. Chem.*, 95:5970-5975 (1991).

Hashimoto, et al., "Sequence-Specific Gene Detection with a Gold Electrode Modified with DNA Probes and an Electrochemically Active Dye," *Anal. Chem.* 66:3830-3833 (1994).

Hegner, et al., "Immobilizing DNA on gold via thiol modification for atomic force microscopy imaging in buffer solutions," *FEBS* 336(3):452-456 (1993).

Heller, A., et al., "Amperometric biosensors based on three-dimensional hydrogel-forming epoxy networks," *Sensors and Actuators*, 13-14:180-183 (1993).

Heller, A., "Electrical Wiring of Redox Enzymes," *Acc. Chem. Res.*, 23:128-134 (1990).

Heller et al., "Fluorescent Energy Transfer Oligonucleotide Probes," *Fed. Proc.* 46(6):1968 (1987) Abstracts No. 248.

Ho "DNA-Mediated Electron Transfer and Application to 'Biochip'Development," *Abstract Office of Naval Research* (Report Date: Jul. 25, 1991) 1-4, RR04106.

Hobbs et al., "Polynucleotides Containing 2'-Amino-2'deoxyribose and 2'-Azido-2'-deoxyriose," *Biochemistry*, 12(25):5138-5145 (1973).

Hsung, et al., "Synthesis and Characterization of Unsymmetric Ferrocene-Terminated Phenylethynyl Oligomers," *Organometallics*, 14:4808-4815 (1995).

Hsung, et al., "Thiophenol Protecting Groups for the Palladium-Catalyzed Heck Reaction: Efficient Syntheses of Conjugated Arylthiols," *Tetrahedron Letters.* 36(26):4525-4528 (1995).

Jenkins et al., A Sequence-Specific Molecular Light Switch: Tebhering of an Oligonucleotide to a Dipyridophenazine Complex of Ruthenium (II), *J. Am. Chem. Soc.*, 114:8736-8738 (1992).

Johnston, D.H., et al., "Trans-Dioxorhenium (V)-Mediated Electrocatalytic Oxidation of DNA at Indium Tin-Oxide Electrodes: Voltammetric Detection of DNA Cleavage in Solution," *Inorg. Chem.* 33:6388-6390 (1994).

Katritzky, et al., "Pyridylethylation—A New Protection Method for Active Hydrogen Compounds," *Tetrahedron Letters*, 25(12):1223-1226 (1984).

Kelley, S.O. and J.K. Barton, "Electrochmeistry of Methylene Blue Bound to a DNA-Modified Electrode," *Bioconjugate Chem.*, 8:31-37 (1997).

Kojima et al., "A DNA Probe of Ruthenium Bipyridine Complex Using Photocatalytic Activity," *Chemistry Letter*, pp. 1889-1982 (1989).

Korri-Youssoufi, H., et al., "Toward Bioelectronics: Specific DNA Recognition Based on an Oligonucleotide-Functionalized Polypyrrole," *J. Am. Chem.* 119:(31) 7388-7389 (1997).

Lee, et al., "Direct Measurement of the Forces Between Complementary Strands of DNA," *Science*, 266:771-773 (1994).

Lenhard, J.R., et al., "Part VII Covalent Bonding of a Reversible- Electrode Reactanbt to Pt Electrodes Using an organosilane Reagent" *J. Electronal. Chem.*, 78:195-201 (1977).

Lincoln, P., et al., "Short-Circuiting the Molecular Wire: Cooperative Binding of Δ-[Rh(phen)$_2$dppz]$^{2+}$ and Δ-[Rh(phi)$_2$dppz]$^{3+}$ to DNA," *J. Am. Chem. Soc* . . . 119:1454-1455 (1997).

Lipkin "Identifying DNA by the Speed of Electrons," *Science News*, 147(8):117 (1995).

Maskos, et al., "Oligonucleotide hybridisations on glass supports: a novel linker for oligonucleotide synthesis and hybridisation properties of oligonucleotides synthesised *in situ*," *Nucleic Acids Research*, 30(7):1679-1684 (1992).

Mazzocchi, Ph.H. and G. Fritz, "Photolysis of N-(2-Methyl-2-Propenyl)phthalimide in Methanol. Evidence Supporting Radical-Radical Coupling of a Photochemically Generated Radical Ion Pair," *Journal of the American Chemical Society*, 108(18):5361-5362 (1986).

McGee, et al., "2'-Amino-2'-deoxyuridine via an Intramolecular Cyclization of a Trichloroacetimidate," *J. Org. Chem.*, 61:781-785 (1996).

Meade, T. J., "Driving-Force Effects on the Rate of Long-Range Electron Transfer in Ruthenium-Modified Cytochrome c," *J. Am. Chem. Soc.*, 111:4353-4356 (1989).

Meade, T. J., et al., "Electron Transfer through DNA: Site-Specific Modification of Duplex DNA with Ruthenium Donors and Acceptors," *Angew Chem. Int. Ed. Engl.*, 34:352 (1995).

Mestel, "'Electron Highway' Points to Identity of DNA," *New Scientist*, p. 21 (1995).

Millan, et al., "Voltammetric DNA Biosensor for Cystic Fibrosis Based on a Modified Carbon Paste Electrode," *Anal. Chem.*, 66:2943-2948 (1994).

Millan, K.M., et al., "Covalent Immobilization of DNA onto Glassy Carbon Electrodes," *Electroanalysis*, 4:929-932 (1992).

Millan, K.M. and Mikkelsen, S.R., "Sequence-Selective Biosensor for DNA Based on Electroactive Hybridization Indicators," *Anal. Chem.*,65:2317-2323 (1993).

Miller, C., "Absorbed ω-Hydroxy Thiol Monolayers on Gold Electrodes: Evidence for Electron Tunneling to Redox Species in Solution," *J. Phys. Chem.*, 95:877-886 (1991).

Murphy, C. J., et al., "Long-Range Photoinduced Electron Transfer Through a DNA Helix," *Science*, 262:1025-1029 (1993).

Mucic, R.C., et al., "Synthesis and Characterization of DNA with Ferrocenyl Groups Attached to Their 5'-Termini:Electrochemical Characterization of a Redox-Active nucleotide Monolayer," *Chem. Commun.*, 555-557 (1996).

Napier, M.E., et al., "Probing Bionolecule Tecognition with Electron Transfers Electrochemical Sensors for DNA Hybridization," *Bioconjugate Chem* 8:905-913 (1997).

Paterson, "Electric Genes: Current Flow in DNA Could Lead to Faster Genetic Testing," *Scientific American*, 33-34 (May 1995).

Purugganan, M. D., et al., Accelerated Electron Transfer Between Metal Complexes Mediated by DNA, *Science*, 241:1645-1649 (1988).

Reimers, J.R., et al., "Towards Efficient Molecular Wires and Switches: The Brooker Ions," *BioSystems* 35:107-111 (1995).

Rhodes, D. And A. Klug, "Helical Periodicity of DNA Determined by Enzyme Digestion," *Nature*, 286:573-578 (1980).

Risser, S. M., et al., "Electron Transfer in DNA: Predictions of Exponential Growth and Decay of Coupling with Donor-Acceptor Distance," *J. Am. Chem. Soc.*, 115(6):2508-2510 (1993).

Sato, Y., et al., "Unidirectional Electron Transfer at Self-Assembled Monolayers of 11-Ferrocenyl-1-undecanethiol on Gold," *Bull. Chem. Soc. Jpn.*, 66(4):1032-1037 (1993).

Satyanarayana, S., et al., "Neither Δ- nor Δ-Tris(phenanthroline)ruthenium(II) Binds to DNA by Classical Intercalation," *Biochemistry*, 31(39):9319-9324 (1992).

Schlereth, D.D., et al., "Self-Assembled Monolayers with Biospecific Affinity for NAD (H)-Dependent Dehydrogenases: Characterization by Surface Plasmon Resonance Combined with Electrochemistry 'in situ'," *Journal of Electroanalytical Chemistry* 444:231-240 (1998).

Schreiber, et al., "Bis(purine) Complexes of trans-a$_2$Pt$^{II}$: Preparation and X-ray Structures of Bis(9-methyladenine) and Mixed 9-Methyladenine, 9-Methylguanine Complexes and Chemistry Relevant to Metal-Modified Nucelobase Triples and Quartets," *J. Am. Chem. Soc.* 118:4124-4132 (1996).

Schuhmann, W., et al., "Electron Transfer between Glucose Oxidase and Electrodes via Redox Mediators Bound with Flexible Chains to the Enzyme Surface," *J. Am. Chem. Soc.*, 113:1394-1397 (1991).

Schumm, et al., "Iterative Divergent/Convergent Approach to Linear Conjugated Oligomers by Successive Doubling of the Molecular Length: A Rapid Route to a 128 Å-Long Potential Molecular Wire," *Angew. Chem. Int. Ed. Engl.*, 33(11):1360-1363 (1994).

Sigel, G.B., et al., "A Self-Assembled Monolayer for the Binding and Study of Histidine-Tagged Proteins by Surface Plasmon Resonance," *Analytical Chemistry* 68:(3) 490-497 (1996).

Southern, E.M., et al., "Arrays of Complementary Oligonucleotides for Analysing the Hybridisation Hehavior of nucleic Acids," *Nucleic Acids Research* 22:(8) 1368-1373 (1994).

Strobel, S. A., et al., "Site-Specific Cleavage of a Yeast Chromosome by Oligonucleotide-Directed Triple-Helix Formation," *Science*, 249:73-75 (1990).

Su, et al., "Interfacial Nucleic Acid Hybridization Studied by Random Primer $^{32}$P Labelling and Liquid-Phase Acoustic Network Analysis," *Analytical Chemistry*, 66(6):769-777 (1994).

Takeda, H., et al., "Preparation of 1-Alkynyl 2-(Trimethylsilyl)ethyl Sulfides as Thiolare Anion Precursors for Self-Asdsembled Monolayers," *Tetrahedron Letters* 39:3701-3704 (1998).

Telser, J., et al., "DNA Duplexes Covalently Labeled at Two Sites: Synthesis and Characterization by Steady-State and Time-Resolved Optical Spectroscopies," *J. Am. Chem. Soc.*, 111:7226-7232 (1989).

Telser, J., et al., "DNA Oligomers and Duplexes Containing a Covalently Attached Derivative of Tris(2,2'- bipyridine)ruthenium(II): Synthesis and Characterization by Thermodynamic and Optical Spectroscopic Measurements," *J. Am. Chem. Soc.*, 111:7221-7226 (1989).

Thara, T., et al., "Gene Sensor using Ferrocenyl Oligonucleotide," *Chem. Commun.*, 1609-1610 (1997).

Tour, "Conjugated Macromolecules of Precise Length and Constitution. Organic Synthesis for the Construction of Nanoarchitectures," *Chem. Rev.*, 96:537-553 (1996).

Tour, et al., "Self-Assembled Monolayers and Multilayers of Conjugated Thiols, α-ω-Dithiols, and Thioacetyl-Containing Adsorbates. Understanding Attachments between Potential Molecular Wires and Gold Surfaces," *J. Am. Chem. Soc.*, 117:9529-9534 (1995).

Tullius, T.D. and B.A. Dombroski, "Iron(II) EDTA Used to Measure the Helical Twist Along Any DNA Molecule," *Science*, 230:679-681 (1985).

Turro, N., et al. "Photoelectron Transfer Between Molecules Adsorbed in Restricted Spaces," *Photochem. Convers. Storage Sol. Energy, Proc. Int. Conf., 8th*, pp. 121-139 (1990).

Turro, N. J., et al., "Molecular Recognition and Chemistry in Restricted Reaction Spaces. Photophysics and Photoinduced Electron Transfer on the Surfaces of Micelles, Dendrimers, and DNA," *Acc. Chem. Res.*, 24:332-340 (1991).

Uosake, K., et al., "A Self-Assembled Monolayer of Ferrocenylalkane Thiols on Gold as an Electron Mediator for the Reduction of Fe(III)-EDTA in Solution," *Electrochemica Acta.*, 36(11/12):1799-1801 (1991).

Van Ness, J., et al., "A Versatile Solid Support System for Oligodeoxynucleotide Probe-Based Hybridization Assays," *Nucleic Acids Research*, 19(12):3345-3349 (1991).

Weber, et al., "Voltammetry of Redox-Active Groups Irreversibly Adsorbed onto Electrodes. Treatment Using the Marcus Relation between Rate and Overpotential," *Anal. Chem.*, 66:3164-3172 (1994).

Williams, et al., "Studies of oligonucleotide interactions by hybridisation to arrays: the influence of dangling ends on duplex yield," *Nucleic Acids Research*, 22(8):1365-1367 (1994).

Winkler, J. R., et al., "Electron Transfer in Ruthenium-Modified Proteins," *Chem. Rev.*, 92:369-379 (1992).

Xu, et al., "Immobilization of DNA on an Aluminum(III) alkaneobisphosphonate Thin Film with Electrogenerated Chemiluminescent Detection," *J. Am. Chem. Soc.*, 116:8386-8387 (1994).

Xu, et al., "Immobilization and Hybridization of DNA on an Aluminum(III) Alkanebisphosphonate Thin Film with Electrogenerated Chemiluminescent Detection," *J. Am. Chem. Soc.*, 117:2627-2631 (1995).

Derwent Publications, Ltd. XP002124777. "DNA Detection for Gene Analysis in Biological and Medical Application." abstract, Nov. 4, 1997.

Pontius, et al., "Rapid Renaturation of Complementary DNA Strands Mediated by Cationic Detergents: A Role for High-Probability Binding Domains in Enhancing the Kinetics of Molecular Assembly Processes," *Proc. Natl. Acad. Sci. USA*, 88:8237-8241 (1991).

Pontius, et al., "Renaturation of Complementary DNA Strands Mediated gby Purified Mammalian Heterogeneous Nuclear Ribonucleoprotein A1 Protein: Implications for a Mechanism for Rapid Molecular Assembly," *Proc. Natl. Acad. Sci. USA*, 87:8403-8407 (1990).

Gineitis, et al., "Dissociation and Isolation of Chromatin Proteins in Salt Solutions by an Aqueous Two-Phase System," *Analytical Biochemistry*, 139:400-403 (1984).

Kohne, et al., "Room Temperature Method for Increasing the Rate of DNS Reassociation by Many Thousandfold: The Phenol Emulsion Reassociation Technique," *Biochemistry*, 16(24):5329-5341 (1977).

Caruana, et al., "Enzyme-Amplified Amerometric Detection of Hybridization and of a Single Base Pair Mutation in an 18-Base Oligonucleotide on a 7-μm-Diameter Microelectrode," *J. Am. Chem. Soc.*, 121:769-774 (1999).

Albertsson, P. "Rartition Studies on Nucleic Acids I. Influence of Electrolytes, Polymer Concentration and Nucleic Acid Conformation on the Partition in the Dextran-Polyethylene Glycol System," *Biochim. Biophys. Acta.*, 103:1-12 (1965).

Müller, et al., "DNA Fractionation by Two-Phase Partition with Aid of a Base-Specific Macroligand," *Analytical Biochemistry*, 118:269-277 (1981).

Müller, W. "Partitioning of Nucleic Acids," *Partitioning In Aqueous Two-Phase Systems*, 227-266 (1985).

Gingeras, et al., "Hybridization Properites of Immobilized Nucleic Acids," *Nucleic Acids Research*, 15(13):5373-5390 (1987).

Wetmur, J. "Acceleration of DNA Renaturation Rates," *Biopolymers*, 14:2517-2524 (1975).

Amasino, R. "Acceleration of Nucleic Acid Hybridization Rate by Polyethylene Glycol," *Analytical Biochemistry*, 152:304-307 (1986).

Herne, et al., "Characterization of DNA Probes Immobilized on Gold Surfaces," *J. Am. Chem. Soc.*, 119:8916-8920 (1997).

Steel, et al., "Electrochemical Quantitation of DNA Immobilized on Gold," *Anal. Chem.*, 70:4670-4677 (1998).

Finklea, H. "Electrochemistry of Organized Monolayers of Thiols and Related Molecules of Electrodes," *Electroanalytical Chemistry: A Series of Advances*, vol. 20. Dekker, NY. 1966.

Beattie, et al., "Flowthrough Genosensors: Designs and Applications," Publishing information not known.

Doktycz, et al., "Genosensors and Model Hybridization Studies," *Automation Technologies for Genome Characterization*, ed. Tony J. Beugelskijk, chapter 10, 205-225 (1997).

Chrisey, et al., "Covalent attachment of synthetic DNA to self-assembled monolayer films," *Nucleic Acids Research*, 24(15):3031-3039 (1996).

Clery, "DNA Goes Electric," *Science*, 267:1270 (1995).

*Commerce Business Daily* Issue of Sep. 26, 1996 PSA#1688.

DATABASE WPI, Derwent Publications Ltd., London, GB; AN1988-320199 & JP, A, 63 238 166 (Mitsubishi Denki KK), Oct. 4, 1988.

Gardner, et al., "Application of conducting polymer technology in microsystems," *Sensors and Actuators*, A51:57-66 (1995).

Gregg, B. A., et al., "Cross-linked redox gels containing glucose oxidase for amperometric biosensor applications," *Anal. Chem.*, 62:258-263 (1990).

Laviron, E., "A.C. Polarography and Faradaic Impedance of Strongly Adsorbed Electroactive Species. Part I: Theoretical and Experimental Study of Quasi-Reversible Reaction in the Case of a Langmuir Isotherm," *J. Electroanal. Chem.*, 97:135-149 (1979).

Laviron, E., "A.C. Polarography and Faradaic Impedance of Strongly Adsorbed Electoactive Species. Part III: Theoretical Complex Plane Analysis for a Surface Redox Reaction," *J. Electroanal. Chem.*, 105:35-42 (1979).

Orellana, G., et al., "Photoinduced Electron Transfer Quenching of Excited Ru(II) Polypyridyls Bound to DNA: The Role of the Nucleic Acid Double Helix," *Photochemistry and Photobiology*, 54(4):499-509 (1991).

Palecek, "From Polarography of DNA to Microanalysis with Nucleic Acid-Modified Electrodes," *Electroanalysis*. 8(1):7-14 (1996).

Yang, et al., "Growth and Characterization of Metal(II) Alkaneobisphosphonate Multilayer Thin Films on Gold Surfaces," *J. Am. Chem. Soc.*, 115:11855-11862 (1993).

Zhou, et al., "Fluorescent Chemosensors Based on Energy Migration in Conjugated Polymers: The Molecular Wire Approach to Increased Sensitivity," *J. Am. Chem. Soc.*, 117:12593-12602 (1995).

Maldonado-Rodriguez, et al., "Mutation Detection by Stacking Hybridization on Genosensor Arrays," *Molecular Biotechnology*, 11:13-25 (1999).

Eggers, et al., "Genosensors: Microfabricated Devices for Automated DNA Sequence Analysis," Advances in DNA Sequencing Technology, 1891:113-126 (1993).

Blonder et al., "Three-dimensional Redox-Active layered Composites of Au-Au, Ag-Ag and Au-Ag Colloids," *Chem. Commun.* 1393-1394 (1998).

Drobyshev, A. et al., "Sequence Analysis by Hybridization with Oligonucleotide Microchip: Identification of Δ-thalassemia Mutations," *Gene*, 188:45-52 (1997).

Dubiley, S. et al., "Fractionation, phosphorylation and Ligation on Oligonucleotide Microchips to Enhance Sequencing by Hybridization," *Nucleic Acids Research*, 25(12):2259-2265 (1997).

Elghanian et al., "Selective Colorimetric Detection of Polynucleotides Based on the Distance-Dependent Optical Properties of Gold Nanoparticles," *Science*, 277:1078-1081 (1997).

Guschin, D. et al., "Manual Manufacturing of Oligonucleotide, DNA, and Protein Microchips," *Analytical Biochemistry*, 250:203-211 (1997).

Guschin, D. et al., "Oligonucleotide Microchips as Genosensors for Determinative and Environmental Studies in Microbiology," 63(6):2397-2402 (1997).

Kamat et al., *J. Phys. chem.*, 93(4):1405-1409 (1989). Abstract.

Livshits, M. et al., "Theoretical Analysis of the Kinetics of DNA Hybridization with Gel-Immobilized Oligonucleotides," *Biophysical Journal*, 71:2795-2801 (1996).

Mirkin et al., "A DNA-based Method for Ratioally Assembling Nonoparticles into Macroscopic Materials," *Nature*, 382:607-609 (1996).

Mirzabekov, A. et al., "Dna Sequencing by Hybridization—a Megasequencing Method and a Diagnostic Tool," *Tibtech*, 12:27-32 (1994).

Mucic et al., "DNA-Directed Synthesis of Binary Nanoparticle Network Materials," *J. Am. Chem. Soc.*, 120:12674-12675 (1998).

Parinov, S., "DNA Sequencing by Hybridization to Microchip octa- and Decanucleotides Extened by Stacked Pentanucleotides," *Nucleic Acids Research*, 24(15):2998-3004 (1996).

Proudnikov, D. "Immobilization of DNA in Polyacrylamide Gel for the manufacture of DNA and DNA-Oligonucleotide Microchips," *Analytical Biochemistry*, 259:34-41 (1998).

Proudnikov, D. et al., "Chemical Methods of DNA and RNA Fluorescent Labeling," *Nucleic Acids Research*, 24(22):4535-4542 (1996).

Sloop et al., "Metalloorganic labels for DNA sequencing and mapping," *New. J. Chem.*, 18: 317-326 (1994). (added Apr. 23, 2001).

Storhoff et al., "One-Pot Colorimetric Differentiation of Polynucleotides with Single Base Imperfections Using Gold Nanoparticles Probes," *J. Am. Chem. Soc.*, 120:1959-1964 (1998).

Timofeev, E. et al., "Regioselective Immobilization of Short Oligonucleotides to Acrylic Copolymer Gel," *Nucleic Acids Research*, 24(16): 3142-3148 (1996).

Velev et al., "In Situ Assembly of Colloidal Particles into Miniaturized Biosensors," The ACS Journal of Surfaces and Colloids, *Langmuir*, 15(11):3693-3698 (1999).

Watson et al., "Hybrid Nanoparticles with Block Copolymer Shell Structures," *J. Am. Chem. Soc.*, 121:462-463 (1999).

Yershov, G. et al., "DNA Analysis and Diagnostics on Oligonucleotide Microchips," *Proc. Natl. Acad. Sci. USA*, 93:4913-4918 (1996).

Anne, A., et al., "Synthesis of first ferrocene labeled dideoxynucleotide and its use for 3'-redox end labeling of 5'-modified single stranded oligonucleotides," *Bioconjug. Chem.*, 12:396-405 (2001).

Bain, C., et al., "Formation of monolayers by the coadsorption of thiols on gold: variation in the length of the alkyl chain," *J. Am. Chem. Soc.*, 111:7164-7175 (1989).

Bamdad, C., "A DNA self-assembled monolayer for the specific attachment of unmodified double or single stranded DNA," *Biophys. J.*, 75:1997-2003 (1988).

Beattie, K., et al., "Genosensor Technology," *Clin. Chem.*, 39(4):719-722 (1993).

Che, G., et al., "Voltammetry of defect sites at a self-assembled monolayer on a gold surface," *J. Electroanalytical Chem.*, 453:9-17 (1998).

Codington, J., et al., "Nucleosides. XIII. Synthesis of 3'-amino-3'-deoxy-arabinosyl-uracil via 2',3'-epoxy-lyxosyl nucleosides," *J. Org. Chem.*, 27:163-167 (1962).

Colvin, V., et al., "Semiconductor Nanocrystals covalently bound to metal surfaces with self-assembled monolayers," *J. Am. Chem. Soc.*, 114:5221-5230 (1992).

Conway, N., et al., "Site-specific attachment of labels to the DNA backbone," *Oligonucleotides and Analogues: A Practical Approach*, 3:211-239, IRL Press: Oxford, GB (1991).

Delamarche, E., et al., "Immobilization of Antibodies on a Photoactive Self-assembled Monolayer of Gold," *Langmuir*, 12:1997-2006 (1996).

Dwyer, T., et al., "Structural Analysis of Covalent Peptide Dimers, Bis(pyridine-2-carboxamidonetropsin) (CH2)3-6, in Complex with 5'-TGACT-3' Sites by Two Dimensional NMR," *J. Am. Chem. Soc.*, 115:9900-9906 (1993).

Flanagan, J., et al., "Truncated staphylococcal nuclease is compact but disordered," *Proc. Natl. Acad. Sci. USA*, 89:748-752 (1992).

Gafni, Y., et al., "Biomimetic Ion-Binding Monolayers on Gold and Their Characterization by AC-Impedance Spectroscopy," *Chemistry—Eur. J.*, 2(7):759-766 (1996).

Gait, M., "Oligoribonucleotide Synthesis," *Oligonucleotides and Analogues: A Practical Approach*, 3:25-48, IRL Press: Oxford, GB (1991).

Gassner, N., et al., "A test of the 'jigsaw puzzle' model for protein folding by multiple methionine substitutions within the core of T4 lysozyme," *Proc. Natl. Acad. Sci. USA*, 93:12155-12158 (1996).

Glover, D., et al., "Alternating current polarography in the harmonic multiplex mode," *Anal. Chem.*, 45(11);1869-1877 (1973).

Griffin, T., et al., "Single-nucleotide polymorphism analysis by MALDI-TOF mass spectrometry," *Trends Biotechnol.*, 14(10):77-84 (2000).

Hamill, S., et al., "The effect of boundary selection on the stability and folding of the third fibronectin type III domain from human tenascin," *Biochemistry*, 37:8071-8079 (1998).

Hsueh, C., et al., "Electrochemically directed self-assembly on gold," *Agnew Chem. Intl. Ed. Engl.*, 39(7):1227-1230 (2000).

Hsung, R., et al., "Synthesis and characterization of unsymmetric ferrocene-terminated phenylethynyl oligomers," *Organometallics*, 14:4808-4815 (1995).

Kirschenheuter, G., et al., "An improved synthesis of 2'-azido-2'-deoxyurdine," *Tet. Lett.*, 35(46):8517-8520 (1994).

Krider, E.S., et al., "Automated Synthesis of 3' Metalated Oligonucleotides," *Inorg. Chem.*, 40:4002-4009 (2001).

Krider, E.S., et al., "Electron transfer in DNA: covalent attachment of spectroscopically unique donor and acceptor complexes," *J. Biol. Inorg. Chem.*, 3:222-225 (1998).

Kumar, A., et al., "A simple method for introducing -SH-COOH group at 5'-CH end of oligonucleotide," *Nucleos. Nucleot.*, 11(5):999-1002 (1992).

Laibinis, P., et al., "Orthogonal self-assembled monolayers: aklanethiols on gold and alkane carboxylic acids on alumina," *Science*, 245:845-847 (1989).

Langen, R., et al., "Electron Tunneling in Proteins: Coupling Through a β Strand," *Science*, 268:1733-1735 (1995).

Löfås, S., et al., "A novel hydrogel matrix on gold surfaces in surface plasmon resonance sensors for fast and efficient covalent immobilization of ligands," *Chem. Comm.*, _: 1526-1528 (1990).

McGee, D., et al., "Novel nucleosides via intramolecular functionalization of 2,2'-anhydrouridine derivatives," *Tet. Lett.*, 37(12);1995-1998 (1996).

Mengel, R., et al., "A simple synthesis of 2'-deoxy-2'-fluorocytidine by nucleophilic substitution of 2,2'-anhyrocytidine with potassium fluoride/crown ether," *Agnew Chem. Intl. Ed. Eng.*, 17(7):525 (1978).

Mitsui, T., et al., "Coumarin-fluorescein pair as a new donor-acceptor set for fluorescence energy transfer study of DNA," *Tet. Lett.*, 41(15):2605-2608 (2000).

Moffatt, J.G., "Chemical transformations of the sugar moiety of nucleosides," *J. Inst. Org. Chem.*, 527:71-164 (1979).

Mrksich, M., et al., "Enhanced Sequence Specific Recognition in the Minor Groove of DNA by Covalent Peptide Dimers: Bis(pyridine-2-carboxamidonetropsin) (CH2)3-6," *J. Am. Chem. Soc.*, 115(22):9898-9899 (1993).

Mutz, M., et al., "Conformational dependence of electron transfer across de novo designed metalloproteins," *Proc. Natl. Acad. Sci. USA*, 93;9521-9526 (Sep. 1996).

O'Donnell-Maloney, M., et al., "The development of microfabricated arrays for DNA sequencing and analysis," *Trends Biotechnol.*, 14(10):401-407 (1996).

Parikh, A., et al., "An instrinsic relationship between molecular structure in self-assembled n-alkylsiloxane monolayers and deposition temperature," *J. Phys. Chem.*, 98:7577-7590 (1994).

Pieken, W.A., et al., "Kinetic characterization of ribonucloease resistant 2'-modified hammerhead ribozymes," *Science*, 253:314-317 1991.

Plaxco, K., et al., "Simplified proteins: minimalist solution to the 'protein folding problem'," *Curr. Opin. Struct. Biol.*, 8:80-85 (1998).

Plaxco, K., et al., "The importance of being unfolded," *Nature*, 386:657-659 (1997).

Prime, K., et al., "Adsorption of proteins onto surfaces containing end-attached oligo(ethylene oxide): a model system using self-assembled monolayers," *J. Am. Chem. Soc.*, 115:10714-10721 (1993).

Schierbaum, K.D., et al., "Molecular recognition by self-assembled monolayers of cavitand receptors," *Science*, 265:1413-1415 (1994).

Sebesta, D., et al., "2'-Deoxy-2'-alkoyaminouridines: novel 2'-substituted uridines prepared by intramolecular nucleophilic ring opening at 2,2'-O-anhydrouridines," *Tetrahedron*, 52(46):14385-14402 (1996).

Shnek, D.R., et al., "Specific protein attachment to artificial membranes via coordination to lipid-bound cooper(II)," *Langmuir*, 10:2382-2388 (1994).

Sinha, N.D., et al., "Oligonucleotides with reporter groups attached to the 5'-terminus," *Oligonculeotides and Analogues: A Practical Approach*, R. Eckstein (ed.), 8:185-210, IRL Press: Oxford, GB (1991).

Spinke, J., et al., "Molecular recognition of self-assembled monolayers: optimization of surface functionalization," *J. Chem. Phys.*, 99(9):7012-7019 (1993).

Sproat, B.S., et al., "2'-O-methyloligoribonucleotides: synthesis and application," *Oligonculeotides and Analogues: A Practical Approach*, R. Eckstein (ed.), 3:211-239, IRL Press: Oxford, GB (1991).

Uto, Y., et al., "Electrochemical Analysis of DNA Amplified by the Polymerase Chain Reaction with a Ferrocenylated Oligonucleotide," *Anal. Chem.*, 250:122-124 (1997).

Uversky, V.N., et al., "Effect of natural ligands on the structural properties and conformational stability of proteins," *Biochemistry (Moscow)*, 63(4):420-433 (1998).

Vaughan, T., et al., "Human antibodies by design," *Nat. Biotechnol.*, 16:535-539 (1998).

Verheyden, J.P.H., et al., "Synthesis of some pyrimidine 2'-amino-2'-deoxynucleosides," *J. Org. Chem.*, 36(2):250-254 (1971).

Whitesides, G., et al., "Wet chemical approaches to the characterization of organic surfaces: self-assembled monolayers, wetting, and the physical-organic chemistry of solid-liquid interface," *Langmuir*, 6:87-96 (1990).

Wilson, D., et al., "Phage display: applications, innovations, and issues in phage and host biology," *Can. J. Microbiol.*, 44:313-329 (1998).

XI, Z., et al., "New stereocontrolled synthesis of isomeric C-branched-β-D-nucleosides by intramolecular free-radical cyclization-opening reactions based on temporary silicon connenction," *Tetrahedron*, 48(2):349-370 (1992).

Yu, C.J., et al., "2'-ribose ferrocene oligonucleotides for electronic detection of nucleic acids," *J. Org. Chem.*, 66:2937-2942 (2001).

Yu, C.J., et al., "Uridine-Conjugated-Ferrocene DNA Oligonucleotides for Electronic Detection of Nucleic Acids," *J. Am. Chem. Soc.*, 122:6767-6768 (2000).

Kolb, J., et al., "Small-scale acoustic streaming in liquids," *J. Acoustics Soc. Am.* 28(6):1237-1242 (1956).

Kretschmann, E., et al., "Radioactive decay of non radiative surface plasmons excited in light," *Z. Naturforsch.* 23A:2135-2136 (1968).

Rojas, M., et al., "Molecular recognition at the electrode-solution interface, design, self-assembly, and interfacial binding properties of a molecular sensor," *J. Am. Chem. Soc.*, 117(21):5883-5884 (May 1995).

Wallace, J., et al., "Electron transfer of yeast cytochrome C immobilized on SAM modified gold electrodes," *Book of Abstracts, 214th ACS Natl. Mtg.*, Las Vegas, NV, PHYS-326 (Sep. 7-11, 1997).

Wang, J., et al., "Peptide nucleic acid probes for sequence-specific DNA biosensors," *J. Am. Chem. Soc.* 118(33):7667-7670 (Aug. 1996).

Kolb, J., et al., "Small-scale acoustic streaming in liquids," *J. Acoustic Soc. Am.* 28(6):1237-1242 (1956).

Wang, J., et al., "Peptide Nucleic Acid Probes for Sequence-Specific DNA Biosensors," J. Am. Chem. Soc. 118(33):7667-7670 (Aug. 1996).

* cited by examiner

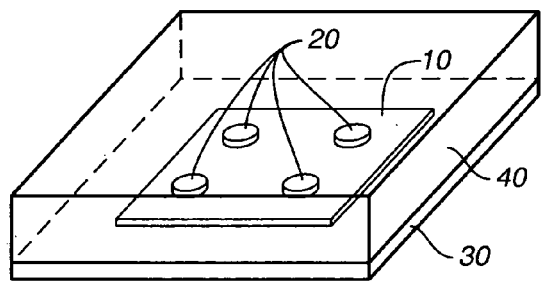
FIG._1A
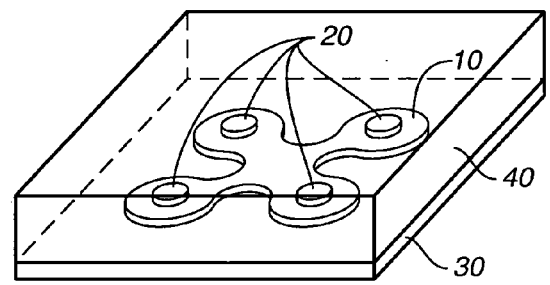
FIG._1B
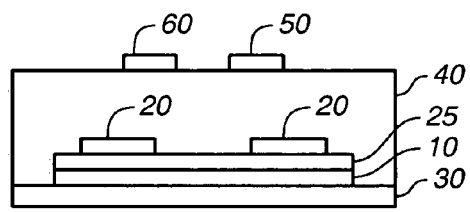
FIG._1C
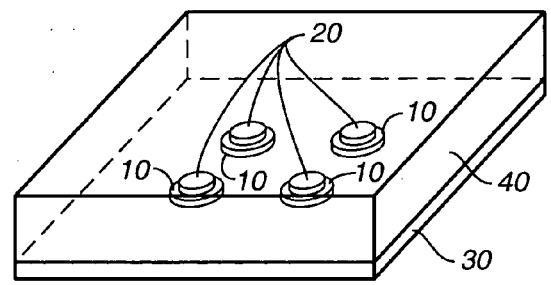
FIG._1D
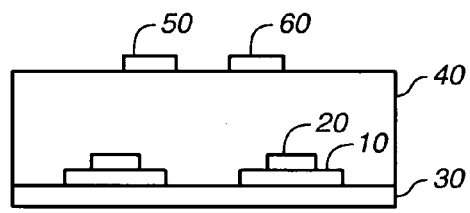
FIG._1E
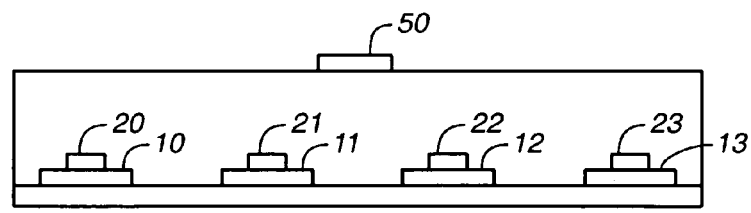
FIG._1F

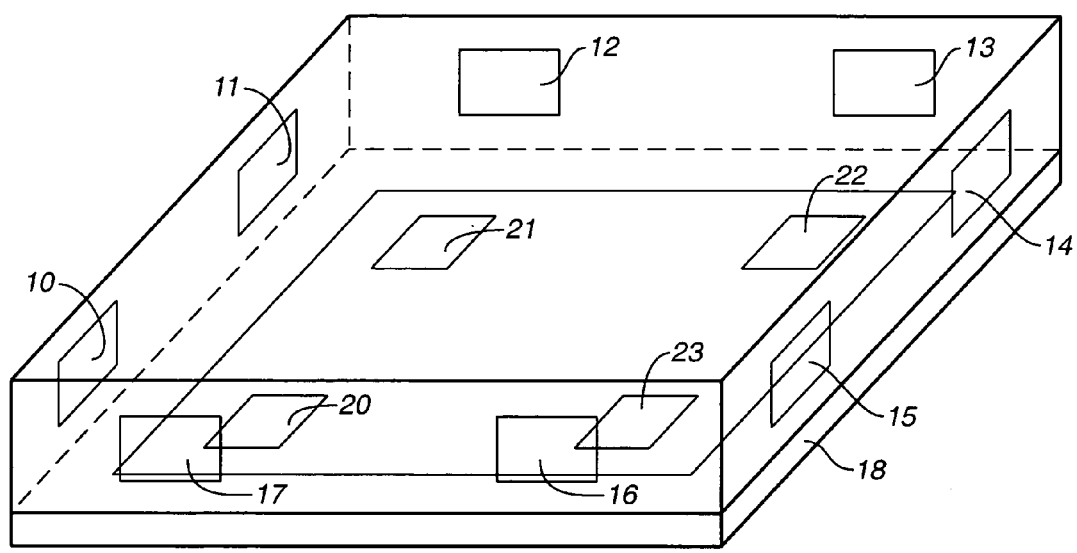
FIG._2
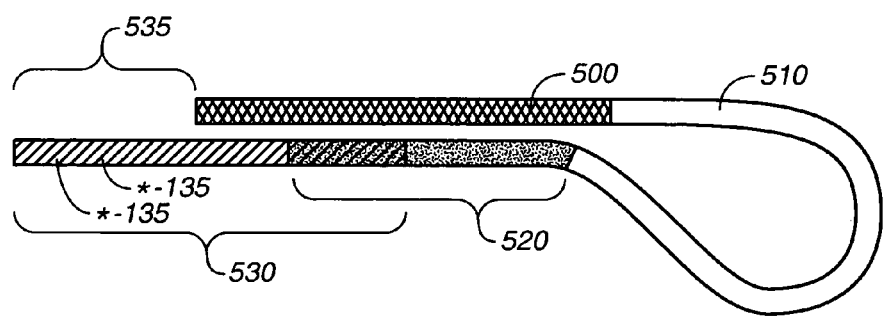
FIG._12

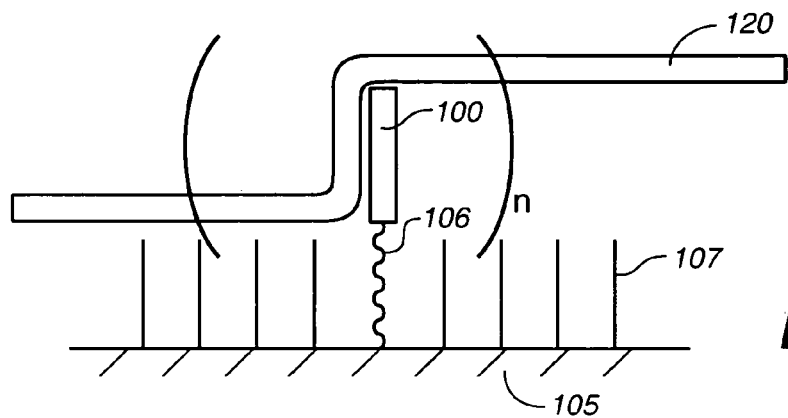
FIG._3A
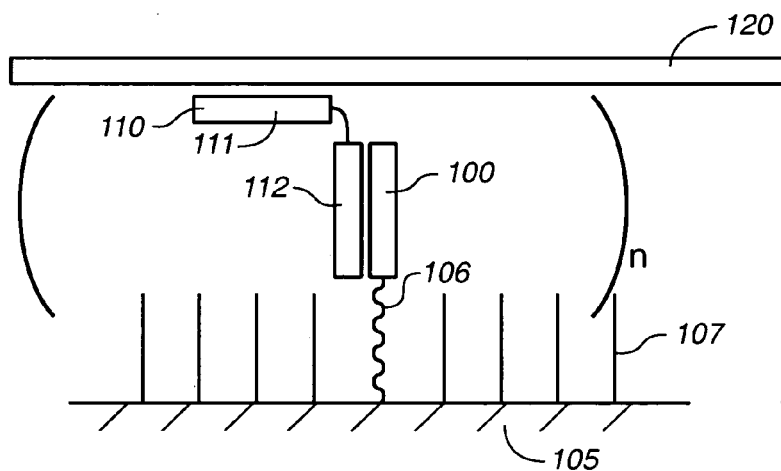
FIG._3B
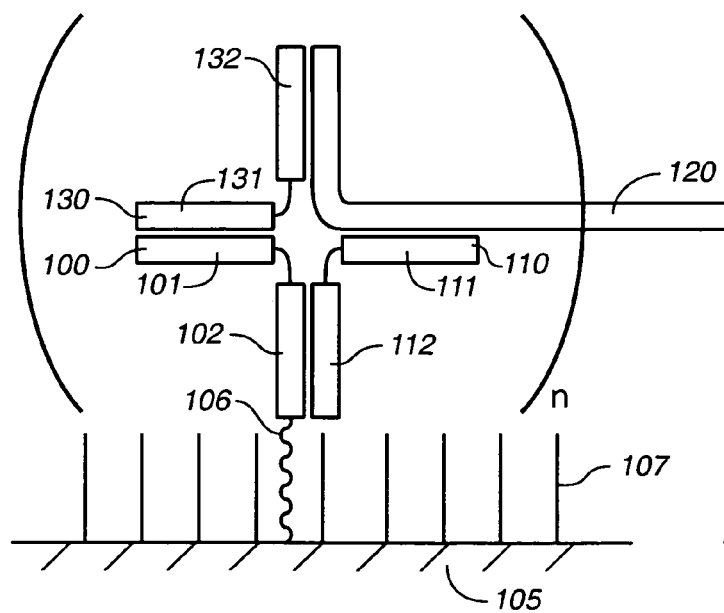
FIG._3C

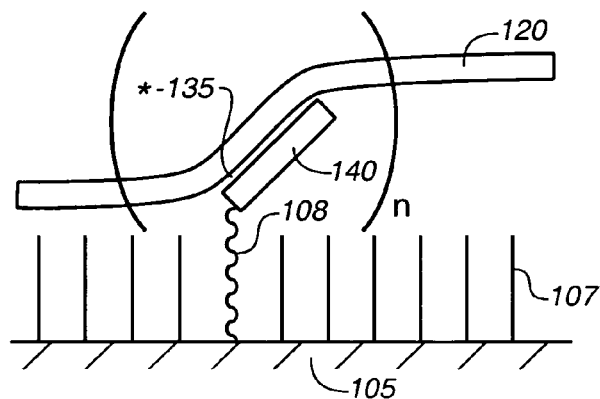
FIG._4A
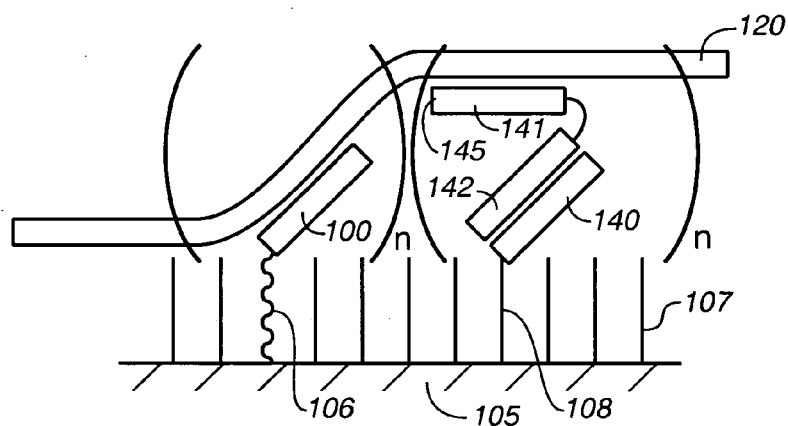
FIG._4B
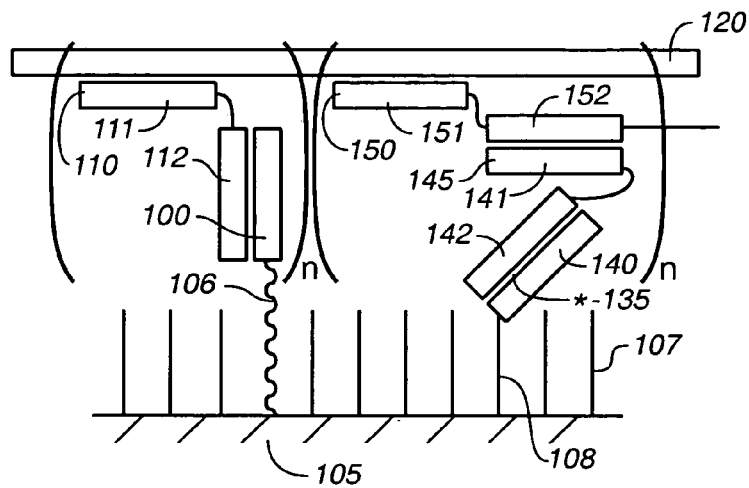
FIG._4C

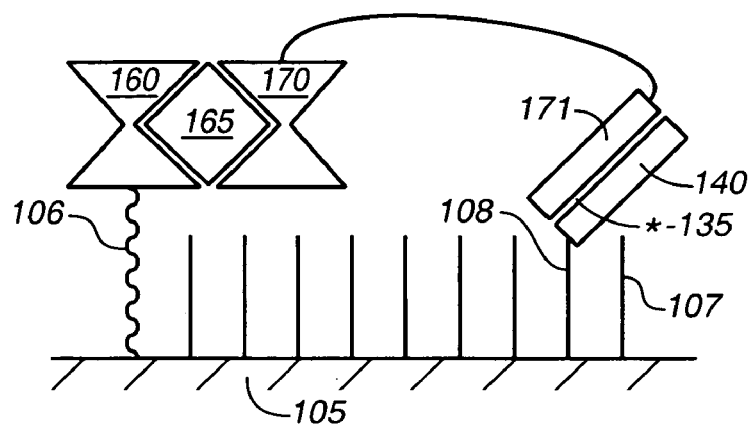
FIG._4D
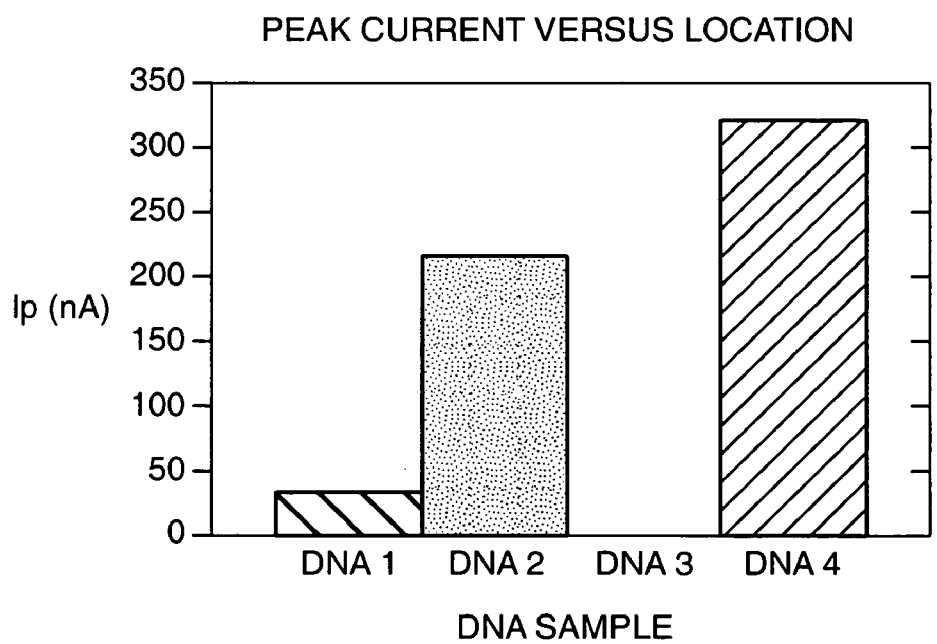
FIG._14

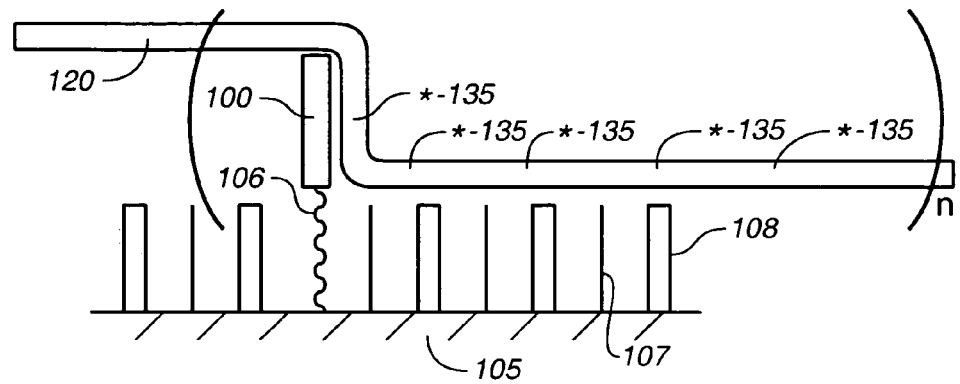
FIG._5A
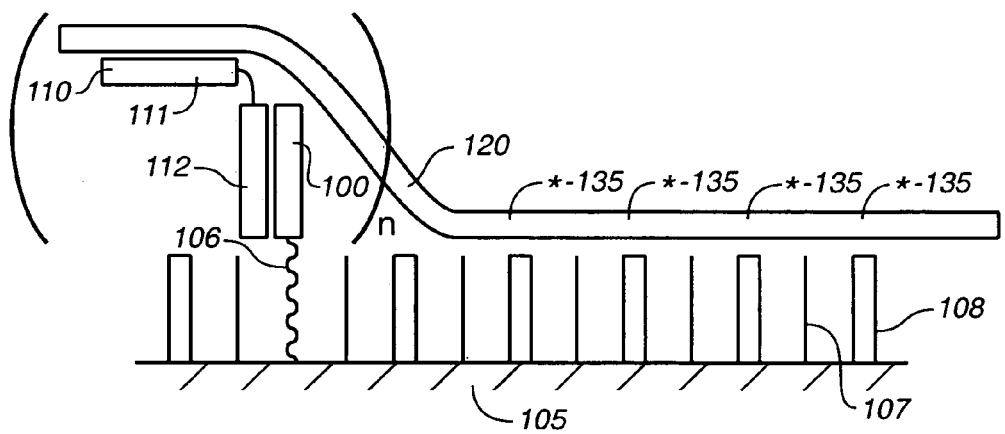
FIG._5B
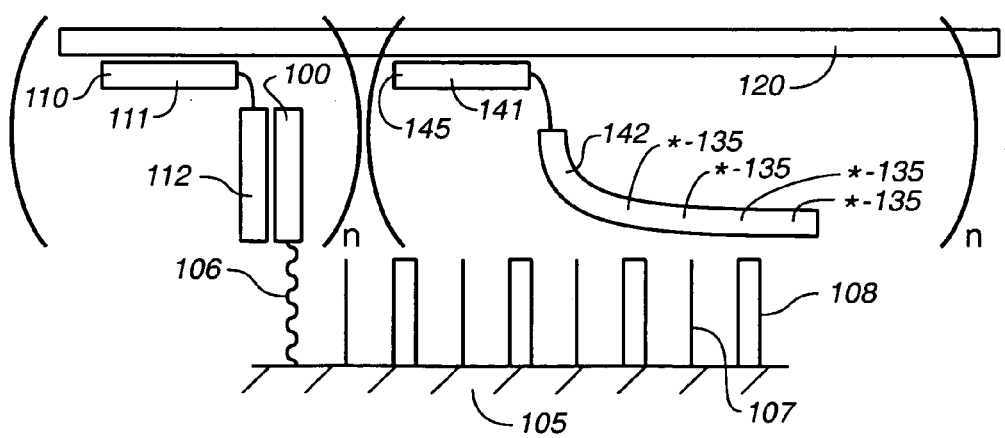
FIG._5C

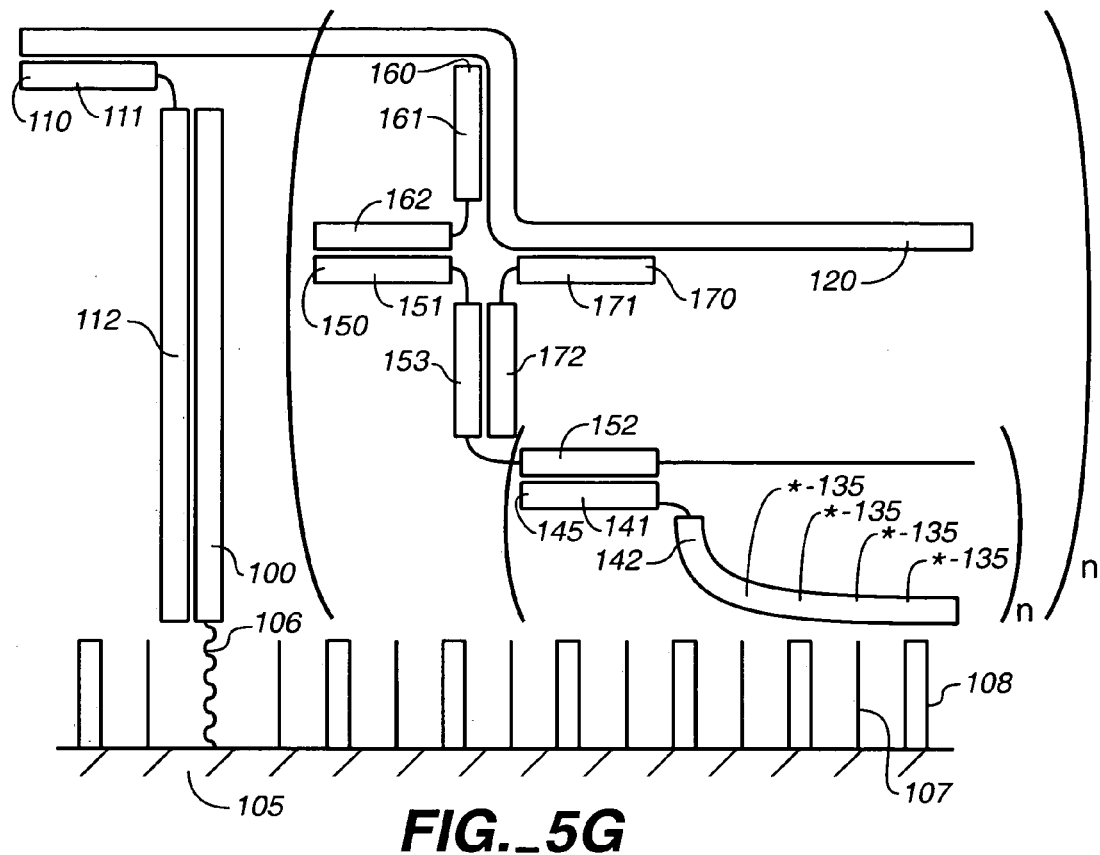
FIG._5G
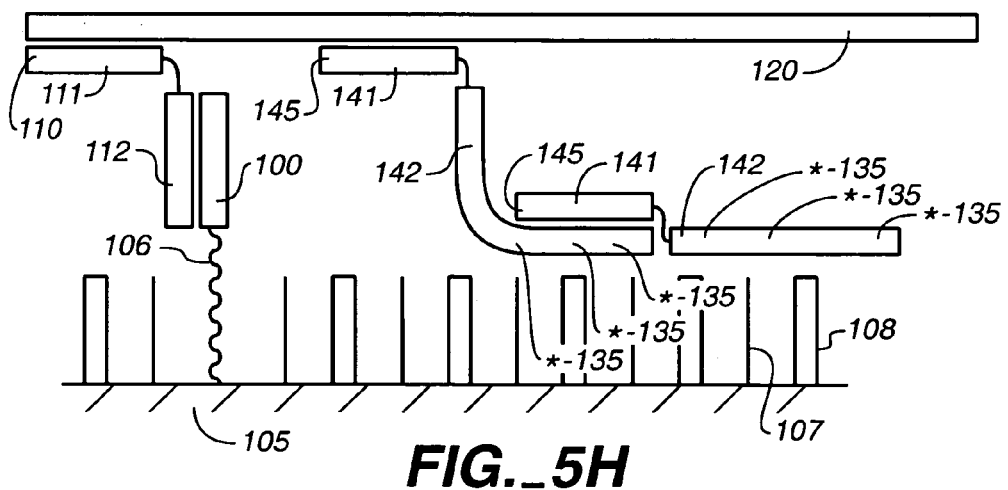
FIG._5H

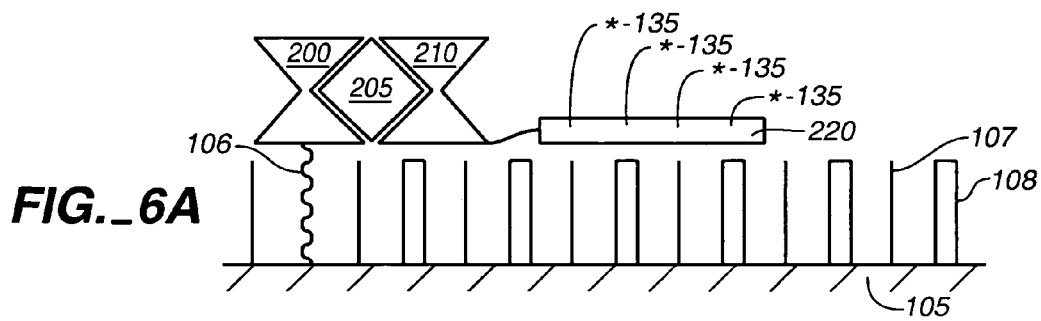
FIG._6A
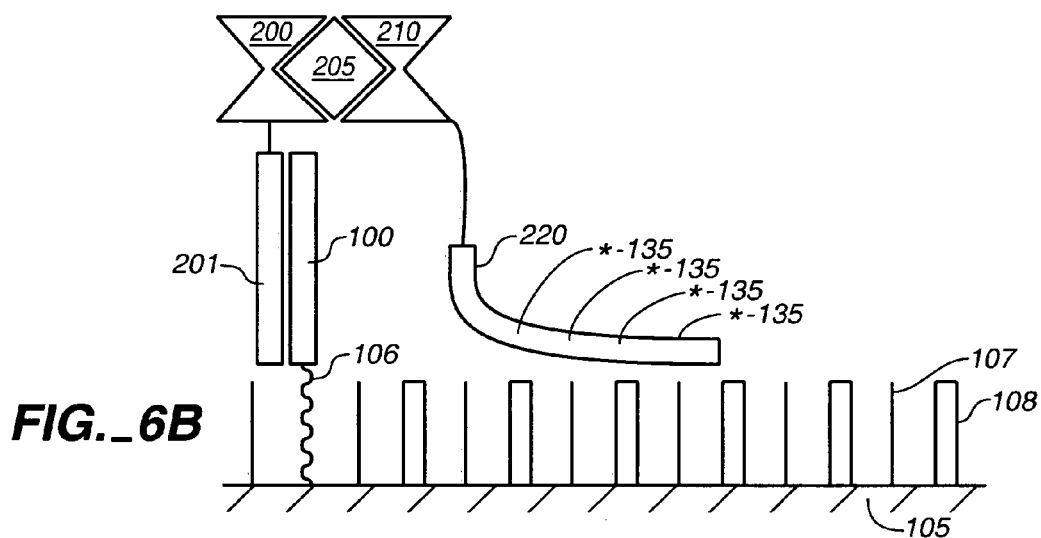
FIG._6B
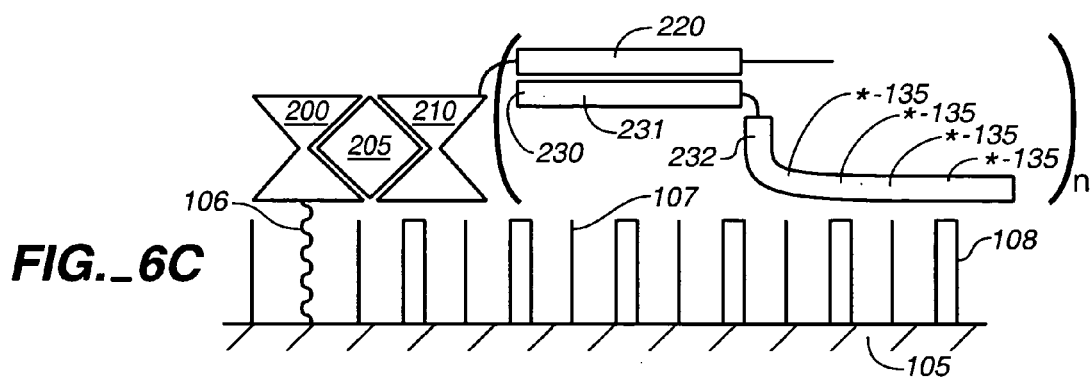
FIG._6C
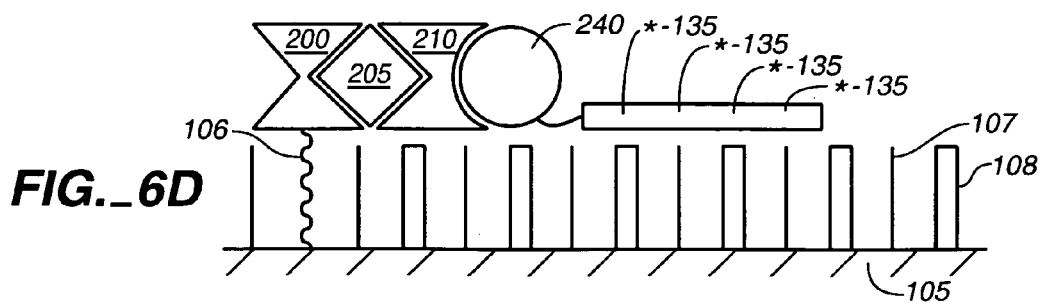
FIG._6D

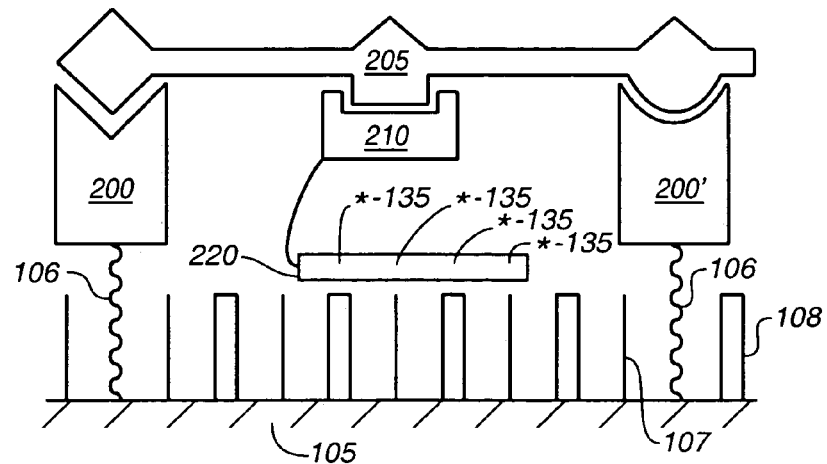
FIG._6E
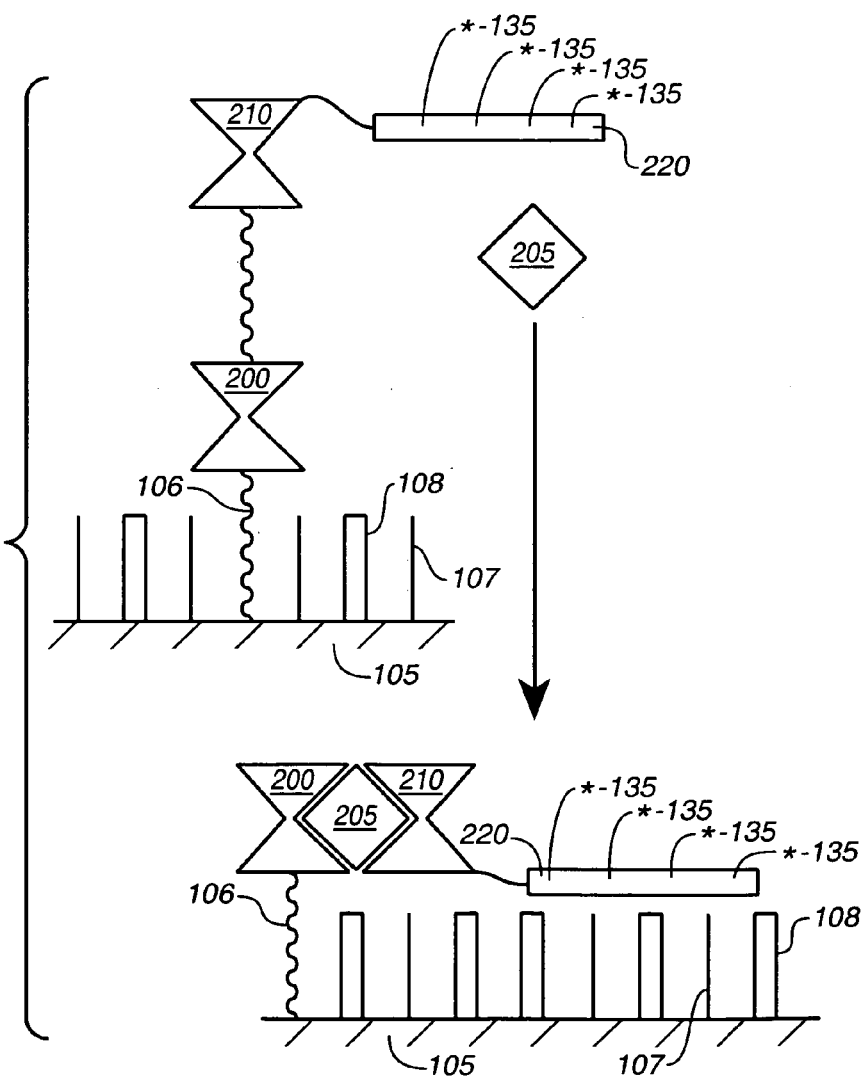
FIG._6F

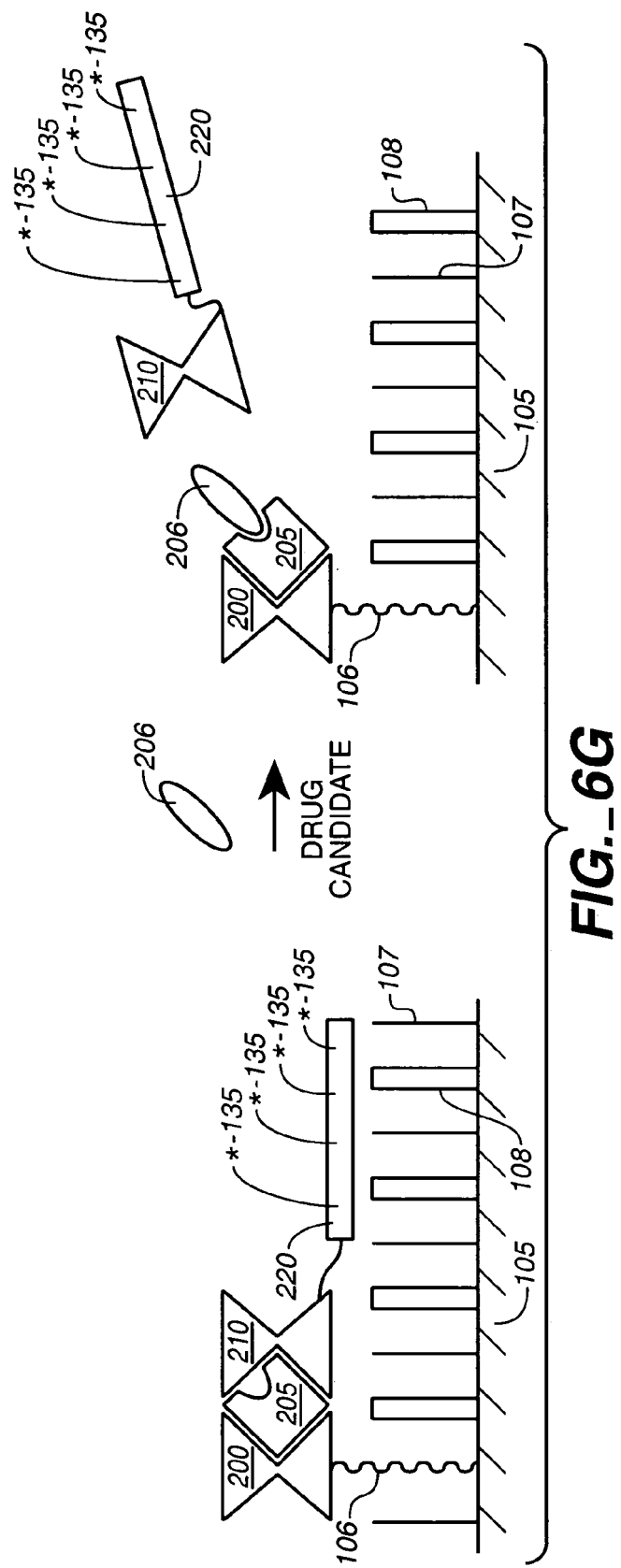
FIG._6G

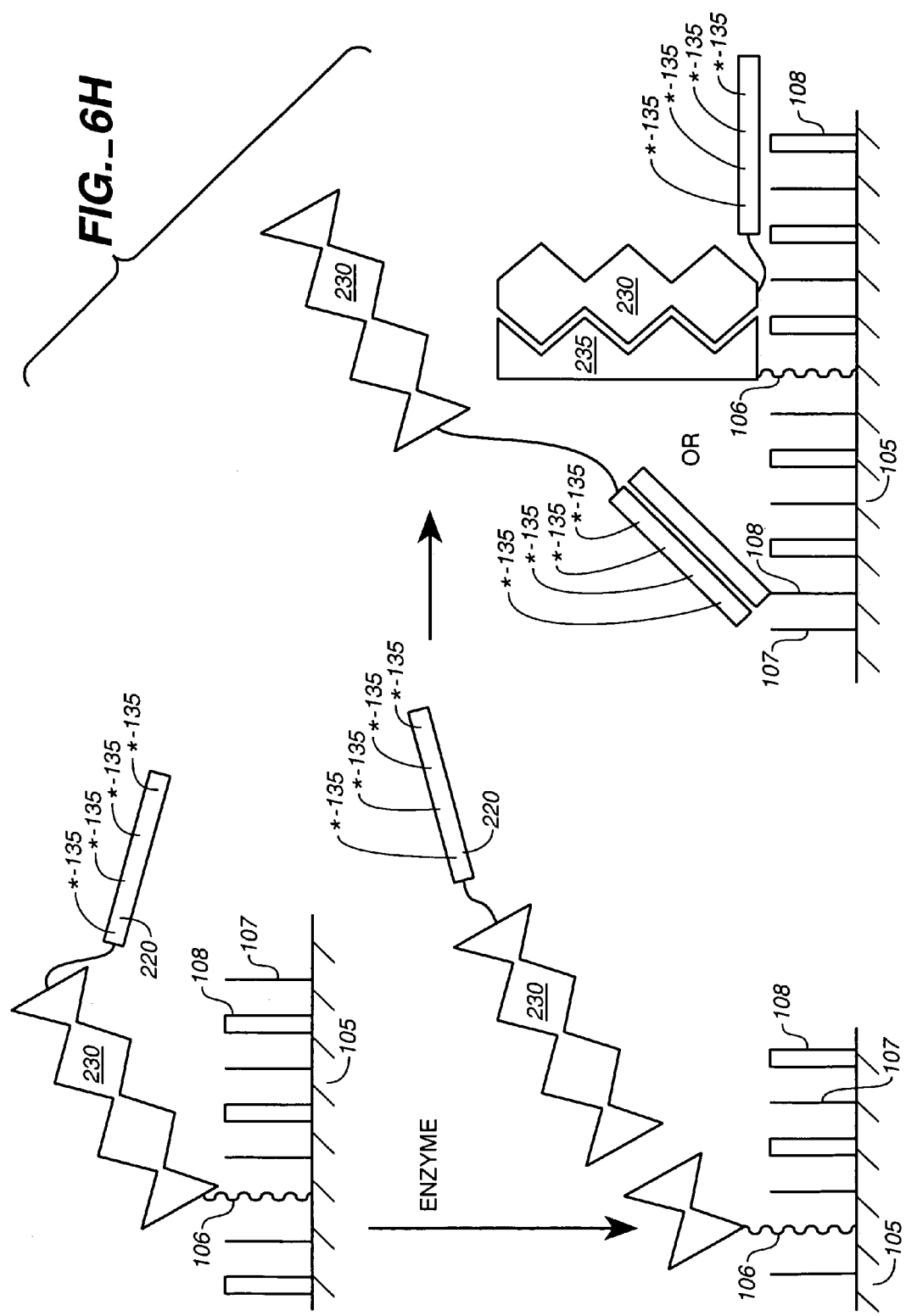

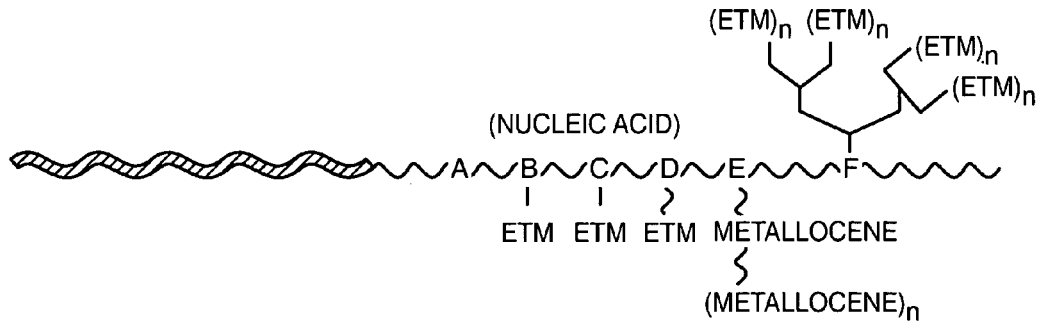
FIG._7A
A = NUCLEOSIDE REPLACEMENT
B = ATTACHMENT TO A BASE
C = ATTACHEMENT TO A RIBOSE
D = ATTACHMENT TO A PHOSPHATE
E = METALLOCENE POLYMER, ATTACHED TO A RIBOSE, PHOSPHATE, OR BASE
F = DENDRIMER STRUCTURE, ATTACHED VIA A RIBOSE, PHOSPHATE OR BASE
G = ATTACHMENT VIA A "BRANCHING STRUCTURE", THROUGH RIBOSE, PHOSPHATE OR BASE
FIG._7B

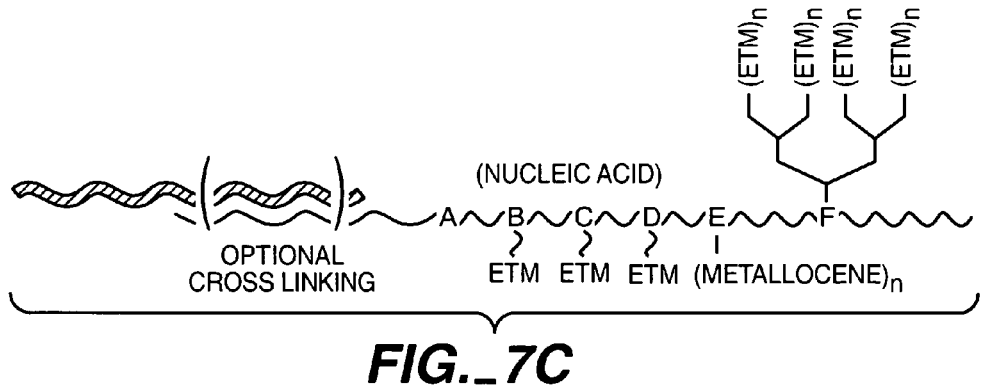
FIG._7C
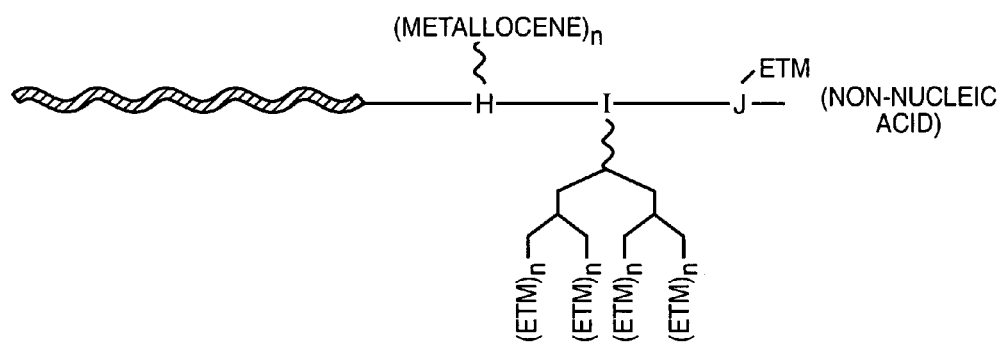
H = ATTACHMENT OF METALLOCENE POLYMERS
I = ATTACHMENT VIA DENDRIMER STRUCTURE
J = ATTACHMENT USING STANDARD LINKERS
FIG._7D
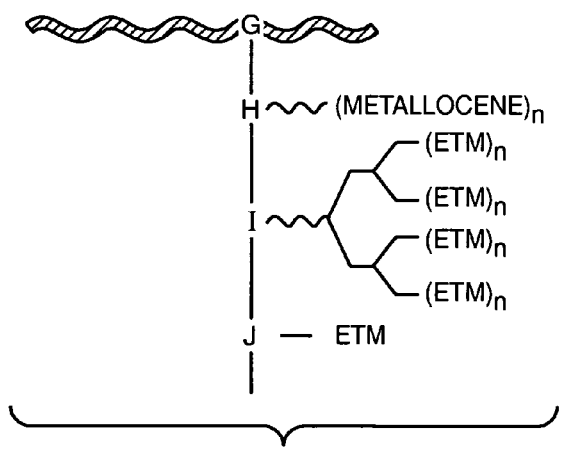
FIG._7E

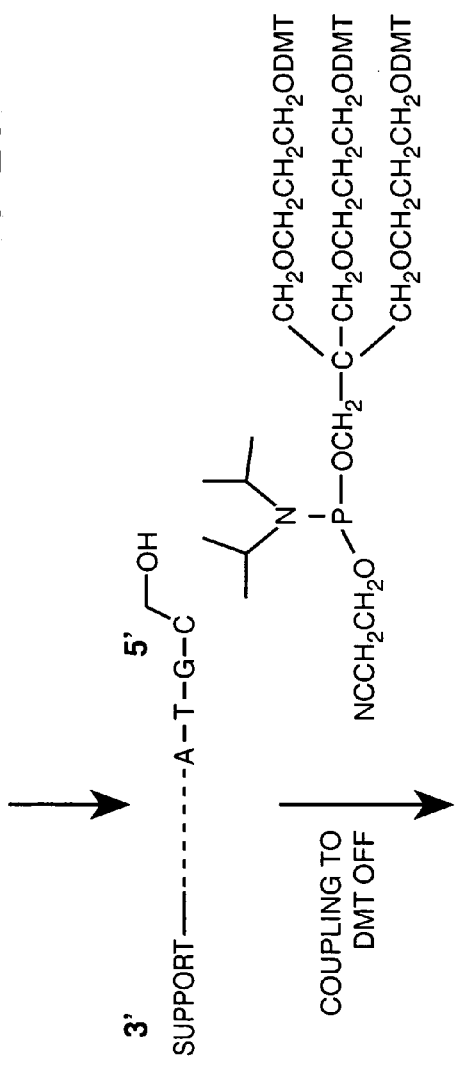
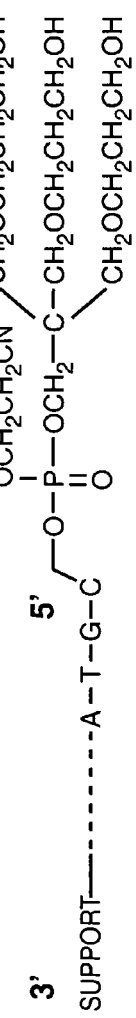
FIG._8A

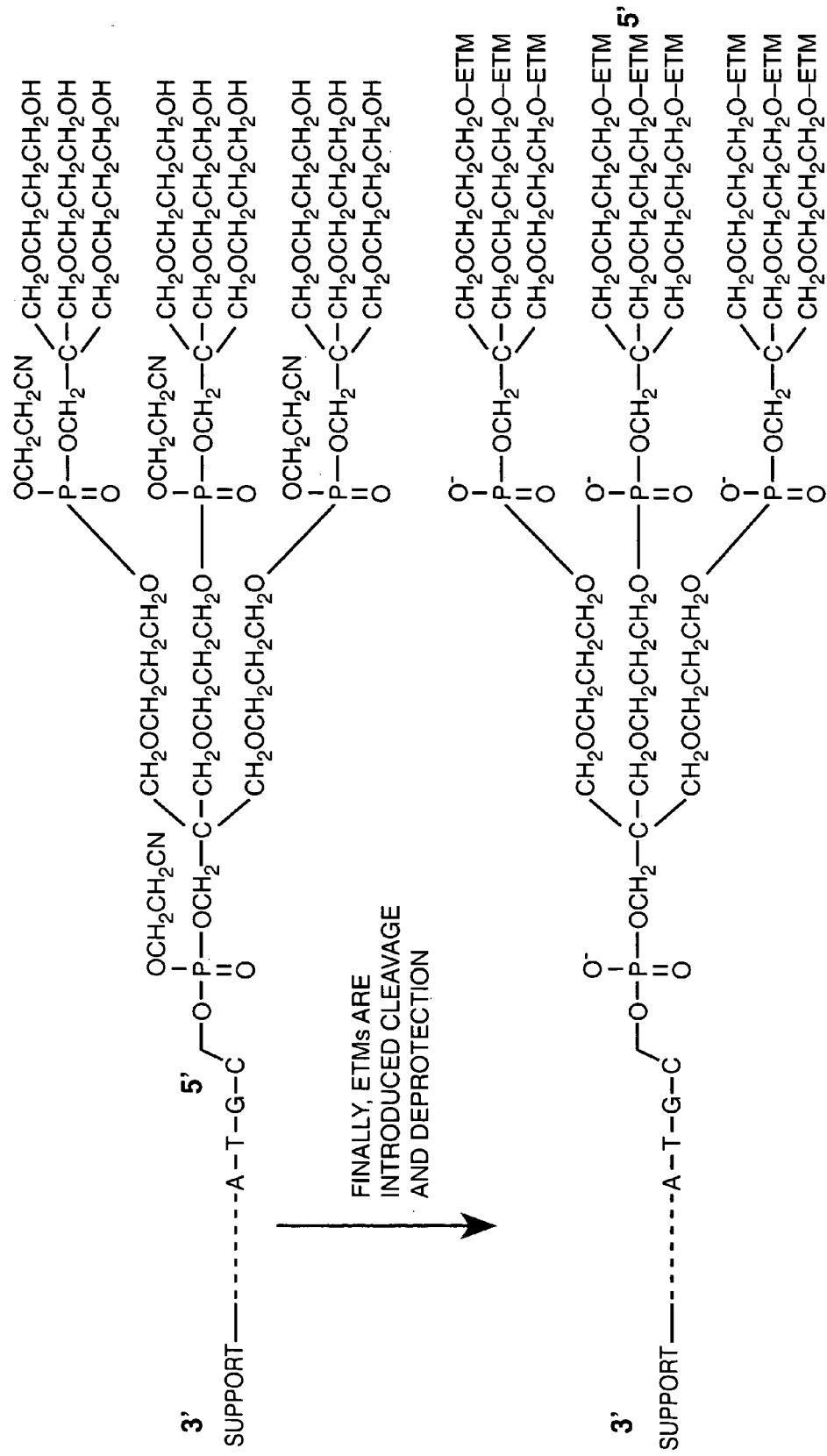
FIG._8B

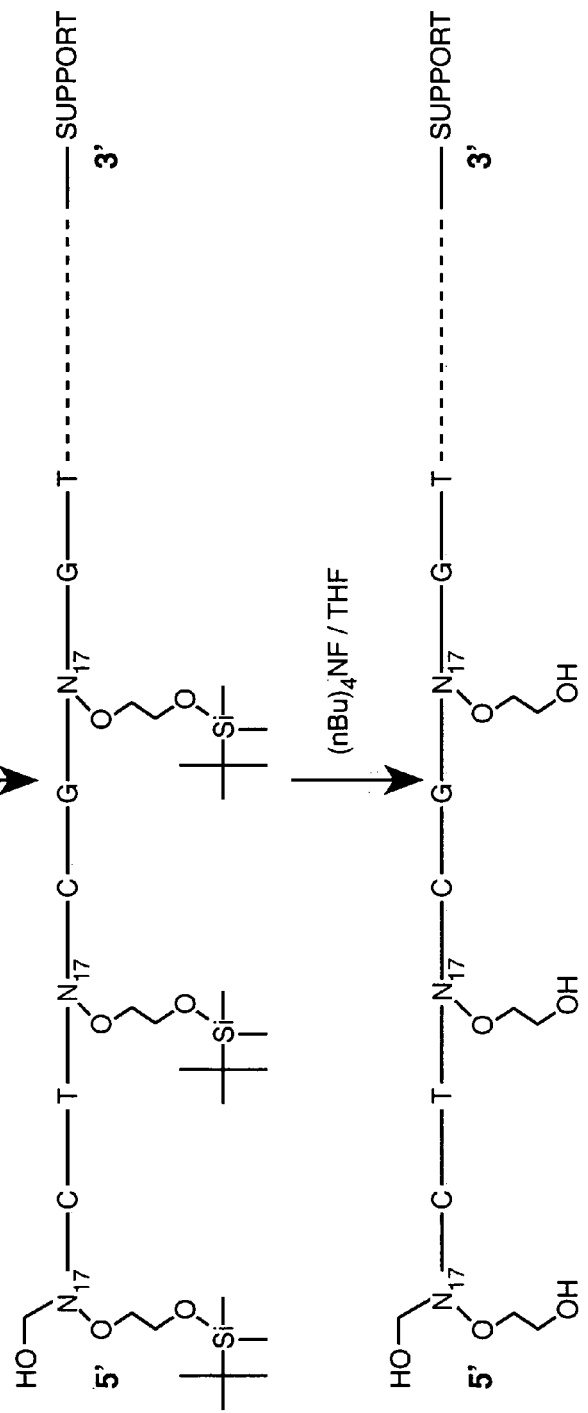

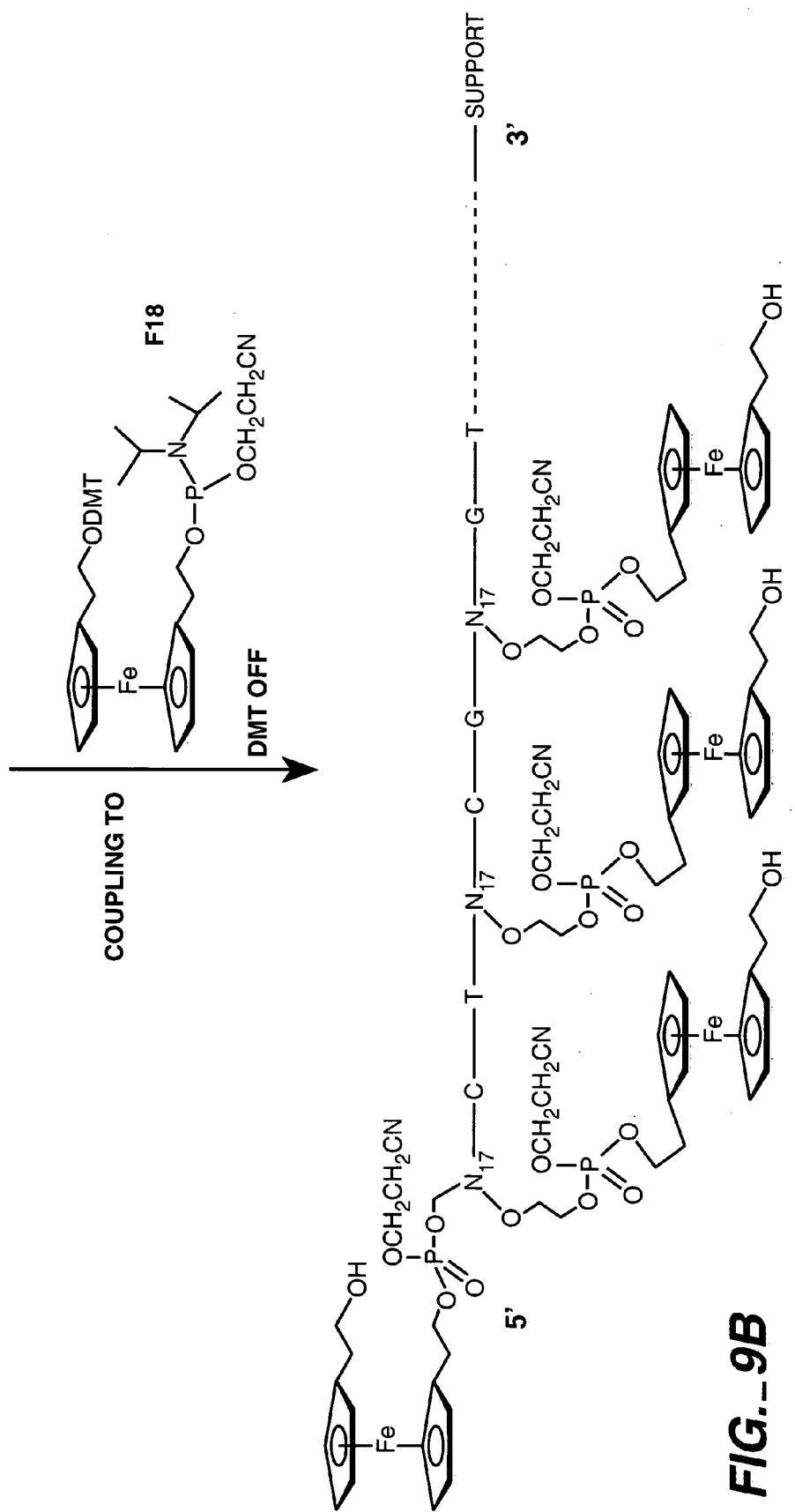
FIG._9B

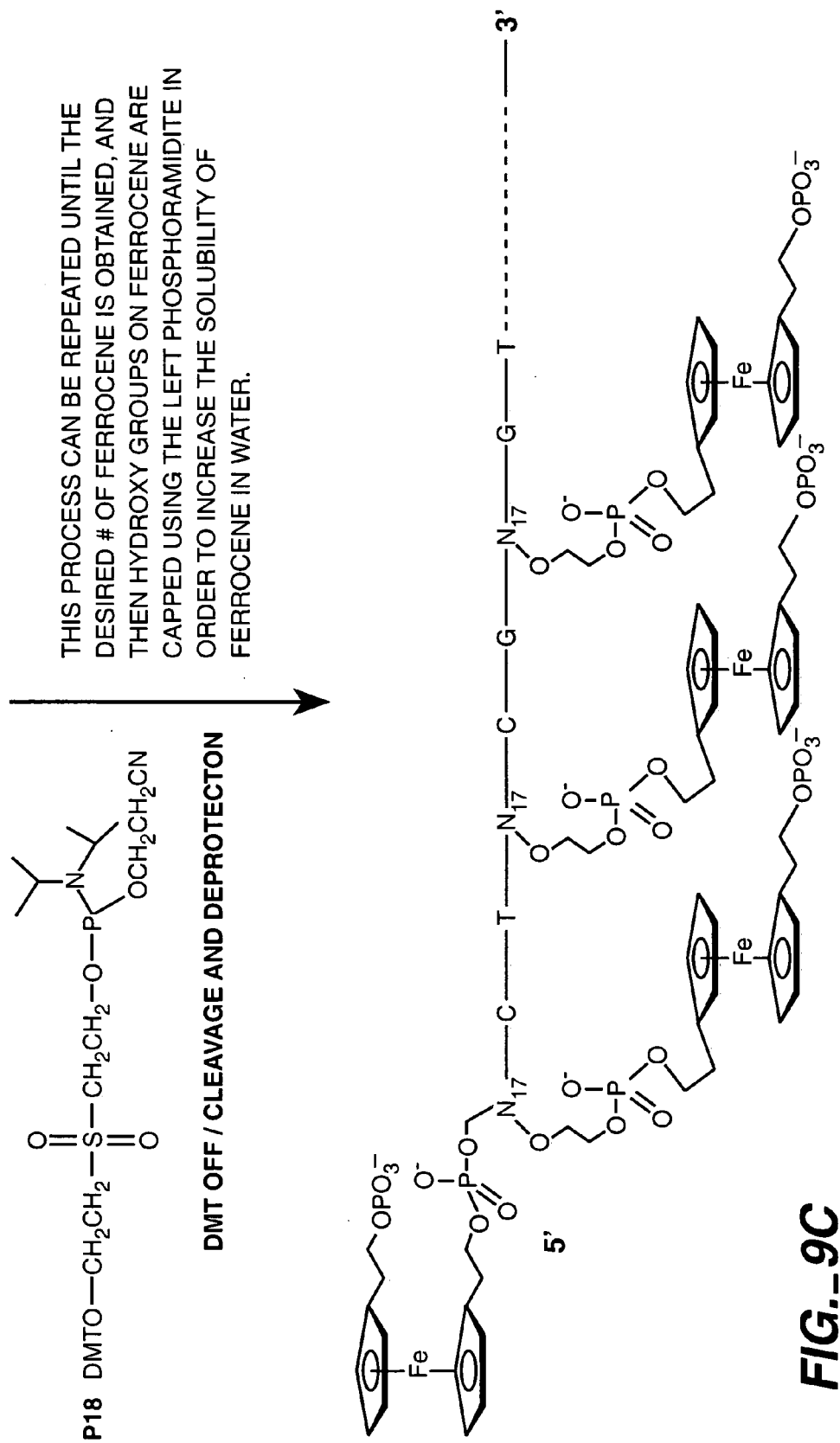
FIG._9C

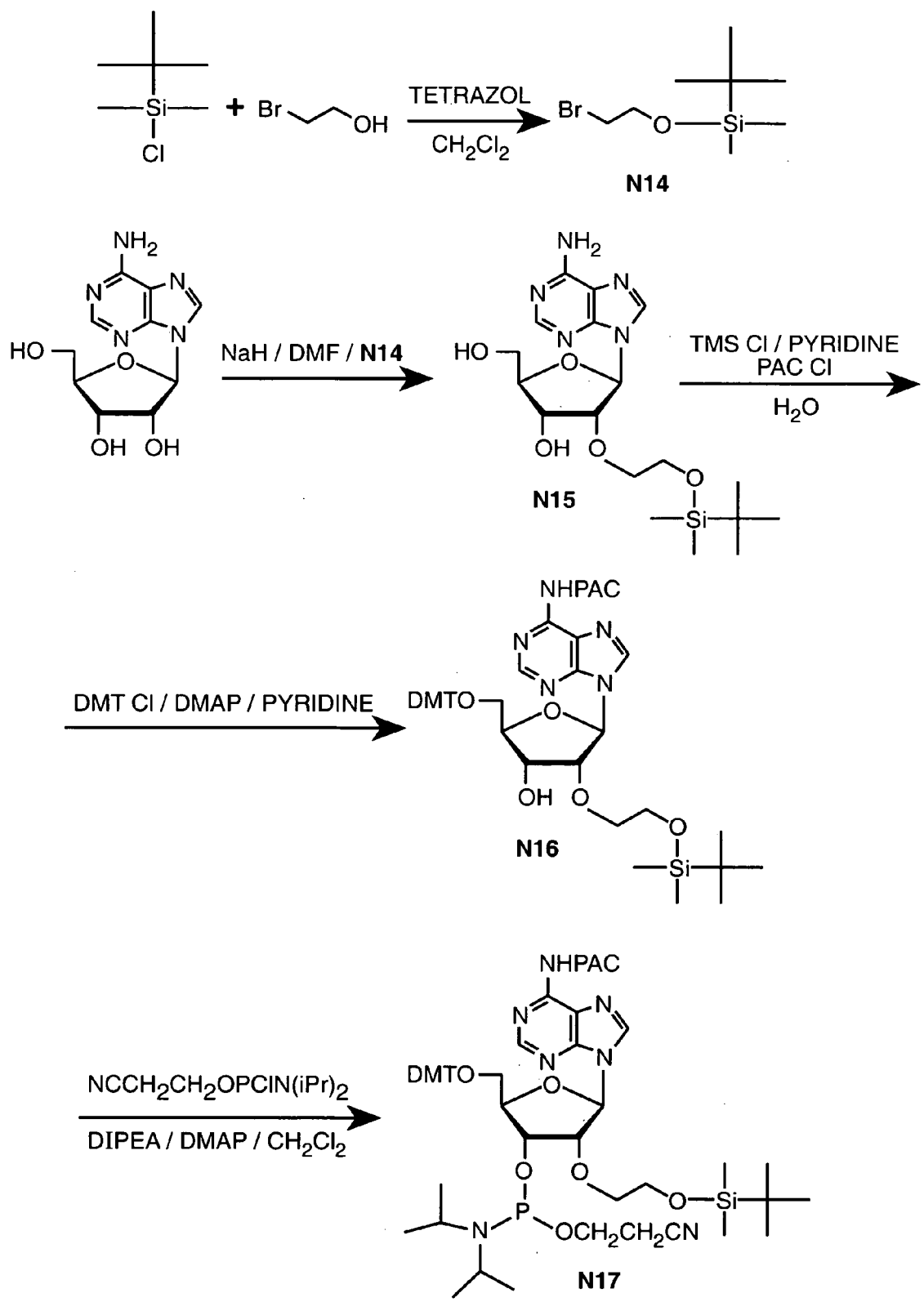
FIG._10

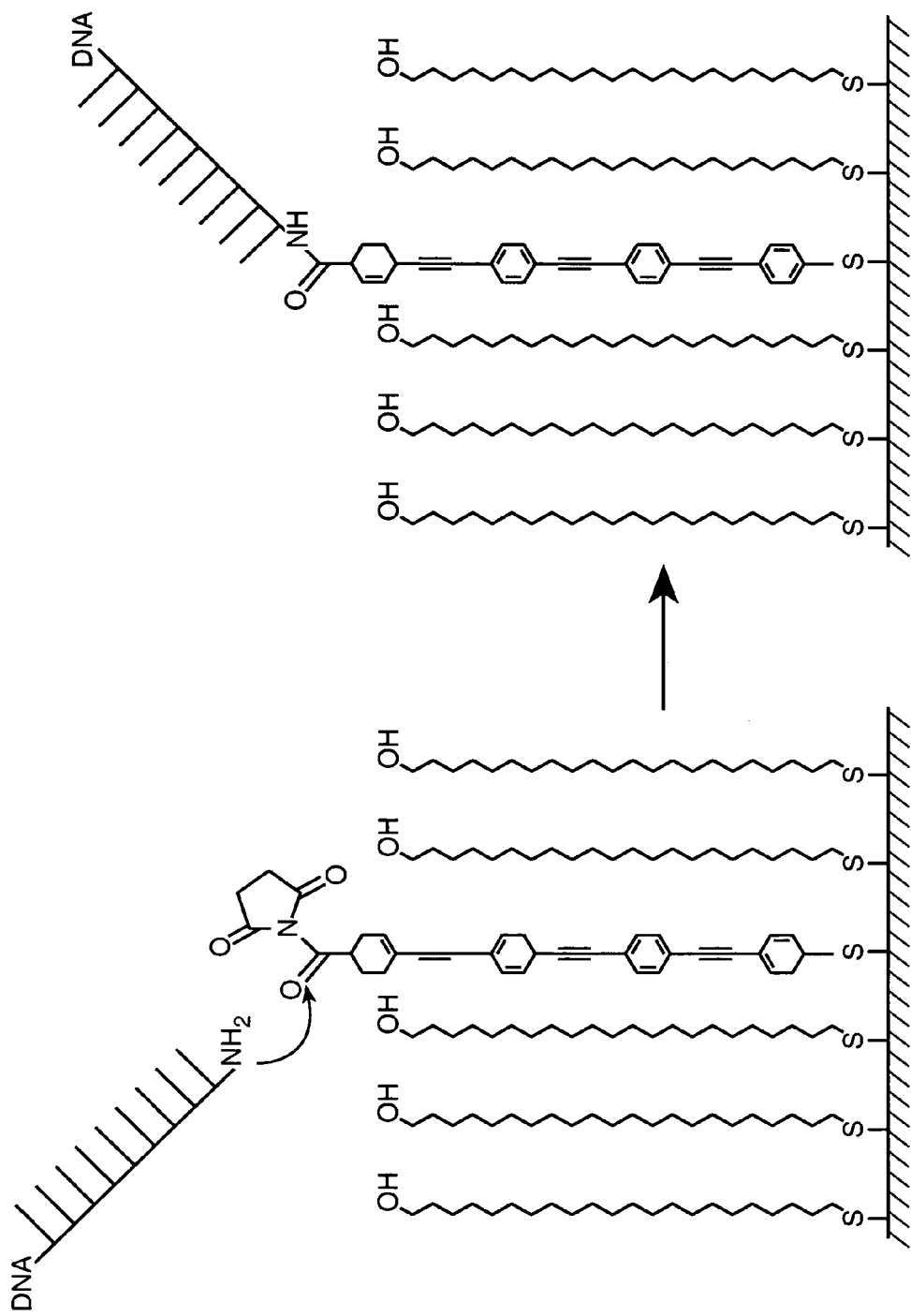
FIG._11

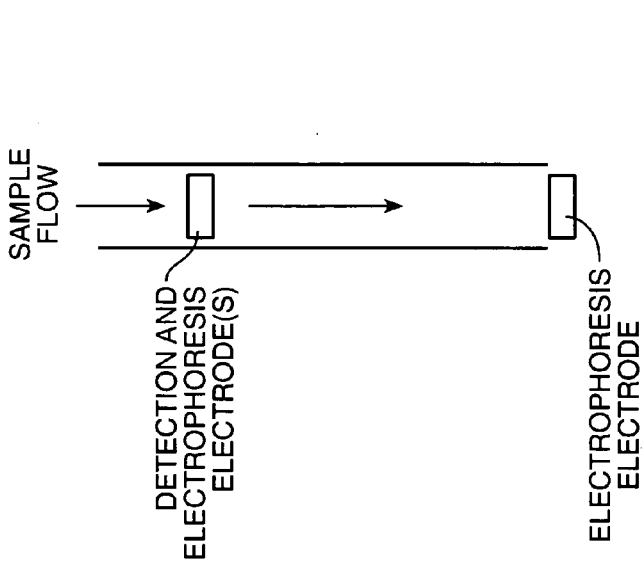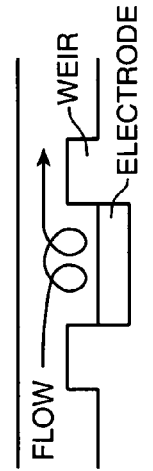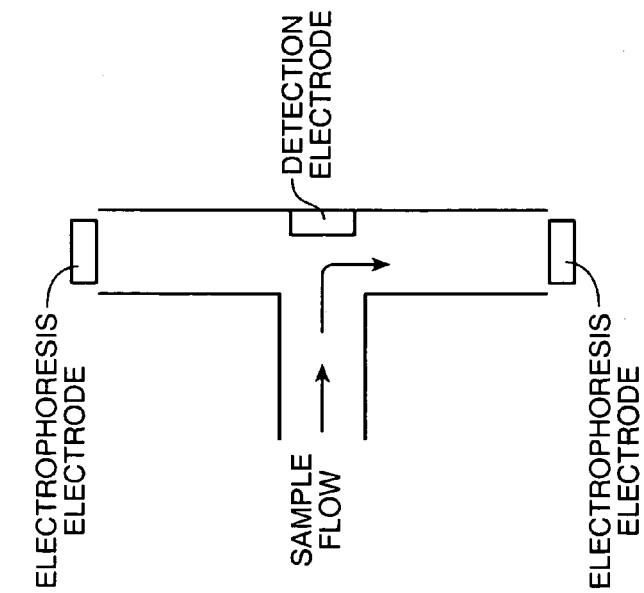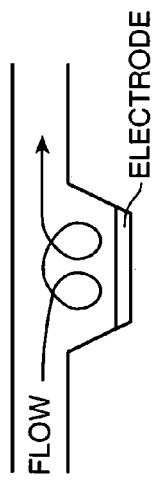
FIG._13A  FIG._13B  FIG._13C  FIG._13D

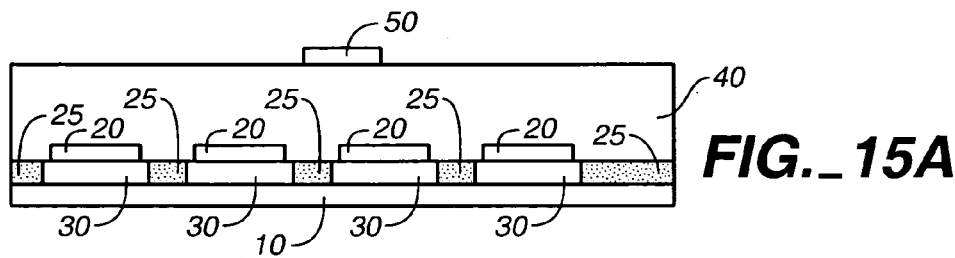
*FIG._15A*
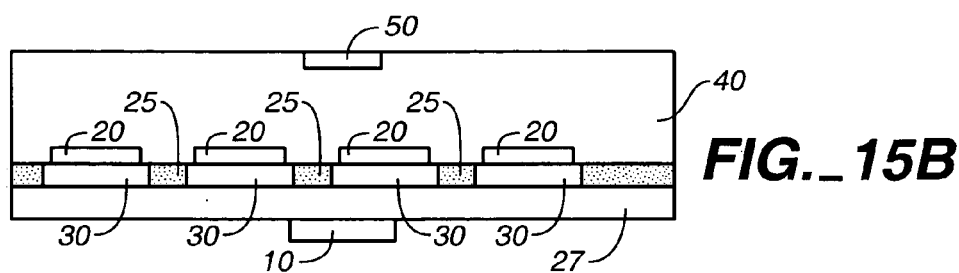
*FIG._15B*
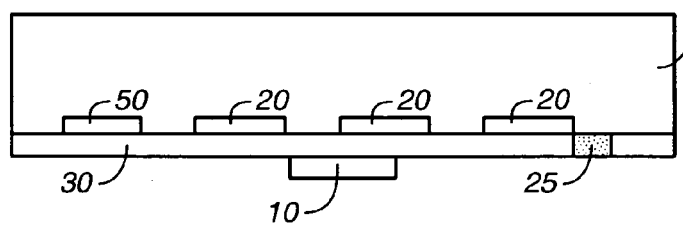
*FIG._15C*
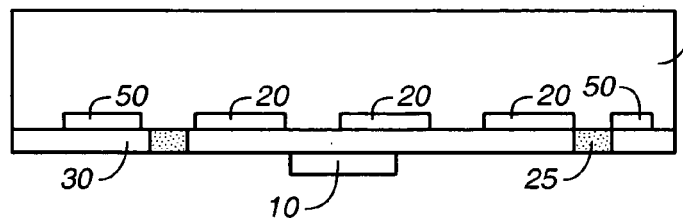
*FIG._15D*
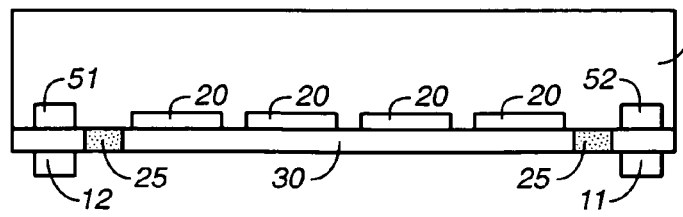
*FIG._15E*

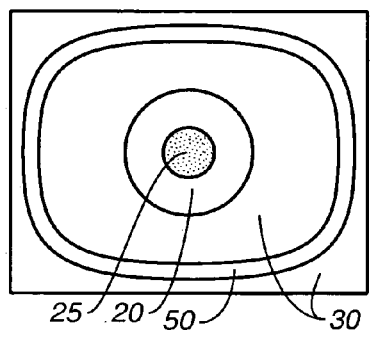
FIG._15F
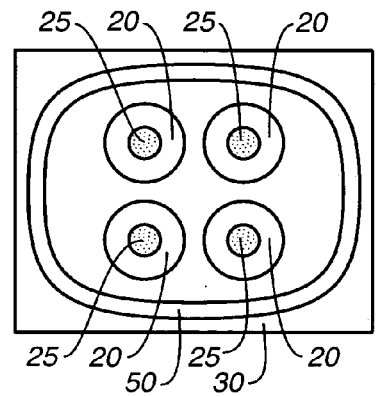
FIG._15G
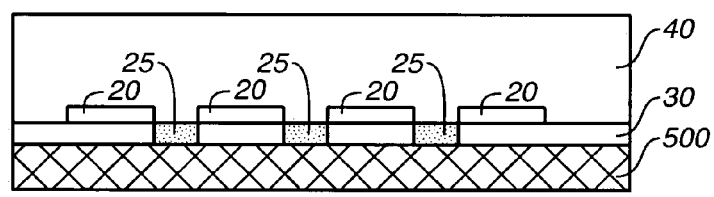
FIG._16A
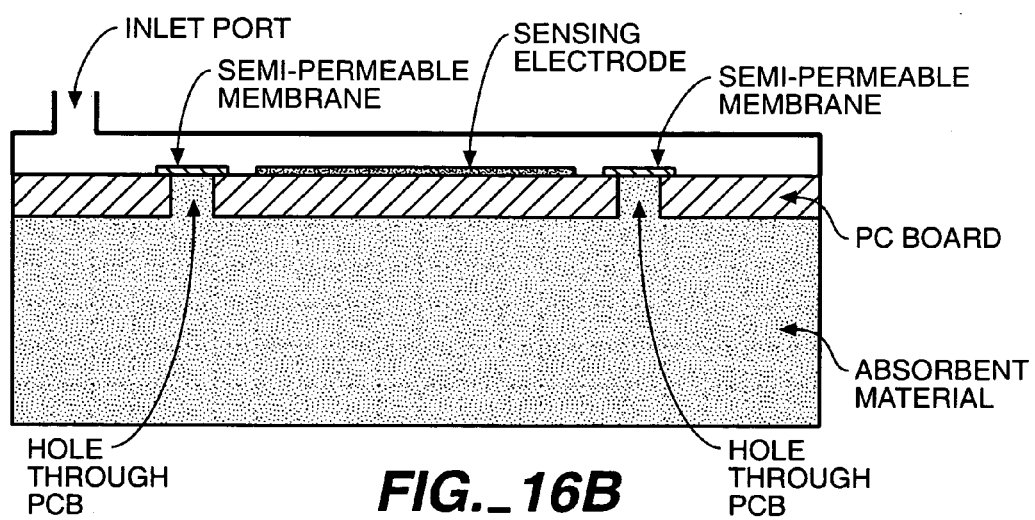
FIG._16B

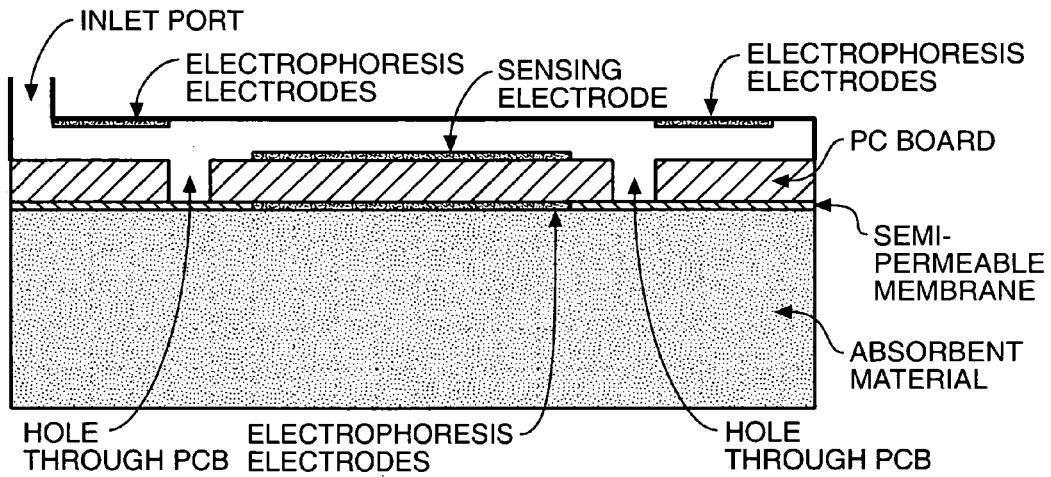
FIG._16C
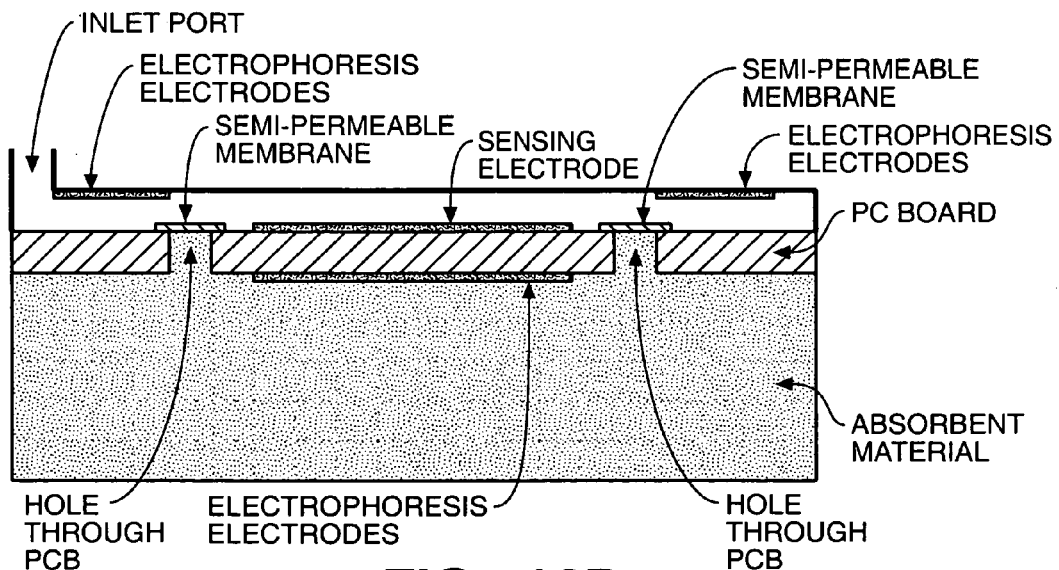
FIG._16D

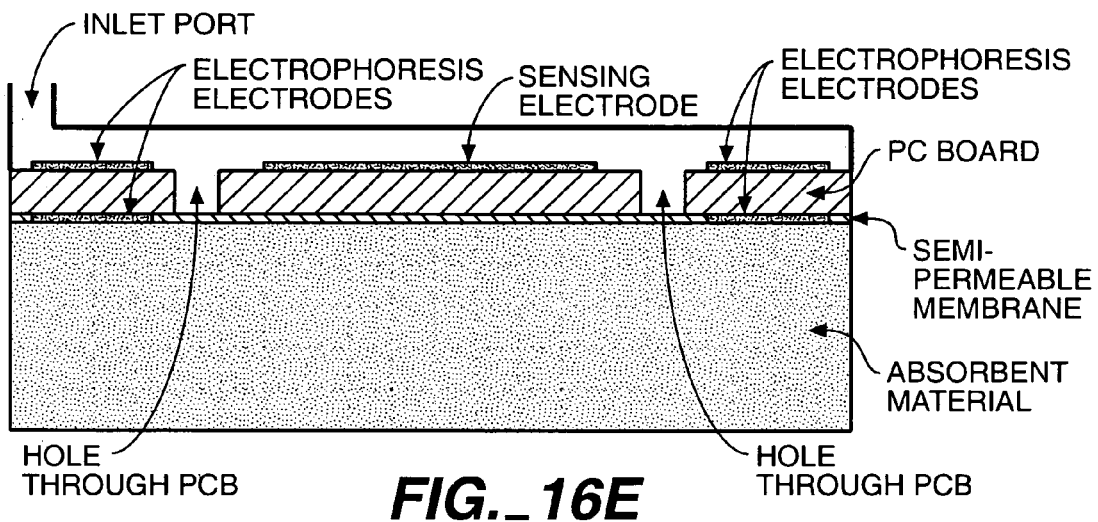
FIG._16E
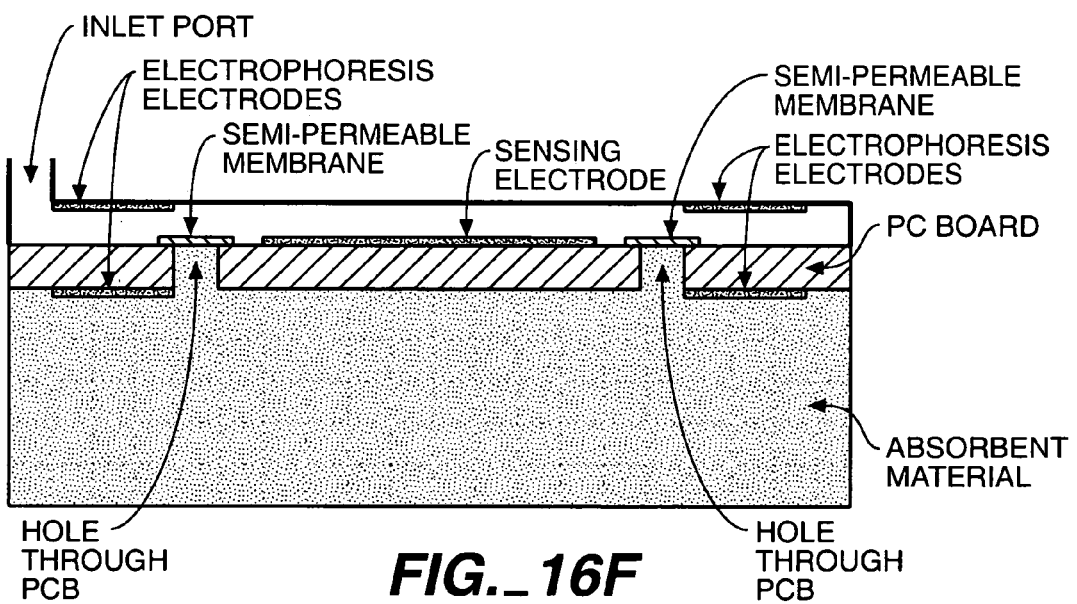
FIG._16F

BINDING ACCELERATION TECHNIQUES FOR THE DETECTION OF ANALYTES

This application is a continuing application of U.S. Ser. No. 60/171,981, filed Dec. 23, 1999; Ser. No. 09/440,371, filed Nov. 12, 1999, abandoned; Ser. No. 09/338,726, filed Jun. 23, 1999, now U.S. Pat. No. 6,264,825; Ser. No. 09/134,058 filed Aug. 14, 1998, now U.S. Pat. No. 6,290,839 and Ser. No. 60/090,389, filed Jun. 23, 1998, all of which are expressly incorporated by reference.

FIELD OF THE INVENTION

The invention relates to compositions and methods useful in the acceleration of binding of target analytes to capture ligands on surfaces. Detection proceeds through the use of an electron transfer moiety (ETM) that is associated with the target analyte, either directly or indirectly, to allow electronic detection of the ETM.

BACKGROUND OF THE INVENTION

There are a number of assays and sensors for the detection of the presence and/or concentration of specific substances in fluids and gases. Many of these rely on specific ligand/antiligand reactions as the mechanism of detection. That is, pairs of substances (i.e. the binding pairs or ligand/antiligands) are known to bind to each other, while binding little or not at all to other substances. This has been the focus of a number of techniques that utilize these binding pairs for the detection of the complexes. These generally are done by labelling one component of the complex in some way, so as to make the entire complex detectable, using, for example, radioisotopes, fluorescent and other optically active molecules, enzymes, etc.

Other assays rely on electronic signals for detection. Of particular interest are biosensors. At least two types of biosensors are known; enzyme-based or metabolic biosensors and binding or bioaffinity sensors. See for example U.S. Pat. Nos. 4,713,347; 5,192,507; 4,920,047; 3,873,267; and references disclosed therein. While some of these known sensors use alternating current (AC) techniques, these techniques are generally limited to the detection of differences in bulk (or dielectric) impedance.

The use of electrophoresis in microfluidic methods to facilitate the binding of biological molecules to their binding partners for subsequent detection is known; see for example U.S. Pat. Nos. 5,605,662 and 5,632,957, and references disclosed therein.

Similarly, electronic detection of nucleic acids using electrodes is also known; see for example U.S. Pat. Nos. 5,591,578; 5,824,473; 5,705,348; 5,780,234 and 5,770,369; U.S. Ser. No. 08/911,589; and WO 98/20162; PCT/US98/12430; PCT/US98/12082; PCT/US99/10104; PCT/US99/01705, and PCT/US99/01703.

One of the significant hurdles in biosensor applications is the rate at which the target analyte binds to the surface for detection and the affinity for the surface. There are a number of techniques that have been developed in nucleic acid applications to either accelerate the rate of binding, or to concentrate the sample at the detection surface. These include precipitation of nucleic acids (see EP 0 229 442 A1, including the addition of detergents (see Pontius et al., PNAS USA 88:8237 (1991)); partitioning of nucleic acids in liquid two phase systems (see Albertsson et al., Biochimica et Biophysica Acta 103:112 (1965), Kohne et al., Biochem. 16(24):5329 (1977), and Müller, Partitioning of Nucleic Acids, Ch. 7 in Partitioning in Aqueous Two-Phase Systems, Academic Press, 1985)), as well as partitioning in the presence of macroligands (see Müller et al., Anal. Biochem. 118:269 (1981)); and the addition of nucleic acid binding proteins (see Pontius et al., PNAS USA 87:8403 (1990) and U.S. Pat. No. 5,015,569), all of which are expressly incorporated by reference. In addition, partitioning systems for some proteins have also been developed, see Gineitis et al., Anal. Biochem. 139:400 (1984), also incorporated by reference.

However, there is a need for a system that combines acceleration of binding of target analytes, including nucleic acids, to a detection electrode for subsequent electronic detection.

SUMMARY OF THE INVENTION

In accordance with the objects outlined above, the present invention provides compositions comprising a substrate comprising a first surface comprising an array of detection electrodes each comprising a covalently attached capture ligand and at least a first electrophoresis electrode. The substrate also comprises a second surface comprising at least a second electrophoresis electrode and at least one channel connecting the first and second surface. The channels may comprise permeation layer materials or membranes as outlined herein.

In a further aspect, the present invention provides compositions comprising a detection chamber comprising a substrate comprising a first surface comprising an array of detection electrodes each comprising a covalently attached capture ligand. The surface also comprises a second surface and at least one channel connecting the first and second surface. The detection chamber also comprises an absorbent material in contact with the second surface. Again, the channels may comprise permeation layer materials or membranes as outlined herein.

In an additional aspect, the present invention provides methods of detecting a target analyte in a sample comprising concentrating the target analyte in a detection chamber as above, and binding the target analyte to the capture ligand to form an assay complex. The assay complex further comprises at least one electron transfer moiety (ETM). The method comprises detecting the presence of the ETM using the detection electrode.

In a further aspect, the present invention provides methods of detecting a target analyte in a sample. The methods comprise concentrating the target analyte in a detection chamber comprising a detection electrode comprising a covalently attached capture ligand. The target analyte is bound to the capture ligand to form an assay complex comprising at least one electron transfer moiety (ETM). The presence of the ETM is then detected using the detection electrode.

In a further aspect, the concentration step comprises placing the sample in an electric field between at least a first electrode and at least a second electrode sufficient to cause electrophoretic transport of the sample to the detection electrode.

In an additional aspect, the concentration step comprises including at least one volume exclusion agent in the detection chamber.

In a further aspect, the concentration step comprises comprises precipitating the target analyte.

In an additional aspect, the concentration step comprises including at least two reagents that form two separable solution phases, such that the target analyte concentrates in one of the phases.

In a further aspect, the concentration step comprises binding the target analyte to a shuttle particle.

In an additional aspect, the invention provides methods of detecting target analytes comprising flowing the sample past a detection electrode comprising a covalently attached capture ligand under conditions that result in the formation of an assay complex. As above, the assay complex further comprises at least one electron transfer moiety (ETM), and the presence of the ETM is detected using said detection electrode.

In a further aspect, the methods are for the detection of target nucleic acids and include the use of hybridization accelerators. The assay complex is formed in the presence of a hybridization accelerator, that may be a nucleic acid binding protein or a polyvalent ion.

In an additional aspect, the invention provides methods of detecting a target analyte in a sample comprising adding the sample to a detection electrode comprising a covalently attached capture ligand under conditions that result in the formation of an assay complex. The conditions include the presence of mixing particles.

In a further aspect, the invention provides substrates comprising a plurality of gold electrodes. Each gold electrode comprises a self-assembled monolayer, a capture ligand, and an interconnect such that each electrode is independently addressable. Preferred substrates include printed circuit board materials such as fiberglass.

In an additional aspect, the invention provides methods of making a substrate comprising a plurality of gold electrodes. The methods comprise coating an adhesion metal onto a fiberglass substrate, and coating gold onto the adhesion metal. A pattern is then formed using lithography, and the pattern comprises the plurality of electrodes and associated interconnects. The methods optionally include adding a self-assembled monolayer (SAM) to each electrode.

In an additional aspect, the invention provides methods of making a substrate comprising a plurality of gold electrodes. The methods comprise coating an adhesion metal onto a substrate, and coating gold onto the adhesion metal. A pattern is then formed using lithography, and the pattern comprises the plurality of electrodes and associated interconnects. The methods further include adding a self-assembled monolayer (SAM) to each electrode.

BRIEF DESCRIPTION OF THE DRAWINGS

FIGS. 1A, 1B, 1C, 1D, 1E and 1F depict several representative configurations of the use of two sets of electrodes, an electrophoresis set and a detection set. In FIGS. 1A and 1B, a substrate 30 has a first electrophoresis electrode 10 with detection electrodes 20 either on top or embedded in but electrically isolated from the electrophoresis electrode. There is a sample receiving area 40 as well. The counter electrode for the electrophoresis and detection electrodes are not shown. FIG. 1C represents a side view of FIG. 1A, with the addition of the counter electrophoresis electrode 50 and optionally the counter detection electrode 60. A permeation layer 25 is also shown. As will be appreciated by those in the art, these counter electrodes may be the same electrode, if they are used sequentially. FIGS. 1D, 1E and 1F depicts the use of individual electrophoresis electrodes. FIG. 1E is a side view of 1D. FIG. 1F shows the configuration for sequentially moving a sample from one detection electrode to another, as is more fully described below.

FIG. 2 depicts the use of multidimensional arrays of electrophoresis electrodes for both spatial targeting of the sample as well as "mixing" to increase binding kinetics. FIG. 2 shows electrophoresis electrodes 10, 11, 12, 13, 14, 15, 16, and 17 and detection electrodes 20, 21, 22, and 23. Electrophoresis voltage applied as between electrophoresis electrodes 10 and 15 and, at the same time, electrophoresis electrodes 12 and 17, can drive the target analyte to detector electrode 20.

FIGS. 3A, 3B and 3C depict three preferred embodiments for attaching a target sequence to the electrode. FIG. 3A depicts a target sequence 120 hybridized to a capture probe 100 linked via an attachment linker 106, which as outlined herein may be either a conductive oligomer or an insulator. The electrode 105 comprises a monolayer of passivation agent 107, which can comprise conductive oligomers (herein depicted as 108) and/or insulators (herein depicted as 109). As for all the embodiments depicted in the figures, n is an integer of at least 1, although as will be appreciated by those in the art, the system may not utilize a capture probe at all (i.e. n is zero), although this is generally not preferred. The upper limit of n will depend on the length of the target sequence and the required sensitivity. FIG. 3B depicts the use of a single capture extender probe 110 with a first portion 111 that will hybridize to a first portion of the target sequence 120 and a second portion 112 that will hybridize to the capture probe 100. FIG. 3C depicts the use of two capture extender probes 110 and 130. The first capture extender probe 110 has a first portion 111 that will hybridize to a first portion of the target sequence 120 and a second portion 112 that will hybridize to a first portion 102 of the capture probe 100. The second capture extender probe 130 has a first portion 132 that will hybridize to a second portion of the target sequence 120 and a second portion 131 that will hybridize to a second portion 101 of the capture probe 100. As will be appreciated by those in the art, any of these attachment configurations may be used with the embodiments of FIGS. 4A, 4B, 4C, 4D, 5A, 5B, 5C, 5D, 5E, 5F, 5G, 5H, 6A, 6B, 6C, 6D, 6E, 6F, 6G, and 6H.

FIGS. 4A, 4B, 4C and 4D depict several possible mechanism-1 systems. FIGS. 4A, 4B and 4C depict several possible nucleic acid systems. In FIG. 4A, a detection probe 140 (which also serves as a capture probe) is attached to electrode 105 via a conductive oligomer 108. The electrode 105 further comprises a monolayer of passivation agents 107. The target sequence 120 hybridizes to the detection probe 140, and an ETM 135 is attached (either covalently to one or other of the target sequence or the detection probe or noncovalently, i.e., as a hybridization indicator). In FIG. 4B, a FIG. 4A attachment to the electrode is used, with a capture probe 100 attached to the electrode 105 using an attachment linker 106, which can be either an insulator or a conductive oligomer. The target sequence 120 is hybridized to the capture probe, and a label probe 145, comprising a first portion 141 that hybridizes to a portion of the target sequence 120, and a recruitment linker 142 that hybridizes to a detection probe 140 which is attached to the electrode via a conductive oligomer 108. FIG. 4C is similar, except a first capture extender probe 110 is shown, and an amplifier probe 150, comprising a first portion 151 that will hybridize to a second portion of the target sequence 120 and a second portion (amplification sequence) 152 that will hybridize to a first portion 141 of the label probe 145. A second portion 142 of the label probe 145 hybridizes to the detection probe 140, with at least one ETM 135 present. FIG. 4C utilizes a FIG.

4B attachment to the electrode. FIG. 4D depicts a non-nucleic target analyte 165 bound to a capture binding ligand 160, attached to the electrode 105 via an attachment linker 106. A solution binding ligand 170 also binds to the target analyte and comprises a recruitment linker 171 comprising nucleic acids that will hybridize to the detection probe 140 with at least one ETM present.

FIGS. 5A, 5B, 5C, 5D, 5E, 5F and 5G depict some of the nucleic acid mechanism-2 embodiments of the invention. All of the monolayers depicted herein show the presence of both conductive oligomers 108 and insulators 107 in roughly a 1:1 ratio, although as discussed herein, a variety of different ratios may be used, or the insulator may be completely absent. In addition, as will be appreciated by those in the art, any one of these structures may be repeated for a particular target sequence; that is, for long target sequences, there may be multiple assay complexes formed. Additionally, any of the electrode-attachment embodiments of FIG. 3 may be used in any of these systems.

FIGS. 5A, 5B and 5D have the target sequence 120 containing the ETMs 135; as discussed herein, these may be added enzymatically, for example during a PCR reaction using nucleotides modified with ETMs, resulting in essentially random incorporation throughout the target sequence, or added to the terminus of the target sequence. FIG. 5D depicts the use of two different capture probes 100 and 100', that hybridize to different portions of the target sequence 120. As will be appreciated by those in the art, the 5'–3' orientation of the two capture probes in this embodiment is different.

FIG. 5C depicts the use of label probes 145 that hybridize directly to the target sequence 120. FIG. 5C shows the use of a label probe 145, comprising a first portion 141 that hybridizes to a portion of the target sequence 120, a second portion 142 comprising ETMs 135.

FIGS. 5E, 5F and 5G depict systems utilizing label probes 145 that do not hybridize directly to the target, but rather to amplifier probes that are directly (FIG. 5E) or indirectly (FIGS. 5F and 5G) hybridized to the target sequence. FIG. 5E utilizes an amplifier probe 150 that has a first portion 151 that hybridizes to the first portion 141 of the label probe. FIG. 5F is similar, except that a first label extender probe 160 is used, comprising a first portion 151 of amplifier probe 150. A second portion 152 of the amplifier probe 150 hybridizes to a first portion 141 of the label probe 140, which also comprises a recruitment linker 142 comprising ETMs 135. FIG. 5G adds a second label extender probe 170, with a first portion 171 that hybridizes to a portion of the target sequence 120 and a second portion 172 that hybridizes to a portion 153 of the amplifier probe 150.

FIG. 5H depicts a system that utilizes multiple label probes. The first portion 141 of the label probe 140 can hybridize to all or part of the recruitment linker 142.

FIGS. 6A–6H depict some of the possible non-nucleic acid mechanism-2 embodiments. FIG. 6A utilizes a capture binding ligand 200 linked to the electrode 105 by an attachment linker 106. Target analyte 205 binds to the capture binding ligand 200 and to a solution binding ligand 210 with a recruitment linker 220 comprising ETMs 135. FIG. 6B depicts a similar case, except that the capture binding ligand 200 is attached to the surface using a second binding partner interaction, for example a nucleic acid; a portion 201 of the capture binding ligand will bind or hybridize to a capture probe 100 on the surface. FIG. 6C also utilizes a second binding interaction, for example a nucleic acid interaction, to amplify the signal. In this case, the solution binding ligand 210 comprises a first portion 220 that will bind or hybridize to a first portion 231 of a label probe 230. The label probe 230 also comprises a second portion 232 that is a recruitment linker. FIG. 6D depicts an embodiment similar to 6A, with the use of a second solution binding ligand 240. FIG. 6E depicts the case where more than one capture binding ligand (200 and 200') is used. FIG. 6F shows a conformation wherein the addition of target alters the conformation of the binding ligands, causing the recruitment linker 220 to be placed near the monolayer surface. FIG. 6G shows the use of the present invention in candidate bioactive agent screening, wherein the addition of a drug candidate to target causes the solution binding ligand to dissociate, causing a loss of signal. In addition, the solution binding ligand may be added to another surface and be bound, as is generally depicted in FIG. 6H for enzymes. FIG. 6H depicts the use of an enzyme to cleave a substrate comprising a recruitment linker, causing a loss of signal. The cleaved piece may also be added to an additional electrode, causing an increase in signal, using either a mechanism-1 or a mechanism-2 system.

FIGS. 7A, 7B, 7C, 7D and 7E depict different possible configurations of label probes and attachments of ETMs. In FIGS. 7A–C, the recruitment linker is nucleic acid; in FIGS. 7D and E, it is not. A=nucleoside replacement; B=attachment to a base; C=attachment to a ribose; D attachment to a phosphate; E=metallocene polymer (although as described herein, this can be a polymer of other ETMs as well), attached to a base, ribose or phosphate (or other backbone analogs); F=dendrimer structure, attached via a base, ribose or phosphate (or other backbone analogs); G attachment via a "branching" structure, through base, ribose or phosphate (or other backbone analogs); H=attachment of metallocene (or other ETM) polymers; I=attachment via a dendrimer structure; J=attachment using standard linkers.

FIGS. 8A and 8B depict a schematic of an alternate method of adding large numbers of ETMs simultaneously to a nucleic acid using a "branch" point phosphoramidite, as is known in the art. As will be appreciated by those in the art, each end point can contain any number of ETMs.

FIGS. 9A, 9B and 9C depict a schematic of the synthesis of simultaneous incorporation of multiple ETMs into a nucleic acid, using a "branch" point nucleoside.

FIG. 10 depicts the synthesis of a "branch" point (in this case an adenosine), to allow the addition of ETM polymers.

FIG. 11 depicts the use of an activated carboxylate for the addition of a nucleic acid functionalized with a primary amine to a pre-formed SAM.

FIG. 12 depicts a representative hairpin structure. 500 is a target binding sequence, 510 is a loop sequence, 520 is a self-complementary region, 530 is substantially complementary to a detection probe, and 535 is the "sticky end", that is, a portion that does not hybridize to any other portion of the probe, that contains the ETMs 135.

FIGS. 13A, 13B, 13C and 13D depict some embodiments of the invention.

FIG. 14 depicts the results of the experimental example.

FIGS. 15A, 15B, 15C, 15D, 15E, 15F and 15G depict several possible configurations of two electrode systems. In side view FIG. 15A, a substrate 30 placed on electrophoresis electrode 10 containing detection electrodes 20. The substrate 30 has holes or channels in it. As for all the channels depicted herein, the channel may be optionally filled with permeation layer material 25; alternatively, a membrane such as a dialysis membrane may be used at either end of the channel. The permeation layer material, such as agarose, acrylamide, etc., allows the passage of ions for the electrophoresis but preferably prevents sample components, such as target analytes, from entering the permeation layer. However, as will be appreciated by those in the art, these channels could be open, and thus filled with buffer. The counterelectrode 50 can be placed anywhere. By setting up the electric field between the electrophoresis electrode 10 and the counterelectrode 50, the sample passes in the vicinity of the detection electrode. FIG. 15B shows a similar setup, but the electrophoresis electrode 10 is not in direct contact with the permeation layer; rather, an ionic conducting material 27 is used; preferred embodiments utilize buffer. FIG. 15C depicts an "asymmetrical" configuration, wherein the counterelectrode 50 is on one side of the detection electrode array and the channel is on the other. FIG. 15D is similar but "symmetrical". FIG. 15E uses two sets of electrophoresis electrodes; this allows a first electrophoresis step using electrodes 51 and 11, which can be run for some period of time, followed by a second electrophoresis step using electrodes 52 and 12. FIGS. 15F and 15G depict a top view of a substrate 30; the other electrophoresis electrode is on the other side of the substrate and is not shown. In this embodiment, the detection electrode(s) 20 surround a channel, optionally filled with a permeation material 25. Thus, FIG. 15F has one channel, and the detection electrodes are distributed around the channel. FIG. 15G has each pad with a channel in it.

FIGS. 16A, 16B, 16C depicts systems, similar to the FIG. 15 systems, wherein rather than use electrophoresis, hybridization acceleration is accomplished by using an absorbent material, similar to a volume exclusion agent, or combinations of electrophoresis and an absorbent material. In FIG. 16A, the introduction of the sample into the chamber 40 results in the liquid being drawn through a channel (optionally filled with a permeation layer), into a chamber comprising adsorbent material 500. FIG. 16B shows an alternate configuration wherein the size exclusion partition (e.g. the semi-permeable membrane) is on the surface of the substrate (e.g. the PC board). FIGS. 16C, 16D, 16E and 16F depict a variety of configurations combining the use of an absorbent material and electrophoresis. As will be appreciated by those in the art, this system may also be used with other hybridization acceleration techniques.

DETAILED DESCRIPTION OF THE INVENTION

Figure 5D:
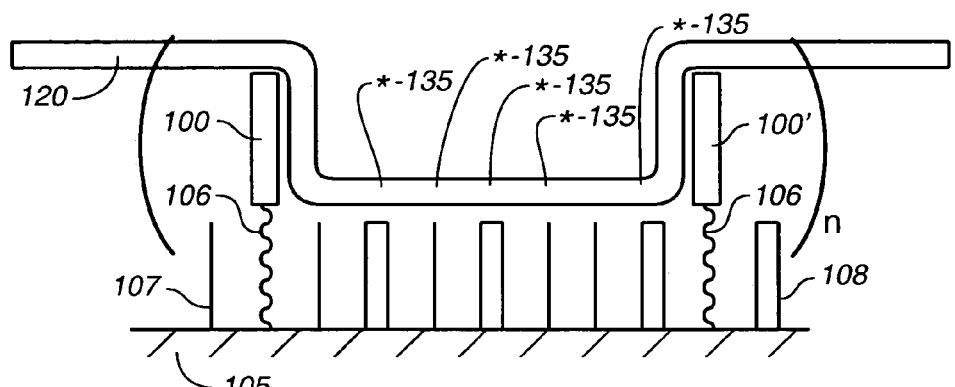

The present invention is directed to methods and compositions useful in the detection of biological target analyte species such as nucleic acids and proteins based on electrochemical detection on an electrode. As is known in the art, one of the significant hurdles of biosensors, particularly biosensors for the detection of nucleic acids, is the rate of binding (i.e. hybridization in the case of nucleic acids) of the solution-based target to the surface-bound capture ligand. See for example Gingeras et al., Nucl. Acid Res. 13:5373 (1987), hereby incorporated by reference in its entirety. This can be affected in a number of ways, including (1) concentrating the target analyte near the surface, effectively resulting in a larger amount of the target analyte binding to the capture ligand; (2) configuring the system to allow for good flow or "mixing", again allowing a larger amount of the target analyte to bind to the capture ligand; or, (3) in the case of nucleic acids, using hybridization accelerators, that actually increase the rate of hybridization in assay complexes comprising the target sequence and the capture probes. All three of these are sometimes referred to herein as binding or hybridization acceleration, with the understanding that some of these techniques don't actually increase the rate constant of binding, they increase the amount of target analyte bound per unit time by increasing the concentration or by improving mass transport. Thus, the present invention is directed to the use of compositions and methods to increase the number of target molecules bound to the surface within a given unit of time. While a number of the techniques outlined herein are generally exemplified by nucleic acids, one of skill in the art will recognize the applicability of all the techniques to other target analytes including proteins.

Thus, the present invention describes a number of techniques that can be used to accelerate the rate of assay complex formation or increase the number of assay complexes in a given period of time, wherein the target analyte becomes associated with a capture ligand on the electrode surface. These techniques include, but are not limited to, electrophoretic transport; the use of volume exclusion agents; the use of nucleic acid binding proteins (in the case of nucleic acid target analytes); the use of polyvalent ions; precipitation agents; partitioning; adjusting the phase compatability; structuring flow parameters; the use of microparticles (including both magnetic and non-magnetic particles) as either "shuttles" or "mixers"; the use of temperature gradients; the use of filters; and combinations thereof.

Accordingly, the present invention provides methods of detecting a target analyte in sample solutions. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples (i.e. in the case of nucleic acids, the sample may be the products of an amplification reaction, including both target and signal amplification as is generally described in PCT/US99/01705, such as PCR or SDA amplification reactions); purified samples, such as purified genomic DNA, RNA, proteins, etc.; raw samples (bacteria, virus, genomic DNA, etc.; As will be appreciated by those in the art, virtually any experimental manipulation may have been done on the sample.

The methods are directed to the detection of target analytes. By "target analytes" or grammatical equivalents herein is meant any molecule or compound to be detected. As outlined below, target analytes preferably bind to binding ligands, as is more fully described below. As will be appreciated by those in the art, a large number of analytes may be detected using the present methods; basically, any target analyte for which a binding ligand, described below, may be made may be detected using the methods of the invention.

When electrophoresis is used, as is more fully outlined below, the target analyte is preferably charged, i.e. it carries a net charge under the experimental conditions, such that it is able to be transported electrophoretically in an electric field. However, non-charged target analytes may be utilized if a charged binding partner or binding ligand is associated with the target analyte. For example, as more fully described below, in the case of some target analytes, for example proteins, that carry little or no net charge, soluble binding ligands can be used to bind to the target analytes that additionally contain ETMs and/or charged species; in some embodiments, the ETM may be charged, and thus facilitate both electrophoresis and detection.

Suitable analytes include organic and inorganic molecules, including biomolecules. In a preferred embodiment, the analyte may be an environmental pollutant (including pesticides, insecticides, toxins, etc.); a chemical (including solvents, organic materials, etc.); therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including procaryotic (such as pathogenic bacteria) and eucaryotic cells, including mammalian tumor cells); viruses (including retroviruses, herpesviruses, adenoviruses, lentiviruses, etc.); and spores; etc. Particularly preferred analytes are environmental pollutants; nucleic acids; proteins (including enzymes, antibodies, antigens, growth factors, cytokines, etc); therapeutic and abused drugs; cells; and viruses.

Particularly preferred target analytes include proteins and nucleic acids. "Protein" as used herein includes proteins, polypeptides, and peptides. The protein may be made up of naturally occurring amino acids and peptide bonds, or synthetic peptidomimetic structures. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids, Koshkin et al., J. Am. Chem. Soc. 120:13252–3 (1998); positive backbones (Denpcy et al., Proc. Natl. Acad. Sci. USA 92:6097 (1995); non-ionic backbones (U.S. Pat. Nos. 5,386, 023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Left. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169–176). Several nucleic acid analogs are described in Rawls, C & E News Jun. 2, 1997 page 35. All of these references are hereby expressly incorporated by reference.

These modifications of the ribose-phosphate backbone may be done to facilitate the addition of ETMs, or to increase the stability and half-life of such molecules in physiological environments.

As will be appreciated by those in the art, all of these nucleic acid analogs may find use in the present invention. In addition, mixtures of naturally occurring nucleic acids and analogs can be made; for example, at the site of conductive oligomer or ETM attachment, an analog structure may be used. Alternatively, mixtures of different nucleic acid analogs, and mixtures of naturally occuring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2–4° C. drop in Tm for an internal mismatch. With the non-ionic PNA backbone, the drop is closer to 7–9° C. This allows for better detection of mismatches. Similarly, due to their non-ionic nature, hybridization of the bases attached to these backbones is relatively insensitive to salt concentration.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occuring analog structures. Thus for example the individual units of a peptide nucleic acid, each containing a base, are referred to herein as a nucleoside.

In a preferred embodiment, the methods include concentrating the target analyte in the vicinity of a detection electrode. The description of the detection electrode compositions is described below. As will be appreciated by those in the art, the starting concentration of the target analyte in the sample can vary widely, depending on the type of sample used. In general, the starting concentration of the target analyte in the sample is relatively low, and preferred techniques utilize methods that allow the concentration of the target analyte in the vicinity of the detection electrode.

In general, "concentration" means that the effective diffusion distance a target analyte must travel to bind to the surface is reduced. In a preferred embodiment, the concentration at or near the detection electrode is higher than the concentration in the starting sample. This may be measured in a variety of ways, including directly, or indirectly as a function of binding acceleration. That is, in a preferred embodiment, concentration increases of at least two fold are preferred, with at least 5 fold being particularly preferred, and at least 10 fold increases being especially preferred. As will be appreciated by those in the art, the increase in concentration will depend on the starting sample size as well, and thus very large increases in concentration, e.g. 100-, 1000- and 10,000- (or higher) fold increases may be desirable. When the rate of hybridization is used as an indication of concentration, increases of at least two fold more target analyte binding to the detection electrode per unit time is preferred, with at least 5 fold being particularly preferred, and at least 10 fold increases being especially preferred; again, higher increases may be preferable in some embodiments.

As outlined herein, there are a variety of suitable concentration methods. In a preferred embodiment, the concentrating is done using electrophoresis. In general, the system is described as follows. A first electrode and a second electrode are used to generate an electric field to effect transport, generally electrophoretic transport, of the target analyte species increases its concentration at a detection electrode, which has a covalently attached capture binding ligand that will bind (either directly or indirectly) the target analyte. In this way, the kinetics of target analyte binding to its capture ligand are significantly increased, by both increasing the concentration of the target analyte in the medium surrounding the capture ligand and reducing the distance a given target analyte molecule must difuse to find a binding ligand.

The detection electrode may or may not be the same as the first electrode. That is, in one embodiment, the electrodes used to generate the electric fields that result in transport of the analytes to the surface are different from the electrodes used for detection; i.e. there are two sets of electrodes, although as will be appreciated by those in the art, the two sets may share electrodes, for example the counter electrode. In an additional embodiment, the electrodes used for electrophoretic transport and for detection are the same; i.e. there is only one set of electrodes. In some embodiments, the electrophoretic electrode which attracts the target analyte comprises a permeation layer that serves to limit access of the target analytes to the electrode surface and thus protects the analytes from electrochemical degradation.

This electrophoretic transport to the vicinity of the detection probe allows the concentration of the target analyte at or near the detection probe surface, which contains capture binding ligands that will bind the target analytes to form assay complexes. In some embodiments, the sequential or simultaneous use of a plurality of electrophoresis electrodes allows multidimensional electrophoresis, i.e. the solution may be targeted, "mixed" or "stirred" in the vicinity of the detection electrode, to further increase the kinetics of binding. As described below, the assay complex comprises an ETM, which is then detected using the detection electrode.

It should also be noted that a number of electrophoretic steps may be used; for example, the components of the system may be added sequentially, with an electrophoresis step after each addition to transport the reagents down to the detection electrode. Similarly, electrophoresis may be used to effect "washing" steps, wherein excess reagents (non-bound target molecules or non-bound extra binding ligand components, etc.) Or other components of the sample (e.g. noncomplimentary nucleic acids) are driven away from the detection electrode. Thus any combination of electrophoresis steps may be used. In addition, the time of the electrophoretic steps may be altered.

The methods and compositions of the invention can rely on either two sets of electrodes, wherein one set is used for electrophoresis and the second set is used for detection, or one set of electrodes that functions to effect both electrophoresis and detection, as is generally described below.

Samples containing target analytes are placed in an electric field between at least a first and at least a second electrophoresis electrode. By "electrode" herein is meant a composition, which, when connected to an electronic device, is able to sense a current or a potential and convert it to a signal. Alternatively an electrode can be defined as a composition which can apply a potential to and/or pass electrons to or from species in the solution. Thus, an electrode is an ETM as described below. Preferred electodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include gold, silicon, platinum, carbon and metal oxide electrodes, with gold being particularly preferred.

The electrodes described herein are depicted as a flat surface, which is only one of the possible conformations of the electrode and is for schematic purposes only. The conformation of the electrode will vary with the detection method used. For example, flat planar electrodes may be preferred for optical detection methods, or when arrays of nucleic acids are made, thus requiring addressable locations for both synthesis and detection. Alternatively, for single probe analysis, the electrode may be in the form of a tube, with the SAMs comprising conductive oligomers and nucleic acids bound to the inner surface. Electrode coils or mesh may be preferred in some embodiments as well. This allows a maximum of surface area containing the nucleic acids to be exposed to a small volume of sample.

As will be appreciated by those in the art, the electrodes are configured in a variety of ways. In a preferred embodiment, the electrodes can be interdigitated as is known in the art. In addition, the different electrodes (e.g. the detection electrodes and the electrophoresis electrodes) can be the same or different metals; for example, the electrophoresis electrodes can be platinum and the detection electrodes can be gold.

In addition, as is more fully outlined below, the detection electrode may be configured to maximize the contact the entire sample has with the electrode, or to allow mixing, etc.

In a preferred embodiment, one (or both) of the electrophoretic electrodes, or channels in the substrate, comprises a permeation layer, as is generally described in U.S. Pat. Nos. 5,632,957 and 5,605,662, both of which are expressly incorporated by reference in their entirety. This is particularly useful when the system is run at high voltages, i.e. where water hydrolysis occurs. The permeation layer serves as an intermediate diffusion layer, and generally has a pore limit property which inhibits or impedes the target analytes, reactants, etc. from physical contact with the electrode surface and thus protects against adverse electrochemical effects. The permeation layer may be formed of a variety of materials, including, but not limited to, carbon chain polymers, carbon-silicon chain polymers, carbon-phosphorus chain polymers, carbon-nitrogen chain polymers, silicon chain polymers, polymer alloys, layered polymer composites, interpenetrating polymer materials, ceramics, controlled porosity glasses, materials formed as sol-gels, materials formed as aero-gels, agarose, acrylamides, materials formed as hydro-gels, porous graphite, clays or zeolites. Particularly preferred are mesh-type polymers formed of acrylamide and cross-linkers, including, but not limited to, triethylene glycol diacrylate, tetraethylene glycol diacrylate and N,N'-methylene-bisacrylamide.

In a preferred embodiment, the electrophoresis electrodes and/or channels comprise materials that are not traditional permeation layer materials but rather are conductive materials, particularly electropolymerizable polymers. In this embodiment, the electrophoresis electrodes are fabricated by polymerizing a polymer onto the surface of the electrophoresis electrode. One advantage of these electropolymerizable materials is that the thickness of the polymerized material can be both controlled and varied; for example, a single monolayer of material can be made, or layers up to several microns thick can be made. In addition, it is possible to very specifically localize the polymer onto the surface of the electrophoresis electrode.

Suitable electropolymerizable monomers include, but are not limited to, pyrroles (to result in a polypyrrole layer; see Brajter-Toth, Anal Chem. 66:2458–2464 (1994), hereby incorporated by reference in its entirety), aniline (to result in a polyaniline layer), phenol (to result in a polyphenol layer), azulenes, pyrenes and carbazoles (see Hino et al., Synthetic Metals 64:259 (1994), hereby incorporated by reference in its entirety). A particularly preferred material is polypyrrole, as it has some interesting properties with respect to conductivity. Over oxidation of the pyrrole can convert the conductive polymer to an insulator that has molecular recognition characteristics.

In a preferred embodiment, either ion-partition membranes or sol-gel components can be used to shield the electrophoresis electrodes. See Anal. Chem., 72:1835 (2000), hereby expressly incorporated by reference. In this embodiment, the nucleic acids (or other target analytes) can actually enter the membrane or gel (e.g. they are trapped or collected). In addition, this may be followed by a buffer exchange step.

The electric field is generated between the first and second electrophoresis electrodes. The terms "first" and "second" are essentially interchangeable and not meant to confer any spatial or conformational distinctions, although in general, as used herein, the first electrode is generally the electrode spatially closest to the detection electrode (when two sets of electrodes are used), or alternatively, the first electrode is generally depicted as the detection electrode (when only one set of electrodes is used). As will be appreciated by those in the art, any number of possible electrophoresis electrode configurations can be used, as is generally depicted in FIGS. 1, 2 and 15. In general, there are two types of configurations: bulk electrophoresis and targeted electrophoresis.

In a preferred embodiment, a bulk electrophoresis configuration is used. That is, one set of electrophoresis electrodes are used, as is generally shown in FIGS. 1A, 1B and 1C. The first electrophoresis electrode (10 in FIG. 1) is generally larger than the detection electrodes and is arranged spatially such that the detection probes are within the electric field generated by the electrophoresis electrodes. Upon the application of a DC voltage between the electrodes, an electric field is generated such that electrophoretic transport of the charged target analytes to the vicinity of the detection probes is effected. While this does not necessarily directly place the target analytes on the detection probes, the decrease in effective diffusion distance and increase in the effective concentration at the detection surface significantly increases the kinetics of target analyte binding to the capture binding ligand on the surface of the detection probe, as diffusion needs to take place in essentially two dimensions, rather than three.

In a preferred embodiment, a targeted electrophoresis configuration is used, as is generally depicted in FIGS. 1D, 1E and 1F. In this embodiment, there are a plurality of electrophoresis electrodes that are used to specifically target the analyte to a specific detection electrode, most generally, but not always, in sets. This may be done in one of two basic ways. In a preferred embodiment, as generally depicted in FIG. 1F and components of which are described in U.S. Pat. No. 5,605,662, hereby expressly incorporated by reference, each detection electrode has an associated electrophoresis electrode. Thus, by either sequentially or simultaneously applying a voltage between sets of electrophoresis electrodes, target analytes may be moved from one detection electrode to another. Assuming for the moment a negatively charged target analyte such as nucleic acid, the system may be run as follows, using the FIG. 1F system. In one embodiment, an electric field is generated between anode 50 and electrophoresis electrode 10, which is acting as the cathode, to bring the anionic target analyte mixture down to both electrophoresis electrode 10 and thus detection electrode 20, wherein binding of a species of the target analyte mixture can occur. The electric field is then shut off, and a new electric field is applied between electrophoresis electrode 10, now acting as an anode, and electrophoresis electrode 11, acting as a cathode. This drives the non-bound anionic species from 10 to 11, wherein binding of a second species of target analyte can bind. The electric field is turned off, and a new field as between 11 (acting as the anode) and 12 (acting as the cathode) is generated, to move non-bound target analytes to a new detection electrode, etc. The advantage of this type of approach is that essentially the entire target analyte population is transported to each capture ligand, thus maximizing the number of target analytes that have an opportunity to bind to their capture ligands.

Alternatively, the electrophoresis at each pad can be run simultaneously, with an electric field generated between (assuming a negatively charged target analyte population) anode 50 and cathodes 10, 11, 12 and 13. This is faster, but results in (assuming four pads) only one quarter of the target analyte being "presented" to each detection electrode. This may or may not be desirable in different embodiments; for example, when speed rather than sensitivity is important.

In a preferred embodiment, a related but different type of targeted electrophoresis is done. In this embodiment, a plurality of sets of electrophoresis electrodes are positioned in a three dimensional way, to allow movement of the target analytes to different locations. For example, as shown in FIG. 2, the use of a three-dimensional array of electrophoresis electrodes allows localization of the sample solution to particular locations, i.e. individual detection electrodes or sets of detection electrodes. Thus, for example, with reference to FIG. 2, electrophoretic voltage applied between electrophoretic electrodes 10 and 15 and, at the same time, electrophoretic electrodes 12 and 17 can drive the target analyte to detector electrode 20.

Alternatively, in a preferred embodiment, a plurality of electrophoresis electrodes are used, not for specific targeting to a particular location, but rather to increase binding kinetics through "mixing" or "stirring" of the sample in the vicinity of the detection electrode with its associated capture ligand. For example, as shown in FIG. 2, an initial electrophoretic step may be done between electrophoretic electrode 18 and a non-depicted second electrophoretic electrode, to drive the target analytes to the detection probe surface, i.e. "bulk electrophoresis" as defined above. Then, voltages, either DC or AC voltages, including pulses of each, can be applied between the additional sets of electrophoresis electrodes, to transport the target analyte to increase both availability and binding kinetics of the target analytes to the capture binding ligands immobilized on the detection electrodes. Similarly, as shown in FIG. 15E, using two sets of electrophoresis electrodes at different times can drive the target analytes to the detection probe surface.

The strength of the applied electric field is determined by a number of factors, including, but not limited to, the desired time of electrophoresis, the size of the sample (i.e. the distance the target analyte must travel), the composition of the solution (i.e. the presence or absence of electroactive charge carriers and their redox potentials), the composition of the components (i.e. the stability of certain components of the invention to electrochemical potential), the presence or absence of electroactive charge carriers in solution, the size of the chamber, the charge of the target analyte, the size and location of the electrodes, the electrode material, etc.

In general, DC voltages are applied for the initial electrophoresis, with DC or AC pulses or fields applied for mixing, if applicable.

The strength of the applied field will depend in part on the other components of the system. For example, when only one set of electrodes is used and thiol linkages are used to attach the components of the system to the detection electrodes (i.e. the attachment of passivation agents and conductive oligomers to the detection electrode, as is more fully outlined below), the applied electrophoretic voltage is below the oxidation potential of the thiol compounds, i.e. generally less than 1 V. Alternatively, higher voltages can be used when thiol linkages are not used. Similarly, thiol linkages are acceptable at higher field strengths when two sets of electrodes are used, i.e. the detection electrodes containing sensitive chemistry are not exposed to high voltages.

Thus, in general, electrophoretic voltages range from 1 mV to about 2 V, although as will be appreciated by those in the art, the required voltage will depend on the desired time of running, the net charge on the analytes, the presence or absence of buffers, the position of the electrodes, etc. As is known in the art, the electrophoretic velocity is $\mu(d\phi/dx)$, wherein $\mu$ is the ionic mobility. For one set of electrode embodiments, the electrophoretic voltages range from about 50 mV to about 900 mV, with from about 100 mV to about 800 mV being preferred, and from about 250 mV to about 700 mV being especially preferred. For two set embodiments, the electrophoretic voltages range from about 100 mV to about 2V or higher, with from about 500 mV to about 1.5 V being preferred, and from about 1V to about 1.5 V being especially preferred. Of course, as will be appreciated by those in the art, these voltages can be positive or negative, depending on the charge of the analyte.

When low voltages are used, i.e. voltages less than 1.23 V (relative to a normal hydrogen electrode), the voltage at which water hydrolysis occurs, it is necessary to include a electroactive species in the solution, such that current can be transported from the electrode to the solution and an electric field can be generated throughout the solution. The type and concentration of the electroactive species will vary with the voltage, the length of required time for electrophoresis (which relates to the required distance, i.e. sample volume), etc. In a preferred embodiment, the redox potential of the electroactive species is higher than that of the ETM used for detection. For example, if a electroactive charge carrier with a redox potential of 300 mV is used and the ETM has a redox potential of 100 mV, electrophoresis can be done at 300 mV with subsequent detection being done at 100 mV, without a need to remove the electroactive species.

As will be appreciated by those in the art, a wide variety of suitable electroactive charge carriers can be used, including, but not limited to, compounds of iron, including aqueous $FeCl$, $Fe(CN)_6^{4-/3-}$, and ferrocene and its derivatives; complexes of ruthenium, including $Ru(NH_3)_5pyr$ and $Ru(NH_3)_5H_2O$; complexes of cobalt including $Co(NH_3)_6^{3+}$, $Co(bpy)_3^{3+}$ and $Co(tris)bpy^{3+}$); complexes of osmium including $Os(bpy)_3^{2+}$ and $Os(tris)bpy$ and derivatives; complexes of rhenium, including $Rh(NH_3)_4Cl_2$; and iodine $I_{3-}$. As is known in the art, some oxidation-reduction reactions produce solids (i.e. there are not a reversible couple). Generally, these species are not preferred, although in some instances they may be used when the detection electrode is the soluble reaction. Thus for example, a Ag/AgCl reaction may be used with nucleic acids, since the AgCl reaction occurs at the anode. The concentration of the redox molecule will vary, as will be appreciated by those in the art, with concentrations at or below saturation being useful. It should also be noted that in this embodiment, when an electroactive charge carrier is used, it may be necessary to mix or stir the system during electrophoresis.

It should be noted that electroactive charge carriers may be used in any system, particularly array-based systems, that utilize electrophoresis. For example, electroactive charge carriers may be used in electrophoretic array systems such as described in U.S. Pat. Nos. 5,532,129, 5,605,662, 5,565,322 and 5,632,957 and related applications, all of which are incorporated by reference.

The sample is placed in the electric field to effect electrophoretic transport to one or more detection electrodes. The composition of the detection electrode is as described above for the electrophoresis electrodes, with gold, silicon, carbon, platinum and metal oxide electrodes being particularly preferred.

In a preferred embodiment, the detection electrodes are formed on a substrate. In addition, the discussion herein is generally directed to the formation of gold electrodes, but as will be appreciated by those in the art, other electrodes can be used as well. The substrate can comprise a wide variety of materials, as will be appreciated by those in the art, with printed circuit board (PCB) materials being particularly preferred. Thus, in general, the suitable substrates include, but are not limited to, fiberglass, teflon, ceramics, glass, silicon, mica, plastic (including acrylics, polystyrene and copolymers of styrene and other materials, polypropylene, polyethylene, polybutylene, polycarbonate, polyurethanes, Teflon™, and derivatives thereof, etc.), GETEK (a blend of polypropylene oxide and fiberglass), etc.

In general, preferred materials include printed circuit board materials. Circuit board materials are those that comprise an insulating substrate that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" (e.g. all electrodes and interconnections in a plane) or "three dimensional" (wherein the electrodes are on one surface and the interconnects may go through the board to the other side) boards. Three dimensional systems frequently rely on the use of drilling or etching, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer.

In some embodiments, glass may not be preferred as a substrate.

Accordingly, in a preferred embodiment, the present invention provides biochips (sometimes referred to herein "chips") that comprise substrates comprising a plurality of electrodes, preferably gold electrodes. The number of electrodes is as outlined for arrays. Each electrode preferably comprises a self-assembled monolayer as outlined herein. In a preferred embodiment, one of the monolayer-forming species comprises a capture ligand as outlined herein. In addition, each electrode has an interconnection, that is attached to the electrode at one end and is ultimately attached to a device that can control the electrode. That is, each electrode is independently addressable.

The substrates can be part of a larger device comprising a detection chamber that exposes a given volume of sample to the detection electrode. Generally, the detection chamber ranges from about 1 nL to 1 ml, with about 10 μL to 500 μL being preferred. As will be appreciated by those in the art, depending on the experimental conditions and assay, smaller or larger volumes may be used.

In some embodiments, the detection chamber and electrode are part of a cartridge that can be placed into a device comprising electronic components (an AC/DC voltage source, an ammeter, a processor, a read-out display, temperature controller, light source, etc.). In this embodiment, the interconnections from each electrode are positioned such that upon insertion of the cartridge into the device, connections between the electrodes and the electronic components are established.

Detection electrodes on circuit board material (or other substrates) are generally prepared in a wide variety of ways. In general, high purity gold is used, and it may be deposited on a surface via vacuum deposition processes (sputtering and evaporation) or solution deposition (electroplating or electroless processes). When electroplating is done, the substrate must initially comprise a conductive material; fiberglass circuit boards are frequently provided with copper foil. Frequently, depending on the substrate, an adhesion layer between the substrate and the gold in order to insure good mechanical stability is used. Thus, preferred embodiments utilize a deposition layer of an adhesion metal such as chromium, titanium, titanium/tungsten, tantalum, nickel or palladium, which can be deposited as above for the gold. When electroplated metal (either the adhesion metal or the electrode metal) is used, grain refining additives, frequently referred to in the trade as brighteners, can optionally be added to alter surface deposition properties. Preferred brighteners are mixtures of organic and inorganic species, with cobalt and nickel being preferred.

In general, the adhesion layer is from about 100 Å thick to about 25 microns (1000 microinches). The If the adhesion metal is electrochemically active, the electrode metal must be coated at a thickness that prevents "bleed-through"; if the adhesion metal is not electrochemically active, the electrode metal may be thinner. Generally, the electrode metal (preferably gold) is deposited at thicknesses ranging from about 500 Å to about 5 microns (200 microinches), with from about 30 microinches to about 50 microinches being preferred. In general, the gold is deposited to make electrodes ranging in size from about 5 microns to about 5 mm in diameter, with about 100 to 250 microns being preferred. The detection electrodes thus formed are then preferably cleaned and SAMs added, as is discussed below.

Thus, the present invention provides methods of making a substrate comprising a plurality of gold electrodes. The methods first comprise coating an adhesion metal, such as nickel or palladium (optionally with brightener), onto the substrate. Electroplating is preferred. The electrode metal, preferably gold, is then coated (again, with electroplating preferred) onto the adhesion metal. Then the patterns of the device, comprising the electrodes and their associated interconnections are made using lithographic techniques, particularly photolithographic techniques as are known in the art, and wet chemical etching. Frequently, a non-conductive chemically resistive insulating material such as solder mask or plastic is laid down using these photolithographic techniques, leaving only the electrodes and a connection point to the leads exposed; the leads themselves are generally coated.

The methods continue with the addition of SAMs. In a preferred embodiment, drop deposition techniques are used to add the required chemistry, i.e. the monolayer forming species, one of which is preferably a capture ligand comprising species. Drop deposition techniques are well known for making "spot" arrays. This is done to add a different composition to each electrode, i.e. to make an array comprising different capture ligands. Alternatively, the SAM species may be identical for each electrode, and this may be accomplished using a drop deposition technique or the immersion of the entire substrate or a surface of the substrate into the solution.

In a preferred embodiment, the system is configured to maximize the flow of the sample past the detection electrodes. As is generally depicted in FIG. 15, there are a variety of ways to allow this. In a preferred embodiment, the detection electrodes are distributed on a substrate that has channels or pores within it (these may also be referred to herein as holes or vias). The electrophoresis electrodes are positioned on opposite sides of this substrate. The introduction of the electric field results in the sample being drawn through or past the detection electrode, thus resulting in better hybridization kinetics.

As will be appreciated by those in the art, the configuration of the electrophoresis electrodes may vary. In a preferred embodiment, the detection electrodes and at least one electrophoresis electrode are positioned on the first surface of the substrate, and at least a second electrophoresis electrode is on the second surface of the substrate (assuming a generally planar substrate; as will be appreciated by those in the art, other configurations are also possible). Alternatively, the surfaces of the detection chamber may comprise the electrophoresis electrodes; that is, it is possible to position these electrodes off the substrate but on different sides of the substrate. In addition, a plurality of electrophoresis electrodes may be used, as is generally outlined herein.

In a preferred embodiment, these channels are filled with a material that allows the passage of ions to effect electrophoresis, but does not allow the passage of the target analyte. For example, the channels may be filled with a permeation layer material as defined herein.

In a preferred embodiment, rather than utilize a gel-like material, a membrane is placed on one or both ends of the channel. This membrane preferably allows the movement of ions to effect the electrophoresis, but does not let target analytes through, thus concentrating the target analytes in the vicinity of the detection electrodes.

In a preferred embodiment, hybridization acceleration is accomplished using a combination of the configuration of the system and an absorbent material. In this embodiment, generally depicted in FIG. 16, the detection chamber has two subchambers, generally separated by a size exclusion partition such as a gel matrix or a membrane. One chamber comprises the sample introduction inlet port and comprises the detection electrode. The other chamber comprises an absorbent material, usually in the dry state, that can absorb the aqueous solution of the sample (although in some cases the sample may be in an organic phase and the absorbent material will absorb organic phase solutions).

Thus, in a preferred embodiment, a size exclusion partition is used. By "size exclusion partition" herein is meant a material that excludes components on the basis of their molecular weight. Thus, for example, gel matrices (such as are outlined herein in permeation layers, such as acrylamide, agarose, etc.) or size exclusion cutoff membranes such as are known in the art are used. In some embodiments, particularly when the target analyte has a large molecular weight as compared to other contaminating components of the system, the molecular weight cutoff of the membrane or gel may be chosen to also do a complexity reduction step. That is, when for example ribosomal RNA is the target analyte, size exclusion partitions that allow the passage of average mRNA may be used. Similarly, when the target comprises large genomic DNA, molecular weight cutoffs that allow the passage of mRNA and fragmented DNA can be used.

In this embodiment, upon introduction of the sample, the aqueous solution that contains the target analyte is drawn from the detection chamber comprising the detection electrode into the absorption chamber, while concentrating the target analyte in the detection chamber. Thus for example, an injection of 1 ml of sample into a cartridge comprising a 0.95 ml absorption chamber will concentrate the target analyte 20:1 in the detection chamber.

In a preferred embodiment, the detection chamber and absorption chamber are separated by holes or vias in the substrate comprising the electrodes, although in some embodiments it is possible to have the detection electrodes "on" the size exclusion partition.

In this embodiment, it may be desirable to adjust the volumes of each chamber in the cartridge to allow for facile absorption. That is, when the volume of the detection chamber is the same or less than the sample volume, the injection of sample into the chamber may not result in absorption when the absorbent material is in the dried, stored state. However, if the sample volume is slightly larger than the detection chamber volume, the injection of the sample into the partitioned chamber can force the "wetting" of the absorbent material, thus driving the reaction through capillary action. Thus, in a preferred embodiment, the detection chamber volume is slightly less than the sample volume, such that fluid is "forced" into the absorption chamber.

In addition, the use of a size exclusion partition also allows a hybridization acceleration based on sample volume. That is, by using a size exclusion partition such as a membrane or gel matrix, a large volume of sample may be introduced into the detection chamber, with the aqueous solution being forced through the size exclusion partition into the absorption chamber. Thus, for example, if the sample volume is 5 mls and the detection chamber volume is 1 ml and the absorption chamber is 4 mls, a 5 fold concentration of target analyte within the sample volume is achieved. As will be appreciated by those in the art, this may be done with or without an absorption material in the absorption chamber. What is important in this embodiment is that the size exclusion partition prevents the target analyte from leaving the vicinity of the detection electrode. Furthermore, in some embodiments, the volume of the sample chamber may be adjustable; that is, upon introduction of the sample, the sample chamber is large enough to hold the entire sample. However, as sample solution is "pulled" into the absorption chamber, the volume of the sample chamber decreases, for example through the use of a membrane or flexible seal. In this way, the concentrated target analyte is held in the vicinity of the detection electrode.

As will be appreciated by those in the art, the system can take on a number of configurations, as is generally depicted in FIG. 16.

In a preferred embodiment, the absorbent material may be used in conjunction with electrophoresis. That is, as generally depicted in FIG. 16, there are a number of configurations that may be used, including "mixing" configurations as outlined herein.

In addition, as depicted in FIG. 13B, the system may be configured to allow the sample to flow past a number of detection electrodes placed along the electrophoresis channel. That is, as outlined herein, the sample receiving chamber can be configured to allow as much sample as possible to contact the detection electrodes.

Similarly, when a two electrode system is used, a preferred embodiment utilizes a porous detection electrode positioned between the first and the second electrophoresis electrodes, such that the target must "go through" the detection electrode, and thus maximizes the contact of the target analyte and the detection electrode. For example, polycarbonate microporous membranes are gold sputter coated for electron microscope analysis. Alternatively, gold coated polyaniline can be used. Thus, gold electrodes with very uniform pore sizes, ranging from 0.01 to 20 um can be made. Similarly, silicon wafers with 10 um pores have been developed for use as a genosensor that enhance capture of the target sequence by 700 fold. By adjusting the flow rate, pad area, pore diameter, depth, and electrophoretic parameters, virtually 100 percent of the target analyte in the sample may be bound to the detection electrode.

It should also be noted that a number of electrophoretic steps may be used; for example, the components of the system may be added sequentially, with an electrophoresis step after each addition to transport the reagents down to the detection electrode. Similarly, electrophoresis may be used to effect "washing" steps, wherein excess reagents (non-bound target molecules or non-bound extra binding ligand components, etc.) are driven away from the detection electrode. Thus any combination of electrophoresis steps may be used. In addition, the time of the electrophoretic steps may be altered.

In addition, as is outlined herein, electrophoresis steps can be combined with other techniques to concentrate analytes at the detection electrode surface. For example, as is shown in FIG. 13, the system can be configured to allow flow of the sample past the detection electrode in one direction, coupled with electrophoretic flow in the opposite direction, thus effectively concentrating the target analyte while allowing other sample components (particularly uncharged components or components with a charge opposite to the analyte) to be "washed" away. In this embodiment, the strength of the electrophoretic field is adjusted based on the size and charge of the target, such that the target remains relatively immobilized at the detection electrode.

In addition, as will be appreciated by those in the art, it is also possible to configure the sample receiving chamber to maximize the hybridization acceleration. For example, the chamber can be configured such that all the sample is subjected to the electrophoresis field; this may be done in a wide variety of ways; for example, by using different geometries (triangular, etc.), by having the electrode coat one or more internal surfaces of the chamber, etc.

In a preferred embodiment, concentration of the target analyte is accomplished using at least one volume exclusion agent in the assay reagent mix. In this embodiment, the inclusion of a volume exclusion agent, which can absorb solvent and small molecules such as ions, but excludes larger molecules such as target analytes, concentrates the target analyte to smaller apparent volumes, and thus decreasing the effective diffusional volume that the target analyte experiences, thus increasing the likelihood of the target finding a capture ligand. As will be appreciated by those in the art, the volume exclusion agents may not necessarily concentrate the sample close to the detection electrode; rather, they decrease the effective diffusional volume that the target analyte experiences or resides within.

Thus, the methods of the invention include adding at least one volume exclusion agent to the array mixture. As will be appreciated by those in the art, this can be done at virtually any step of the assay, including premixture of the exclusion agent with the sample, prior to the addition of additional reagents (such as label probes, etc.), the addition of the exclusion agent with one or more other assay reagents, or after the addition of the assay reagents. Alternatively, the detection chamber may be precoated with a volume exclusion agent (for example agarose, sephadex, sepharose, polyacrylamide, etc.) that will swell in the presence of the sample. In some embodiments, a membrane impermeable to the target analyte may be used to separate the volume exclusion agent from the detection electrode can be used. Similarly, other components of the system may be coated with swellable volume exclusion agents, such as the magnetic particles described herein. In general, adding the agent with the other assay reagents is preferable. Once added, there is generally an incubation step as will be appreciated by those in the art.

Suitable volume exclusion agents are known in the art, and include, but are not limited to, dextran, dextran sulfate, chonchritin sulfate, polyethylene glycol, polysulfonate, heparin sulfate, hespan, high molecular weight nucleic acid, etc. See for example Amasino, Anal. Chem. 152:304 (1986); Wetmur, Biopolymers 14:2517 (1975); Renz et al., Nucl. Acid Res. 12:3435 (1984); Wahl et al., PNAS USA 75:3683 (1979); and Gingeras et al., Nucl. Acid Res. 15:5373 (1987), all of which are expressly incorporated by reference. In addition, as will be appreciated by those in the art, mixtures of these agents may also be done. It should be noted that while volume exclusion is a concentration step, but also that the exclusion agent may be considered a hybridization accelerator, as outlined below.

In a preferred embodiment, concentration of the target analyte is done by precipitating the target analyte. This is particularly effective for nucleic acids. As has been shown previously, precipitation of nucleic acids can increase the rate of hybridization by 50 to 100 fold; see EP 0 229 442 A1, hereby expressly incorporated by reference. As above, precipitation is a concentration step, but the precipitating agent may be considered a hybridization accelerator, as outlined below. In a preferred embodiment, conditions are selected that precipitate double stranded nucleic acid but not single stranded nucleic acid, as this provides a strong driving force and cuts down on non-specific losses.

Suitable nucleic acid precipitating agents include, but are not limited to, salts which contain at least one of the stronger salting out cation or anion groups (including the alkali metal salts and ammonium salts of $SO_4$, $PO_4$, Li and COOH); organic compounds that are miscible with the reaction solution and which have precipitating or salting out properties, including but not limited to, detergent (see Pontius et al., PNAS USA 88:8237 (1991), hereby incorporated by reference), dihydroxybenezene, Sarkosyl (N-laurosarconsine sodium salt), sodium dodecyl sulfate, sodium diisobutyl sulfosuccinate and sodium tetradecyl sulfate. Suitable concentrations of each agent are described in the incorporated references. It should be noted that in some applications as outlined below, detergents need not actually precipitate the nucleic acid but rather are added as hybridization accelerators.

In addition, as described in EP 0 229 442 A1, additional reagents may be added, including, but not limited to, EGTA, EDTA, SDS, SK, PK, EtOH, urea, guanidine HCl, glycogen and dilute amphyl. Furthermore, known concentrations of at least one nucleic acid denaturing agents such as alcohol may be added.

As above, the addition of the nucleic acid precipitating agent can be done at virtually any step of the assay, including premixture of the agent with the sample, prior to the addition of additional reagents (such as label probes, etc.), the addition of the agent with one or more other assay reagents, or after the addition of the assay reagents. In general, adding the agent with the other assay reagents is preferable. Again, once added, there is generally an incubation step as will be appreciated by those in the art.

In a preferred embodiment, the concentrating is done by including at least two reagents that form two separable solution phases, such that the target analyte concentrates in one of the phases or at the interface. As is known in the art, if a sample is subjected to two separable solution phases an analyte may be driven from one phase to another and therefore become concentrated in one phase, or, in some circumstances, concentration can occur at the interface between the two phases. See for example Albertsson et al., Biochimica et Biophysica Acta 103:1–12 (1965), Kohne et al., Biochem. 16(24):5329 (1977), Müller, Partitioning of Nucleic Acids, Ch. 7 in *Partitioning in Aqueous Two-Phase Systems*, Academic Press, 1985), and Müller et al., Anal. Biochem. 118:269 (1981), all of which are expressly incorporated by reference. Thus, by configuring the sample volume, the volume of each phase, the detection electrode chamber and the position of the detection electrode, good concentration at the electrode may be achieved. As shown in Müller, Partitioning of Nucleic Acids, Ch. 7 in *Partitioning in Aqueous Two-Phase Systems*, Academic Press, (1985) and Albertsson, supra, partitioning is effected by electrolyte composition, including both the ionic strength and the kinds of ions, polymer concentration, the size of the nucleic acids, the structure and/or complexity of the nucleic acids, and the presence or absence of certain ligands.

In a preferred embodiment, ligands can be included in the partitioning mixtures to effect partitioning. As shown in both Müller et al. references, the inclusion of ligands that bind to nucleic acids can effect partitioning. Thus for example the use of nucleic acid binding dyes covalently bound to heteroalkyl chains such as PEG can strongly raise the partition coefficients. See Müller et al., Anal. Biochem. 118:269 (1981), Müller et al., Anal. Biochem. 118:267 (1981); and Müller et al., Eur. J. Biochem. 128:231 (1982), all of which are expressly incorporated by reference.

In a preferred embodiment, the phenol emulsion reassociation technique (PERT) is done, as described in Kohne et al., supra. In this embodiment, phenol and water (or other aqueous solutions) are added in the right proportions and shaken or mixed, an emulsion forms. When the shaking stops, the emulsion breaks and two phases form. The addition of single stranded nucleic acid and salt to the aqueous phase results in the extremely fast formation of hybrids. As outlined in Kohne, supra, the rate of nucleic acid hybridization depends on (a) the presence of the emulsion; (b) the type and concentration of ions; (c) an appropriate temperature of incubation; (d) the proper pH; (e) the rate and manner of agitating the emulsion; (f) the amount of phenol present; (g) the fragment size of the nucleic acid; (h) the complexity of the nucleic acid; and (I) the concentration of the nucleic acid.

In addition, partitioning is also known for proteins; see Gineitis et al., Anal. Biochem. 139:400 (1984), hereby expressly incorporated by reference.

In a preferred embodiment, both volume exclusion and partitioning may be done simultaneously. For example, dextran (3–8%) and PEG (3.5 to 6%) can be mixed and form separate phases. Shifts in the ratios of cations or anions can transfer high molecular weight nucleic acids from one phase to another and induce duplex formation.

In a preferred embodiment, the concentration step is done using shuttle particles. In general, this technique may be described as follows. Shuttle particles that will either settle by gravity onto the detection electrode (for example when the detection electrode is at the "bottom" of the chamber), float (for example when the detection electrode is at the "top" of the chamber) or can be induced to associate with the detection electrode (for example through the use of magnetic particles) are used. These shuttle particles comprise binding ligands that will associate with the target analyte(s) in the assay solution, generally but not always non-specifically, and then shuttle the target analytes to the detection electrode, where they can be released to bind to the capture binding ligand (either directly or indirectly, as outlined below). As will be appreciated by those in the art, the shuttle binding ligands preferably interact less strongly with the target analytes than the components of the assay complex, i.e. the capture binding ligand. That is, the interaction with the shuttle particle must be weak enough to allow release of the target analytes for binding to the detection electrode.

In a preferred embodiment, the target analyte is a nucleic acid and the shuttle particles may be configured in a number of ways. In one system, the shuttle particles comprise generally short (i.e. 4 to 10, although depending on the temperature used, they may be longer) nucleic acid probes that can bind the target analytes. These may be either specific, i.e. contain short sequences specific to the target analyte(s) of interest, or non-specific, ie. random probes that will shuttle all the nucleic acid in the sample to the surface. The attachment of nucleic acids to particles is known; see for example U.S. Ser. No. 60/105,875 and materials by Chad Mirkin. Similarly, for non-nucleic acid targets, ligands with varying binding affinities can be used; for example, a weakly binding antibody to a protein target may be attached to the bead, and a stronger affinity antibody may serve as the capture ligand on the surface. Alternatively, solution changes may be used to drive the transfer from the bead to the surface.

Alternatively, for both nucleic acids and other types of analytes including proteins, the particles may be modified (for example by derivativization with amine moieties (such as lysine moieties) or carboxy groups) to contain a charge for the electrostatic interaction of the target and the particle.

In a preferred embodiment, again when the target analytes are nucleic acids, the shuttle particles may contain nucleic acid binding components, that bind to either single stranded or double stranded nucleic acids. For example, particles comprising intercalators are known; see U.S. Pat. No. 5,582,984, hereby incorporated by reference in its entirety. Similarly, particles comprising single-stranded or double-stranded binding proteins can be made. Once at the detection surface, the target analytes may be released using known techniques, including heat, pH changes, salt changes, etc. It should be noted that these particles may have use in sample preparation, as the particles can bind up all the target analyte, allowing the remaining sample to be washed away or removed, or the particles comprising the target analyte to be removed from the sample.

In a preferred embodiment, the surface of the electrode, or of the substrate as described herein, may be altered to increase binding and/or reduce the effective diffusional space for the target analyte. That is, reducing the diffusional space from three dimensions (the detection chamber) to two dimensions (the detection surface) will significantly increase the kinetics of binding. This reduction can be accomplished in several ways. For example, in a preferred embodiment, the terminal groups of the SAM may be modified to comprise electrostatic groups of opposite charge from the target analyte. Thus, the time that a particular target molecule associates with the surface is increased, and diffusion preferably occurs in two dimensions rather than three. This effectively removes the target analytes from the diffusion layer over the detection surface, thus forming a gradient that brings new target analytes down into the diffusion layer. Thus, for example, cation-terminated passivation agents may be used, such as $HS-CH_2-NR_3^+$. Alternatively, the entire substrate of the detection chamber (i.e. the areas around the individual electrodes) may be coated with weakly binding ligands, similar to the shuttle particles described herein, forming a "lawn" of binding ligands. For example, oligonucleotide probes, that will either specifically bind target sequences or are relatively short non-specific sequences, can be used on the surface. Upon association of a target sequence with these surface probes, diffusion via equilibrium binding and release will allow two dimensional diffusion rather than three dimensional diffusion. In this embodiment, what is important is that the interaction between the surface ligands and the target analytes is weaker than that of the capture ligands, such that binding to the capture ligands is preferred. This can be controlled in the case of nucleic acids using probe length; capture probes will generally be longer than surface probes. As will be appreciated by those in the art, these techniques may be done alone or in addition to any of the other acceleration techniques outlined herein.

In addition, as is more fully described below, particles may also be used as "mixing particles", that serve to stir the solution near the detection electrode and thus increase hybridization.

In a preferred embodiment, the binding acceleration is done by configuring the system to maximize the amount of target analyte that can bind to the detection electrode in a given time period. This may be done for example by flowing or exposing a large volume of sample containing the target analyte past the detection electrode such that the target analytes have a high probability of associating with the detection electrode.

Accordingly, in a preferred embodiment, the methods include flowing the sample containing the target analyte(s) past a detection electrode to form assay complexes. In this embodiment, the concentration of the target analyte occurs as a result of a large volume of sample being contacted with the detection electrode per unit time, and also decreases the binding times as compared to a stagnant sample. Thus, in a preferred embodiment, as outlined above for electrophoresis, the device comprising the detection electrode can be configured to have the sample flow past or through the detection electrode. Thus, a preferred embodiment utilizes a porous electrode such as a gold electrode, as outlined above, positioned in a sample flow channel. See for example WO95/11755, incorporated by reference. The sample may additionally be recirculated as necessary. Rotating disc electrodes are also preferred.

Thus, in a preferred embodiment, the detection electrode and surrounding area is configured to result in mixing of the sample, which can serve to disturb this diffusion layer and allow greater access to the surface. For example, in one embodiment, the detection electrode is placed in a narrow sample channel. Thus, essentially, the detection electrode is a band or zone around the perimeter of the channel. Again, as outlined above, recirculation can also occur.

In an alternative embodiment, the detection electrode is configured with respect to the chamber such that the flow of the sample past the electrode causes mixing or sample turbulence. For example, in one embodiment the detection electrode is "sunken" or "recessed" with respect to the chamber, such that the flow of the sample past the electrode causes mixing; see FIG. 13. This effect may be enhanced by including raised surfaces, sometimes referred to herein as "weirs", on the edges of the electrode (including sunken electrodes) that cause mixing.

In addition to or instead of any of the methods disclosed herein, a preferred embodiment utilizes particles as "mixing balls". By "particle" or "microparticle" or "nanoparticle" or "bead" or "microsphere" herein is meant microparticulate matter. As will be appreciated by those in the art, the particles can comprise a wide variety of materials depending on their use, including, but not limited to, cross-linked starch, dextrans, cellulose, proteins, organic polymers including styrene polymers including polystyrene and methylstyrene as well as other styrene co-polymers, plastics, glass, ceramics, acrylic polymers, magnetically responsive materials, colloids, thoria sol, carbon graphite, titanium dioxide, nylon, latex, and teflon may all be used. "*Microsphere Detection Guide*" from Bangs Laboratories, Fishers Ind. is a helpful guide. Preferred embodiments utilize magnetic particles as outlined below. In addition, in some instances, the mixing particle need not comprise microparticulate matter; for example, for gravity mixing (i.e. for mixing based on agitation of the device), any component with a density different from the sample can be used; air bubbles can be used for example as mixing particles.

In other embodiments, the mixing particles may be chosen to have a large dielectric constant such that the particles can be moved by the application of an electromagnetic field gradient as could be produced using focused light or a diverging radio frequency (rf) field. The particles could also, in some instances, comprising diamagnetic materials, Such particles would not be affected substantially by the application of a linear magnetic field but could be moved by the application of a non-linear magnetic field as might be applied using a non-linear magnet or using a large linear magnet combined with small ferro-magnetic or paramagnetic inclusions in the chamber.

The size of the particles will depend on their composition. The particles need not be spherical; irregular particles may be used. In addition, the particles may be porous, thus increasing the surface area of the particle available for attachment of moieties. In general, the size of the particles will vary with their composition; for example, magnetic particles are generally bigger than colloid particles. Thus, the particles have diameters ranging from 1–5 nm (colloids) to 200 µm (magnetic particles).

As will be appreciated by those in the art, the particles can be added at any point during the assay, including before, during or after the addition of the sample.

The particles help stir the sample to effect more target binding. This may be accomplished in a number of ways. For example, particles can be added to the detection chamber and the entire chamber or device agitated. In a preferred embodiment, magnetic microparticles such as are known in the art may be used. In a preferred embodiment, the first particle is a magnetic particle or a particle that can be induced to display magnetic properties. By "magnetic" herein is meant that the particle is attracted in a magnetic field, including ferromagnetic, paramagnetic, and diamagnetic. In this embodiment, the particles are preferably from about 0.001 to about 200 µm in diameter, with from about 0.05 to about 200 µm preferred, from about 0.1 to about 100 µm being particularly preferred, and from about 0.5 to about 10 µm being especially preferred.

In this embodiment, it may be preferred to vary the direction and/or strength of the magnetic field, for example using electromagnets positioned around the detection chamber to move the beads in a variety of directions. Thus, for example, the use of magnetic shuttle particles as both shuttle and mixing particles can be accomplished by multiple magnetic fields; one that brings the particles down to the detection electrode, and one that agitates the beads on the surface of the detection electrode. Alternatively, non-magnetic particles may be added to augment the flow-type mixing outlined above.

The size of the microparticles will vary as outlined herein. Microparticles of 4.5 um have been observed to rest in solution on a solid support, relatively unaffected by diffusion, where as in the same sample 1.0 um particles remain suspended away from the solid surface and appear to follow the constraints of diffusion. Thus, the larger particles may move freely within the diffusion layer when combined with flow, to convert laminar flow to turbulent flow.

In addition, the particles may be chemically altered, for example with volume exclusion agents or hybridization accelerators as outlined herein to combine the acceleration effects.

As will be appreciated by those in the art, the shuttle particles outlined above may also serve a dual function as mixing particles.

Thus, the present invention provides compositions comprising detection electrodes and mixing particles, and methods of detecting target analytes using the compositions.

In addition, as is known in the art, one of the rate-limiting steps for target capture on a surface is believed to be the diffusion of molecules across the boundary layer near the solid phase. This boundary layer does not appear to mix well even during flow of the sample. This boundary layer and its statistical depth is a function of the properties of the solvent, the solid and the solute. Thus, altering these parameters may serve to "shrink" the boundary layer the target analyte must pass to reach the surface. For example, adjusting the organic content of the solute may make the analyte more accessible to the surface. Other parameters that can effect this are viscosity, surface charge, target secondary and tertiary structure, and temperature.

In a preferred embodiment, when the target analyte is a nucleic acid, binding acceleration is done by using a hybridization accelerator. In this embodiment, the binding of the target analyte to the detection electrode is done in the presence of a hybridization accelerator. As outlined herein, there are a variety of hybridization accelerators that actually increase the rate of nucleic acid hybridization, including, but not limited to, nucleic acid binding proteins, salts, polyvalent ions and detergents.

In a preferred embodiment, the hybridization accelerator is a nucleic acid binding protein. As has been shown in the art, certain binding proteins increase the rate of hybridization of single stranded nucleic acids; see Pontius et al., PNAS USA 87:8403 (1990) and U.S. Pat. No. 5,015,569, both of which are incorporated by reference. Thus, for example, hnRNP (A1 hnRNP) and recA are all known to increase the annealling rate of double stranded nucleic acids. Other single stranded nucleic acid binding proteins and major and minor groove binding proteins may also be used. Suitable conditions are known or elucidated from the prior art.

In a preferred embodiment, the hybridization accelerator is a salt. As is known in the art, the inclusion of high concentrations of salt can increase the rate of hybridization; see EP 0 229 442 A1, hereby incorporated by reference. Generally, concentrations of salt up to roughly 2 M can increase the rate of hybridization. Suitable salts include, but are not limited to, sodium chloride, cesium chloride, sodium phosphate, sodium perchlorate, litium chloride, potassium chloride, sodium bromide, sodium sulfate and ammonium chloride.

In a preferred embodiment, the hybridization accelerator is a polyvalent ion. Ions of higher valence such as Mg++ can improve the affinity of nucleic acid strands via electrostatic interactions and thus accelerate hybridization. In addition, these polyvalent ions can potentially affect packaging on the surface; that is, as the density of nucleic acid on the surface increases, a negative charge accumulates that may inhibit subsequent binding of more nucleic acid. Thus, the inclusion of a polyvalent ion that can serve as a "salt bridge" may serve to increase hybridization. Mn++ can have a similar effect.

In addition, certain ions such as Mg++ have been shown to improve binding in RNA by another method. RNA forms loops aroung Mg++ ions and finds a stable secondary structure coordinating with Mg++. If Mg++ is removed the RNA changes to another structure which is also stable. However, the transition phase may be a period of enhanced accessibility for incoming probes. Thus, adding sequential rounds of Mg++ followed by EDTA or a similar chelator can cycle through this transition phase and enhance binding.

In a preferred embodiment, the hybridization accelerator is a detergent; see Pontius et al., PNAS USA 88:8237 (1991), hereby incorporated by reference. In this case, certain detergents can increase the rate of hybridization by as much as $10^4$ fold. Suitable detergents include, but are not limited to, cationic detergents including, but not limited to, dodecyltrimethylammonium bromide (DTAB) and cetyltrimethylammonium bromide (CTAB), and other variants of the quaternary amine tetramethylammonium bromide (TMAB).

All of the above methods are directed to increasing the amount of target analyte accessible for binding and detection on the detection electrode within a given period of time. The detection systems of the present invention are based on the incorporation of an electron transfer moiety (ETM) into an assay complex as the result of target analyte binding.

In general, there are two basic detection mechanisms. In a preferred embodiment, detection of an ETM is based on electron transfer through the stacked π-orbitals of double stranded nucleic acid. This basic mechanism is described in U.S. Pat. Nos. 5,591,578, 5,770,369, 5,705,348, and PCT US97/20014 and is termed "mechanism-1" herein. Briefly, previous work has shown that electron transfer can proceed rapidly through the stacked π-orbitals of double stranded nucleic acid, and significantly more slowly through single-stranded nucleic acid. Accordingly, this can serve as the basis of an assay. Thus, by adding ETMs (either covalently to one of the strands or non-covalently to the hybridization complex through the use of hybridization indicators, described below) to a nucleic acid that is attached to a detection electrode via a conductive oligomer, electron transfer between the ETM and the electrode, through the nucleic acid and conductive oligomer, may be detected. This general idea is depicted in FIG. 3.

This may be done where the target analyte is a nucleic acid; alternatively, a non-nucleic acid target analyte is used, with an optional capture binding ligand (to attach the target analyte to the detection electrode) and a soluble binding ligand that carries a nucleic acid "tail", that can then bind either directly or indirectly to a detection probe on the surface to effect detection. This general idea is depicted in FIG. 3C.

Alternatively, the ETM can be detected, not necessarily via electron transfer through nucleic acid, but rather can be directly detected using conductive oligomers; that is, the electrons from the ETMs need not travel through the stacked π orbitals in order to generate a signal. Instead, the presence of ETMs on the surface of a SAM, that comprises conductive oligomers, can be directly detected. This basic idea is termed "mechanism-2" herein. Thus, upon binding of a target analyte, a soluble binding ligand comprising an ETM is brought to the surface, and detection of the ETM can proceed. The role of the SAM comprising the conductive oligomers is to shield the electrode from solution components and reducing the amount of non-specific binding to the electrodes. Viewed differently, the role of the binding ligand is to provide specificity for a recruitment of ETMs to the surface, where they can be detected using conductive oligomers with electronically exposed termini. This general idea is shown in FIGS. 4, 5 and 6.

Thus, in either embodiment, as is more fully outlined below, an assay complex is formed that contains an ETM, which is then detected using the detection electrode.

The present system finds particular utility in array formats, i.e. wherein there is a matrix of addressable detection electrodes (herein generally referred to "pads", "addresses" or "micro-locations"). By "array" herein is meant a plurality of capture ligands in an array format; the size of the array will depend on the composition and end use of the array. Arrays containing from about 2 different capture ligands to many thousands can be made. Generally, the array will comprise from two to as many as 100,000 or more, depending on the size of the electrodes, as well as the end use of the array. Preferred ranges are from about 2 to about 10,000, with from about 5 to about 1000 being preferred, and from about 10 to about 100 being particularly preferred. In some embodiments, the compositions of the invention may not be in array format; that is, for some embodiments, compositions comprising a single capture ligand may be made as well. In addition, in some arrays, multiple substrates may be used, either of different or identical compositions. Thus for example, large arrays may comprise a plurality of smaller substrates.

The detection electrode comprises a self-assembled monolayer (SAM). By "monolayer" or "self-assembled monolayer" or "SAM" herein is meant a relatively ordered assembly of molecules spontaneously chemisorbed on a surface, in which the molecules have a preferred orientation relative to each other (e.g. are oriented approximately parallel to each other) and a preferred orientation relative to the surface (e.g. roughly perpendicular to it). Each of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer. The SAM may comprise conductive oligomers alone, or a mixture of conductive oligomers and insulators. As outlined herein, the efficiency of target analyte binding (for example, oligonucleotide hybridization) may increase when the analyte is at a distance from the electrode. Similarly, non-specific binding of biomolecules, including the target analytes, to an electrode is generally reduced when a monolayer is present. Thus, a monolayer facilitates the maintenance of the analyte away from the electrode surface. In addition, a monolayer serves to keep extraneous electroactive species away from the surface of the electrode. Thus, this layer helps to prevent electrical contact between the electrodes and the ETMs, or between the electrode and extraneous electroactive species within the solvent. Such contact can result in a direct "short circuit" or an indirect short circuit via charged species which may be present in the sample. Accordingly, in one embodiment, the monolayer is preferably tightly packed in a uniform layer on the electrode surface, such that a minimum of "holes" exist. In this embodiment, the monolayer thus serves as a physical barrier to block solvent accesibility to the electrode.

In a preferred embodiment, the monolayer comprises conductive oligomers. By "conductive oligomer" herein is meant a substantially conducting oligomer, preferably linear, some embodiments of which are referred to in the literature as "molecular wires". By "substantially conducting" herein is meant that the oligomer is capable of transfering electrons at 100 Hz. Generally, the conductive oligomer has substantially overlapping π-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to inject or receive electrons into or from an associated ETM. Furthermore, the conductive oligomer is more conductive than the insulators as defined herein. Additionally, the conductive oligomers of the invention are to be distinguished from electroactive polymers, that themselves may donate or accept electrons.

In a preferred embodiment, the conductive oligomers have a conductivity, S, of from between about $10^{-6}$ to about $10^4 \, \Omega^{-1} \, cm^{-1}$, with from about $10^{-5}$ to about $10^{-3} \, \Omega^{-1} cm^{-1}$ being preferred, with these S values being calculated for molecules ranging from about 20 Å to about 200 Å. As described below, insulators have a conductivity S of about $10^{-7} \, \Omega^{-1} cm^{-1}$ or lower, with less than about $10^{-8} \, \Omega^{-1} cm^{-1}$ being preferred. See generally Gardner et al., Sensors and Actuators A 51 (1995) 57–66, incorporated herein by reference.

Desired characteristics of a conductive oligomer include high conductivity, sufficient solubility in organic solvents and/or water for synthesis and use of the compositions of the invention, and preferably chemical resistance to reactions that occur i) during binding ligand synthesis (i.e. nucleic acid synthesis, such that nucleosides containing the conductive oligomers may be added to a nucleic acid synthesizer during the synthesis of the compositions of the invention, ii) during the attachment of the conductive oligomer to an electrode, or iii) during binding assays. In addition, conductive oligomers that will promote the formation of self-assembled monolayers are preferred.

The oligomers of the invention comprise at least two monomeric subunits, as described herein. As is described more fully below, oligomers include homo- and hetero-oligomers, and include polymers.

In a preferred embodiment, the conductive oligomer has the structure depicted in Structure 1:

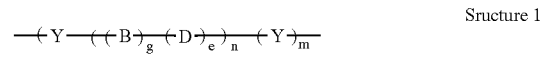

Structure 1

As will be understood by those in the art, all of the structures depicted herein may have additional atoms or structures; i.e. the conductive oligomer of Structure 1 may be attached to ETMs, such as electrodes, transition metal complexes, organic ETMs, and metallocenes, and to binding ligands such as nucleic acids, or to several of these. Unless otherwise noted, the conductive oligomers depicted herein will be attached at the left side to an electrode; that is, as depicted in Structure 1, the left "Y" is connected to the electrode as described herein. If the conductive oligomer is to be attached to a binding ligand, the right "Y", if present, is attached to the binding ligand such as a nucleic acid, either directly or through the use of a linker, as is described herein.

In this embodiment, Y is an aromatic group, n is an integer from 1 to 50, g is either 1 or zero, e is an integer from zero to 10, and m is zero or 1. When g is 1, B-D is a bond able to conjugate with neighboring bonds (herein referred to as a Aconjugated bond@), preferably selected from acetylene, alkene, substituted alkene, amide, azo, —C=N-(including —N=C—, —CR=N— and —N=CR—), -Si=Si—, and —Si=C— (including —C=Si—, —Si=CR— and —CR=Si—). When g is zero, e is preferably 1, D is preferably carbonyl, or a heteroatom moiety, wherein the heteroatom is selected from oxygen, sulfur, nitrogen, silicon or phosphorus. Thus, suitable heteroatom moieties include, but are not limited to, —NH and —NR, wherein R is as defined herein; substituted sulfur; sulfonyl (—SO$_2$—) sulfoxide (—SO—); phosphine oxide (—PO— and —RPO—); and thiophosphine (—PS— and —RPS—). However, when the conductive oligomer is to be attached to a gold electrode, as outlined below, sulfur derivatives are not preferred.

By "aromatic group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc.

Importantly, the Y aromatic groups of the conductive oligomer may be different, i.e. the conductive oligomer may be a heterooligomer. That is, a conductive oligomer may comprise a oligomer of a single type of Y groups, or of multiple types of Y groups.

The aromatic group may be substituted with a substitution group, generally depicted herein as R. R groups may be added as necessary to affect the packing of the conductive oligomers, i.e. R groups may be used to alter the association of the oligomers in the monolayer. R groups may also be added to 1) alter the solubility of the oligomer or of compositions containing the oligomers; 2) alter the conjugation or electrochemical potential of the system; and 3) alter the charge or characteristics at the surface of the monolayer.

In a preferred embodiment, when the conductive oligomer is greater than three subunits, R groups are preferred to increase solubility when solution synthesis is done. However, the R groups, and their positions, are chosen to minimally effect the packing of the conductive oligomers on a surface, particularly within a monolayer, as described below. In general, only small R groups are used within the monolayer, with larger R groups generally above the surface of the monolayer. Thus for example the attachment of methyl groups to the portion of the conductive oligomer within the monolayer to increase solubility is preferred, with attachment of longer alkoxy groups, for example, C3 to C10, is preferably done above the monolayer surface. In general, for the systems described herein, this generally means that attachment of sterically significant R groups is not done on any of the first two or three oligomer subunits, depending on the average length of the molecules making up the monolayer.

Suitable R groups include, but are not limited to, hydrogen, alkyl, alcohol, aromatic, amino, amido, nitro, ethers, esters, aldehydes, sulfonyl, silicon moieties, halogens, sulfur containing moieties, phosphorus containing moieties, and ethylene glycols. In the structures depicted herein, R is hydrogen when the position is unsubstituted. It should be noted that some positions may allow two substitution groups, R and R', in which case the R and R' groups may be either the same or different.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1–C30), with a preferred embodiment utilizing from about 1 to about 20 carbon atoms (C1–C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

By "amino groups" or grammatical equivalents herein is meant —$NH_2$, —NHR and —$NR_2$ groups, with R being as defined herein.

By "nitro group" herein is meant an —$NO_2$ group.

By "sulfur containing moieties" herein is meant compounds containing sulfur atoms, including but not limited to, thia-, thio- and sulfo- compounds, thiols (—SH and —SR), and sulfides (—RSR—). By "phosphorus containing moieties" herein is meant compounds containing phosphorus, including, but not limited to, phosphines and phosphates. By "silicon containing moieties" herein is meant compounds containing silicon.

By "ether" herein is meant an —O—R group. Preferred ethers include alkoxy groups, with —O—$(CH_2)_2CH_3$ and —O—$(CH_2)_4CH_3$ being preferred.

By "ester" herein is meant a —COOR group.

By "halogen" herein is meant bromine, iodine, chlorine, or fluorine. Preferred substituted alkyls are partially or fully halogenated alkyls such as $CF_3$, etc.

By "aldehyde" herein is meant —RCHO groups.

By "alcohol" herein is meant —OH groups, and alkyl alcohols —ROH.

By "amido" herein is meant —RCONH— or RCONR— groups.

By "ethylene glycol" or "(poly)ethylene glycol" herein is meant a —$(O—CH_2—CH_2)_n$— group, although each carbon atom of the ethylene group may also be singly or doubly substituted, i.e. —$(O—CR_2—CR_2)_n$—, with R as described above. Ethylene glycol derivatives with other heteroatoms in place of oxygen (i.e. —$(N—CH_2—CH_2)_n$— or —$(S—CH_2—CH_2)_n$—, or with substitution groups) are also preferred.

Preferred substitution groups include, but are not limited to, methyl, ethyl, propyl, alkoxy groups such as —O—$(CH_2)_2CH_3$ and —O—$(CH_2)_4$ $CH_3$ and ethylene glycol and derivatives thereof.

Preferred aromatic groups include, but are not limited to, phenyl, naphthyl, naphthalene, anthracene, phenanthroline, pyrole, pyridine, thiophene, porphyrins, and substituted derivatives of each of these, included fused ring derivatives.

In the conductive oligomers depicted herein, when g is 1, B-D is a bond linking two atoms or chemical moieties. In a preferred embodiment, B-D is a conjugated bond, containing overlapping or conjugated π-orbitals.

Preferred B-D bonds are selected from acetylene (—C≡C—, also called alkyne or ethyne), alkene (—CH═CH—, also called ethylene), substituted alkene (—CR═CR—, —CH═CR— and —CR═CH—), amide (—NH—CO— and —NR—CO— or —CO—NH— and —CO—NR—), azo (—N═N—), esters and thioesters (—CO—O—, —O—CO—, —CS—O— and —O—CS—) and other conjugated bonds such as (—CH═N—, —CR═N—, —N═CH— and —N═CR—), (—SiH═SiH—, —SiR═SiH—, —SiR═SiH—, and —SiR═SiR—), (—SiH═CH—, —SiR═CH—, —SiH═CR—, —SiR═CR—, —CH═SiH—, —CR═SiH—, —CH═SiR—, and —CR═SiR—). Particularly preferred B-D bonds are acetylene, alkene, amide, and substituted derivatives of these three, and azo. Especially preferred B-D bonds are acetylene, alkene and amide. The oligomer components attached to double bonds may be in the trans or cis conformation, or mixtures. Thus, either B or D may include carbon, nitrogen or silicon. The substitution groups are as defined as above for R.

When g=0 in the Structure 1 conductive oligomer, e is preferably 1 and the D moiety may be carbonyl or a heteroatom moiety as defined above.

As above for the Y rings, within any single conductive oligomer, the B-D bonds (or D moieties, when g=0) may be all the same, or at least one may be different. For example, when m is zero, the terminal B-D bond may be an amide bond, and the rest of the B-D bonds may be acetylene bonds. Generally, when amide bonds are present, as few amide bonds as possible are preferable, but in some embodiments all the B-D bonds are amide bonds. Thus, as outlined above for the Y rings, one type of B-D bond may be present in the conductive oligomer within a monolayer as described below, and another type above the monolayer level, for example to give greater flexibility for nucleic acid hybridization when the nucleic acid is attached via a conductive oligomer.

In the structures depicted herein, n is an integer from 1 to 50, although longer oligomers may also be used (see for example Schumm et al., Angew. Chem. Int. Ed. Engl. 1994 33(13):1360). Without being bound by theory, it appears that for efficient hybridization of nucleic acids on a surface, the hybridization should occur at a distance from the surface, i.e. the kinetics of hybridization increase as a function of the distance from the surface, particularly for long oligonucleotides of 200 to 300 basepairs. Accordingly, when a nucleic acid is attached via a conductive oligomer, as is more fully described below, the length of the conductive oligomer is such that the closest nucleotide of the nucleic acid is positioned from about 6 Å to about 100 Å (although distances of up to 500 Å may be used) from the electrode surface, with from about 15 Å to about 60 Å being preferred and from about 25 Å to about 60 Å also being preferred. Accordingly, n will depend on the size of the aromatic group, but generally will be from about 1 to about 20, with from about 2 to about 15 being preferred and from about 3 to about 10 being especially preferred.

In the structures depicted herein, m is either 0 or 1. That is, when m is 0, the conductive oligomer may terminate in the B-D bond or D moiety, i.e. the D atom is attached to the nucleic acid either directly or via a linker. In some embodiments, for example when the conductive oligomer is attached to a phosphate of the ribose-phosphate backbone of a nucleic acid, there may be additional atoms, such as a linker, attached between the conductive oligomer and the nucleic acid. Additionally, as outlined below, the D atom may be the nitrogen atom of the amino-modified ribose. Alternatively, when m is 1, the conductive oligomer may terminate in Y, an aromatic group, i.e. the aromatic group is attached to the nucleic acid or linker.

As will be appreciated by those in the art, a large number of possible conductive oligomers may be utilized. These include conductive oligomers falling within the Structure 1 and Structure 8 formulas, as well as other conductive oligomers, as are generally known in the art, including for example, compounds comprising fused aromatic rings or Teflon®-like oligomers, such as —(CF$_2$)$_n$—, —(CHF)$_n$— and —(CFR)$_n$—. See for example, Schumm et al., Angew. Chem. Intl. Ed. Engl. 33:1361 (1994); Grosshenny et al., Platinum Metals Rev. 40(1):26–35 (1996); Tour, Chem. Rev. 96:537–553 (1996); Hsung et al., Organometallics 14:4808–4815 (1995; and references cited therein, all of which are expressly incorporated by reference.

Particularly preferred conductive oligomers of this embodiment are depicted below:

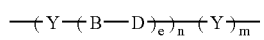

Structure 2

Structure 2 is Structure 1 when g is 1. Preferred embodiments of Structure 2 include: e is zero, Y is pyrole or substituted pyrole; e is zero, Y is thiophene or substituted thiophene; e is zero, Y is furan or substituted furan; e is zero, Y is phenyl or substituted phenyl; e is zero, Y is pyridine or substituted pyridine; e is 1, B-D is acetylene and Y is phenyl or substituted phenyl (see Structure 4 below). A preferred embodiment of Structure 2 is also when e is one, depicted as Structure 3 below:

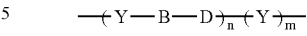

Structure 3

Preferred embodiments of Structure 3 are: Y is phenyl or substituted phenyl and B-D is azo; Y is phenyl or substituted phenyl and B-D is acetylene; Y is phenyl or substituted phenyl and B-D is alkene; Y is pyridine or substituted pyridine and B-D is acetylene; Y is thiophene or substituted thiophene and B-D is acetylene; Y is furan or substituted furan and B-D is acetylene; Y is thiophene or furan (or substituted thiophene or furan) and B-D are alternating alkene and acetylene bonds.

Most of the structures depicted herein utilize a Structure 3 conductive oligomer. However, any Structure 3 oligomers may be substituted with any of the other structures depicted herein, i.e. Structure 1 or 8 oligomer, or other conducting oligomer, and the use of such Structure 3 depiction is not meant to limit the scope of the invention.

Particularly preferred embodiments of Structure 3 include Structures 4, 5, 6 and 7, depicted below:

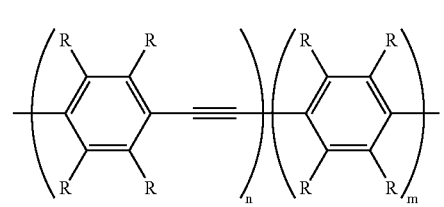

Structure 4

Particularly preferred embodiments of Structure 4 include: n is two, m is one, and R is hydrogen; n is three, m is zero, and R is hydrogen; and the use of R groups to increase solubility.

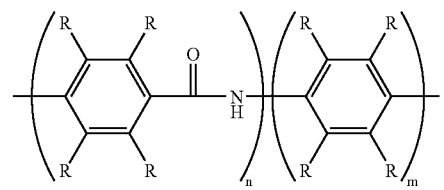

Structure 5

When the B-D bond is an amide bond, as in Structure 5, the conductive oligomers are pseudopeptide oligomers. Although the amide bond in Structure 5 is depicted with the carbonyl to the left, i.e. —CONH—, the reverse may also be used, i.e. —NHCO—. Particularly preferred embodiments of Structure 5 include: n is two, m is one, and R is hydrogen; n is three, m is zero, and R is hydrogen (in this embodiment, the terminal nitrogen (the D atom) may be the nitrogen of the amino-modified ribose); and the use of R groups to increase solubility.

Structure 6

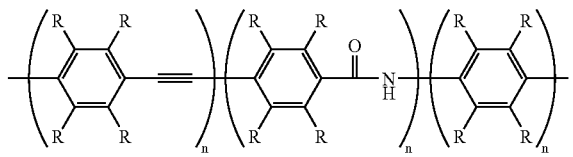

Preferred embodiments of Structure 6 include the first n is two, second n is one, m is zero, and all R groups are hydrogen, or the use of R groups to increase solubility.

Structure 7

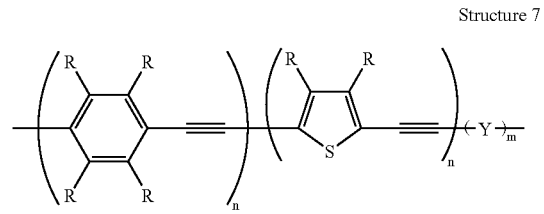

Preferred embodiments of Structure 7 include: the first n is three, the second n is from 1–3, with m being either 0 or 1, and the use of R groups to increase solubility.

In a preferred embodiment, the conductive oligomer has the structure depicted in Structure 8:

Structure 8

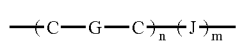

In this embodiment, C are carbon atoms, n is an integer from 1 to 50, m is 0 or 1, J is a heteroatom selected from the group consisting of oxygen, nitrogen, silicon, phosphorus, sulfur, carbonyl or sulfoxide, and G is a bond selected from alkane, alkene or acetylene, such that together with the two carbon atoms the C—G—C group is an alkene (—CH=CH—), substituted alkene (—CR=CR—) or mixtures thereof (—CH=CR— or —CR=CH—), acetylene (—C≡C—), or alkane (—CR$_2$—CR$_2$—, with R being either hydrogen or a substitution group as described herein). The G bond of each subunit may be the same or different than the G bonds of other subunits; that is, alternating oligomers of alkene and acetylene bonds could be used, etc. However, when G is an alkane bond, the number of alkane bonds in the oligomer should be kept to a minimum, with about six or less sigma bonds per conductive oligomer being preferred. Alkene bonds are preferred, and are generally depicted herein, although alkane and acetylene bonds may be substituted in any structure or embodiment described herein as will be appreciated by those in the art.

In some embodiments, for example when ETMs are not present, if m=0 then at least one of the G bonds is not an alkane bond.

In a preferred embodiment, the m of Structure 8 is zero. In a particularly preferred embodiment, m is zero and G is an alkene bond, as is depicted in Structure 9:

Structure 9

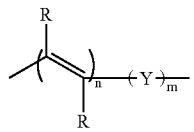

The alkene oligomer of structure 9, and others depicted herein, are generally depicted in the preferred trans configuration, although oligomers of cis or mixtures of trans and cis may also be used. As above, R groups may be added to alter the packing of the compositions on an electrode, the hydrophilicity or hydrophobicity of the oligomer, and the flexibility, i.e. the rotational, torsional or longitudinal flexibility of the oligomer. n is as defined above.

In a preferred embodiment, R is hydrogen, although R may be also alkyl groups and polyethylene glycols or derivatives.

In an alternative embodiment, the conductive oligomer may be a mixture of different types of oligomers, for example of structures 1 and 8.

The conductive oligomers may or may not have terminal groups. Thus, in a preferred embodiment, there is no additional terminal group, and the conductive oligomer terminates with one of the groups depicted in Structures 1 to 9; for example, a B-D bond such as an acetylene bond. Alternatively, in a preferred embodiment, a terminal group is added, sometimes depicted herein as "Q". A terminal group may be used for several reasons; for example, to contribute to the electronic availability of the conductive oligomer for detection of ETMs, or to alter the surface of the SAM for other reasons, for example to prevent non-specific binding. For example, when the target analyte is a nucleic acid, there may be negatively charged groups on the terminus to form a negatively charged surface such that when the nucleic acid is DNA or RNA the nucleic acid is repelled or prevented from lying down on the surface, to facilitate hybridization. Preferred terminal groups include —NH$_2$, —OH, —COOH, and alkyl groups such as —CH$_3$, and (poly)alkyloxides such as (poly)ethylene glycol, with —OCH$_2$CH$_2$OH, —(OCH$_2$CH$_2$O)$_2$H, —(OCH$_2$CH$_2$O)$_3$H, and —(OCH$_2$CH$_2$O)$_4$H being preferred.

In one embodiment, it is possible to use mixtures of conductive oligomers with different types of terminal groups. Thus, for example, some of the terminal groups may facilitate detection, and some may prevent non-specific binding.

It will be appreciated that the monolayer may comprise different conductive oligomer species, although preferably the different species are chosen such that a reasonably uniform SAM can be formed. Thus, for example, when capture binding ligands such as nucleic acids are covalently attached to the electrode using conductive oligomers, it is possible to have one type of conductive oligomer used to attach the nucleic acid, and another type in the SAM. Similarly, it may be desirable to have mixtures of different lengths of conductive oligomers in the monolayer, to help reduce non-specific signals. Thus, for example, preferred embodiments utilize conductive oligomers that terminate below the surface of the rest of the monolayer, i.e. below the insulator layer, if used, or below some fraction of the other conductive oligomers. Similarly, the use of different conductive oligomers may be done to facilitate monolayer formation, or to make monolayers with altered properties.

In a preferred embodiment, the monolayer may further comprise insulator moieties. By "insulator" herein is meant a substantially nonconducting oligomer, preferably linear. By "substantially nonconducting" herein is meant that the insulator will not transfer electrons at 100 Hz. The rate of electron transfer through the insulator is preferrably slower than the rate through the conductive oligomers described herein.

In a preferred embodiment, the insulators have a conductivity, S, of about $10^{-7}$ $\Omega^{-1}cm^{-1}$ or lower, with less than about $10^{-8}$ $\Omega^{-1}cm^{-1}$ being preferred. See generally Gardner et al., supra.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow, preferably substantially, electron transfer.

Suitable insulators are known in the art, and include, but are not limited to, —$(CH_2)_n$—, —$(CRH)_n$—, and —$(CR_2)_n$—, ethylene glycol or derivatives using other heteroatoms in place of oxygen, i.e. nitrogen or sulfur (sulfur derivatives are not preferred when the electrode is gold).

As for the conductive oligomers, the insulators may be substituted with R groups as defined herein to alter the packing of the moieties or conductive oligomers on an electrode, the hydrophilicity or hydrophobicity of the insulator, and the flexibility, i.e. the rotational, torsional or longitudinal flexibility of the insulator. For example, branched alkyl groups may be used. Similarly, the insulators may contain terminal groups, as outlined above, particularly to influence the surface of the monolayer.

The length of the species making up the monolayer will vary as needed. As outlined above, it appears that binding of target analytes (for example, hybridization of nucleic acids) is more efficient at a distance from the surface. The species to which capture binding ligands are attached (as outlined below, these can be either insulators or conductive oligomers) may be basically the same length as the monolayer forming species or longer than them, resulting in the capture binding ligands being more accessible to the solvent for hybridization. In some embodiments, the conductive oligomers to which the capture binding ligands are attached may be shorter than the monolayer.

As will be appreciated by those in the art, the actual combinations and ratios of the different species making up the monolayer can vary widely, and will depend on whether mechanism-1 or -2 is used, and, in the case of electrophoresis, whether a one electrode system or two electrode system is used, as is more fully outlined below. Generally, three component systems are preferred for mechanism-2 systems, with the first species comprising a capture binding ligand containing species (termed a capture probe when the target analyte is a nucleic acid), attached to the electrode via either an insulator or a conductive oligomer. The second species are conductive oligomers, and the third species are insulators. In this embodiment, the first species can comprise from about 90% to about 1%, with from about 20% to about 40% being preferred. When the target analytes are nucleic acids, from about 30% to about 40% is especially preferred for short oligonucleotide targets and from about 10% to about 20% is preferred for longer targets. The second species can comprise from about 1% to about 90%, with from about 20% to about 90% being preferred, and from about 40% to about 60% being especially preferred. The third species can comprise from about 1% to about 90%, with from about 20% to about 40% being preferred, and from about 15% to about 30% being especially preferred. To achieve these approximate proportions, preferred ratios of first:second:third species in SAM formation solvents are 2:2:1 for short targets, 1:3:1 for longer targets, with total thiol concentration (when used to attach these species, as is more fully outlined below) in the 500 μM to 1 mM range, and 833 μM being preferred.

Alternatively, two component systems can be used. In one embodiment, for use in either mechanism-1 or mechanism-2 systems, the two components are the first and second species. In this embodiment, the first species can comprise from about 1% to about 90%, with from about 1% to about 40% being preferred, and from about 10% to about 40% being especially preferred. The second species can comprise from about 1% to about 90%, with from about 10% to about 60% being preferred, and from about 20% to about 40% being especially preferred. Alternatively, for mechanism-1 systems, the two components are the first and the third species. In this embodiment, the first species can comprise from about 1% to about 90%, with from about 1% to about 40% being preferred, and from about 10% to about 40% being especially preferred. The second species can comprise from about 1% to about 90%, with from about 10% to about 60% being preferred, and from about 20% to about 40% being especially preferred.

In a preferred embodiment, the deposition of the SAM is done using aqueous solvents. As is generally described in Steel et al., Anal. Chem. 70:4670 (1998), Herne et al., J. Am. Chem. Soc. 119:8916 (1997), and Finklea, Electrochemistry of Organized Monolayers of Thiols and Related Molecules on Electrodes, from A. J. Bard, *Electroanalytical Chemistry: A Series of Advances*, Vol. 20, Dekker N.Y. 1966-, all of which are expressly incorporated by reference, the deposition of the SAM-forming species can be done out of aqueous solutions, frequently comprising salt.

In addition, when electrophoresis systems are used, the composition and integrity of the monolayer may depend on whether a one electrode or two electrode system is used. Thus, for example, if a one electrode system is used for both electrophoresis and detection, the configuration of the system will allow the electroactive charge carriers, if used, access to the electrode. As will be appreciated by those in the art, if the chemistry of attachment of the conductive oligomer is stable at the high voltages used to hydrolyze water, no electroactive charge carriers need be used. This may be done in one of several ways. In a preferred embodiment, the monolayer comprises a significant component of electronically exposed conductive oligomers; a monolayer such as this effective raises the surface of the electrode, allowing the electroactive charge carriers indirect access to the electrode. Alternatively, a poor monolayer may be used, i.e. a monolayer that contains "pinholes" or "imperfections", such that there is direct solvent access to the electrode. Alternatively, the configuration of the electrode may be such that less than the entire surface of the electrode is covered by a SAM, to allow direct access to the electrode, but minimizing the surface for non-specific binding.

The covalent attachment of the conductive oligomers and insulators to the electrode may be accomplished in a variety of ways, depending on the electrode and the composition of the insulators and conductive oligomers used. In a preferred embodiment, the attachment linkers with covalently attached nucleosides or nucleic acids as depicted herein are covalently attached to an electrode. Thus, one end or terminus of the attachment linker is attached to the nucleoside or nucleic acid, and the other is attached to an electrode. In some embodiments it may be desirable to have the attachment linker attached at a position other than a terminus, or even to have a branched attachment linker that is attached to an electrode at one terminus and to two or more nucleosides at other termini, although this is not preferred. Similarly, the attachment linker may be attached at two sites to the electrode, as is generally depicted in Structures 11–13. Generally, some type of linker is used, as depicted below as "A" in Structure 10, where "X" is the conductive oligomer, "I" is an insulator and the hatched surface is the electrode:

Structure 10

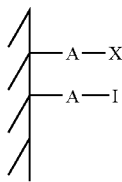

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al., Langmuir 10:3332–3337 (1994); Lenhard et al., J. Electroanal. Chem. 78:195–201 (1977), both of which are expressly incorporated by reference). When carbon based electrodes are used, A may be an amino moiety (preferably a primary amine; see for example Deinhammer et al., Langmuir 10:1306–1313 (1994)). Thus, preferred A moieties include, but are not limited to, silane moieties, sulfur moieties (including alkyl sulfur moieties), and amino moieties. In a preferred embodiment, epoxide type linkages with redox polymers such as are known in the art are not used.

Although depicted herein as a single moiety, the insulators and conductive oligomers may be attached to the electrode with more than one "A" moiety; the "A" moieties may be the same or different. Thus, for example, when the electrode is a gold electrode, and "A" is a sulfur atom or moiety, multiple sulfur atoms may be used to attach the conductive oligomer to the electrode, such as is generally depicted below in Structures 11, 12 and 13. As will be appreciated by those in the art, other such structures can be made. In Structures 11, 12 and 13, the A moiety is just a sulfur atom, but substituted sulfur moieties may also be used.

Structure 11

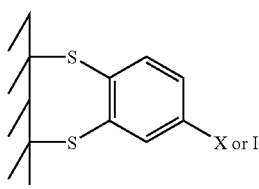

Structure 12

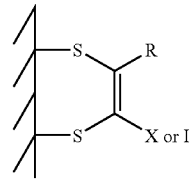

Structure 13

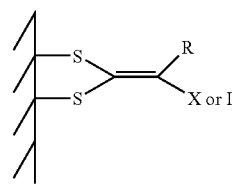

It should also be noted that similar to Structure 13, it may be possible to have a a conductive oligomer terminating in a single carbon atom with three sulfur moieties attached to the electrode. Additionally, although not always depicted herein, the conductive oligomers and insulators may also comprise a "Q" terminal group.

In a preferred embodiment, the electrode is a gold electrode, and attachment is via a sulfur linkage as is well known in the art, i.e. the A moiety is a sulfur atom or moiety. Although the exact characteristics of the gold-sulfur attachment are not known, this linkage is considered covalent for the purposes of this invention. A representative structure is depicted in Structure 14, using the Structure 3 conductive oligomer, although as for all the structures depicted herein, any of the conductive oligomers, or combinations of conductive oligomers, may be used. Similarly, any of the conductive oligomers or insulators may also comprise terminal groups as described herein. Structure 14 depicts the "A" linker as comprising just a sulfur atom, although additional atoms may be present (i.e. linkers from the sulfur to the conductive oligomer or substitution groups). In addition, Structure 14 shows the sulfur atom attached to the Y aromatic group, but as will be appreciated by those in the art, it may be attached to the B-D group (i.e. an acetylene) as well.

Structure 14

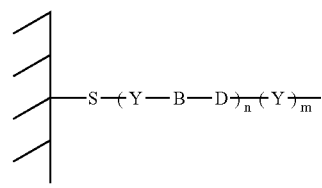

In general, thiol linkages are preferred. In systems using electrophoresis, thiol linkages are preferred when either two sets of electrodes are used (i.e. the detection electrodes comprising the SAMs are not used at high electrophoretic voltages (i.e. greater than 800 or 900 mV), that can cause oxidation of the thiol linkage and thus loss of the SAM), or, if one set of electrodes is used, lower electrophoretic voltages are used as is generally described below.

In a preferred embodiment, the electrode is a carbon electrode, i.e. a glassy carbon electrode, and attachment is via a nitrogen of an amine group. A representative structure is depicted in Structure 15. Again, additional atoms may be present, i.e. Z type linkers and/or terminal groups.

Structure 15

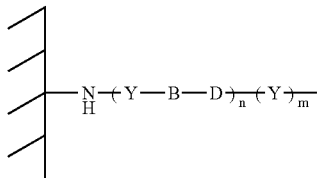

Structure 16

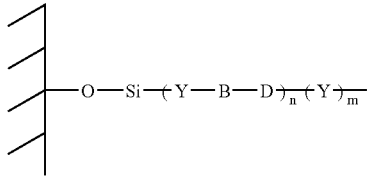

In Structure 16, the oxygen atom is from the oxide of the metal oxide electrode. The Si atom may also contain other atoms, i.e. be a silicon moiety containing substitution groups. Other attachments for SAMs to other electrodes are known in the art; see for example Napier et al., Langmuir, 1997, for attachment to indium tin oxide electrodes, and also the chemisorption of phosphates to an indium tin oxide electrode (talk by H. Holden Thorpe, CHI conference, May 4–5, 1998).

The SAMs of the invention can be made in a variety of ways, including deposition out of organic solutions and deposition out of aqueous solutions. The methods outlined herein use a gold electrode as the example, although as will be appreciated by those in the art, other metals and methods may be used as well. In one preferred embodiment, indium-tin-oxide (ITO) is used as the electrode.

In a preferred embodiment, a gold surface is first cleaned. A variety of cleaning procedures may be employed, including, but not limited to, chemical cleaning or etchants (including Piranha solution (hydrogen peroxide/sulfuric acid) or aqua regia (hydrochloric acid/nitric acid), electrochemical methods, flame treatment, plasma treatment or combinations thereof.

Following cleaning, the gold substrate is exposed to the SAM species. When the electrode is ITO, the SAM species are phosphonate-containing species. This can also be done in a variety of ways, including, but not limited to, solution deposition, gas phase deposition, microcontact printing, spray deposition, deposition using neat components, etc. A preferred embodiment utilizes a deposition solution comprising a mixture of various SAM species in solution, generally thiol-containing species. Mixed monolayers that contain target analytes, particularly DNA, are usually prepared using a two step procedure. The thiolated DNA is deposited during the first deposition step (generally in the presence of at least one other monolayer-forming species) and the mixed monolayer formation is completed during the second step in which a second thiol solution minus DNA is added. The second step can involve mild heating to promote monolayer reorganization, although this is not preferred in all embodiments.

In a preferred embodiment, the deposition solution is an organic deposition solution. In this embodiment, a clean gold surface is placed into a clean vial. A binding ligand deposition solution in organic solvent is prepared in which the total thiol concentration is between micromolar to saturation; preferred ranges include from about 1 µM to 10 mM, with from about 400 µM to about 1.0 mM being especially preferred. In a preferred embodiment, the deposition solution contains thiol modified DNA (i.e. nucleic acid attached to an attachment linker) and thiol diluent molecules (either conductive oligomers or insulators, with the latter being preferred). The ratio of DNA to diluent (if present) is usually between 1000:1 to 1:1000, with from about 10:1 to about 1:10 being preferred and 1:1 being especially preferred. The preferred solvents are tetrahydrofuran (THF), acetonitrile, dimethylforamide (DMF), ethanol, or mixtures thereof; generally any solvent of sufficient polarity to dissolve the capture ligand can be used, as long as the solvent is devoid of functional groups that will react with the surface. Sufficient DNA deposition solution is added to the vial so as to completely cover the electrode surface. The gold substrate is allowed to incubate at ambient temperature or slightly above ambient temperature for a period of time ranging from seconds to hours, with 5–30 minutes being preferred. After the initial incubation, the deposition solution is removed and a solution of diluent molecule only (from about 1 µM to 10 mM, with from about 100 uM to about 1.0 mM being preferred) in organic solvent is added. The gold substrate is allowed to incubate at room temperature or above room temperature for a period of time (seconds to days, with from about 10 minutes to about 24 hours being preferred). The gold sample is removed from the solution, rinsed in clean solvent and used.

In a preferred embodiment, an aqueous deposition solution is used. As above, a clean gold surface is placed into a clean vial. A DNA deposition solution in water is prepared in which the total thiol concentration is between about 1 uM and 10 mM, with from about 1 µM to about 200 uM being preferred. The aqueous solution frequently has salt present (up to saturation, with approximately 1 M being preferred), however pure water can be used. The deposition solution contains thiol modified DNA and often a thiol diluent molecule. The ratio of DNA to diluent is usually between between 1000:1 to 1:1000, with from about 10:1 to about 1:10 being preferred and 1:1 being especially preferred. The DNA deposition solution is added to the vial in such a volume so as to completely cover the electrode surface. The gold substrate is allowed to incubate at ambient temperature or slightly above ambient temperature for 1–30 minutes with 5 minutes usually being sufficient. After the initial incubation, the deposition solution is removed and a solution of diluent molecule only (10 uM–1.0 mM) in either water or organic solvent is added. The gold substrate is allowed to incubate at room temperature or above room temperature until a complete monolayer is formed (10 minutes–24 hours). The gold sample is removed from the solution, rinsed in clean solvent and used.

In a preferred embodiment, as outlined herein, a circuit board is used as the substrate for the gold electrodes. Formation of the SAMs on the gold surface is generally done by first cleaning the boards, for example in a 10% sulfuric acid solution for 30 seconds, detergent solutions, aqua regia, plasma, etc., as outlined herein. Following the sulfuric acid treatment, the boards are washed, for example via immersion in two Milli-Q water baths for 1 minute each. The boards are then dried, for example under a stream of nitrogen. Spotting of the deposition solution onto the boards is done using any number of known spotting systems, generally by placing the boards on an X-Y table, preferably in a humidity chamber. The size of the spotting drop will vary with the size of the electrodes on the boards and the equipment used for delivery of the solution; for example, for 250 µM size electrodes, a 30 nanoliter drop is used. The volume should be sufficient to cover the electrode surface completely. The drop is incubated at room temperature for a period of time (sec to overnight, with 5 minutes preferred) and then the drop is removed by rinsing in a Milli-Q water bath. The boards are then preferably treated with a second deposition solution, generally comprising insulator in organic solvent, preferably acetonitrile, by immersion in a 45° C. bath. After 30 minutes, the boards are removed and immersed in an acetonitrile bath for 30 seconds followed by a milli-Q water bath for 30 seconds. The boards are dried under a stream of nitrogen.

In a preferred embodiment, the detection electrode further comprises a capture binding ligand, preferably covalently attached. By "binding ligand" or "binding species" herein is meant a compound that is used to probe for the presence of the target analyte, that will bind to the target analyte. In general, for most of the embodiments described herein, there are at least two binding ligands used per target analyte molecule; a "capture" or "anchor" binding ligand (also referred to herein as a "capture probe", particularly in reference to a nucleic acid binding ligand) that is attached to the detection electrode as described herein, and a soluble binding ligand, that binds independently to the target analyte, and either directly or indirectly comprises at least one ETM.

Generally, the capture binding ligand allows the attachment of a target analyte to the detection electrode, for the purposes of detection. As is more fully outlined below, attachment of the target analyte to the capture binding ligand may be direct (i.e. the target analyte binds to the capture binding ligand) or indirect (one or more capture extender ligands may be used).

In a preferred embodiment, the binding is specific, and the binding ligand is part of a binding pair. By "specifically bind" herein is meant that the ligand binds the analyte, with specificity sufficient to differentiate between the analyte and other components or contaminants of the test sample. However, as will be appreciated by those in the art, it will be possible to detect analytes using binding that is not highly specific; for example, the systems may use different binding ligands, for example an array of different ligands, and detection of any particular analyte is via its "signature" of binding to a panel of binding ligands, similar to the manner in which "electronic noses" work. The binding should be sufficient to allow the analyte to remain bound under the conditions of the assay, including wash steps to remove non-specific binding. In some embodiments, for example in the detection of certain biomolecules, the binding constants of the analyte to the binding ligand will be at least about $10^{-4}$ to $10^{-6}$ $M^{-1}$, with at least about $10^{-5}$ to $10^{-9}$ being preferred and at least about $10^{-7}$ to $10^{-9}$ $M^{-1}$ being particularly preferred.

As will be appreciated by those in the art, the composition of the binding ligand will depend on the composition of the target analyte. Binding ligands to a wide variety of analytes are known or can be readily found using known techniques. For example, when the analyte is a single-stranded nucleic acid, the binding ligand is generally a substantially complementary nucleic acid. Alternatively, as is generally described in U.S. Pat. Nos. 5,270,163, 5,475,096, 5,567,588, 5,595, 877, 5,637,459, 5,683,867, 5,705,337, and related patents, hereby incorporated by reference, nucleic acid "aptomers" can be developed for binding to virtually any target analyte. Similarly the analyte may be a nucleic acid binding protein and the capture binding ligand is either a single-stranded or double-stranded nucleic acid; alternatively, the binding ligand may be a nucleic acid binding protein when the analyte is a single or double-stranded nucleic acid. When the analyte is a protein, the binding ligands include proteins (particularly including antibodies or fragments thereof (FAbs, etc.)), small molecules, or aptamers, described above. Preferred binding ligand proteins include peptides. For example, when the analyte is an enzyme, suitable binding ligands include substrates, inhibitors, and other proteins that bind the enzyme, i.e. components of a multi-enzyme (or protein) complex. As will be appreciated by those in the art, any two molecules that will associate, preferably specifically, may be used, either as the analyte or the binding ligand. Suitable analyte/binding ligand pairs include, but are not limited to, antibodies/antigens, receptors/ligand, proteins/nucleic acids; nucleic acids/nucleic acids, enzymes/substrates and/or inhibitors, carbohydrates (including glycoproteins and glycolipids)/lectins, carbohydrates and other binding partners, proteins/proteins; and protein/small molecules. These may be wild-type or derivative sequences. In a preferred embodiment, the binding ligands are portions (particularly the extracellular portions) of cell surface receptors that are known to multimerize, such as the growth hormone receptor, glucose transporters (particularly GLUT4 receptor), transferrin receptor, epidermal growth factor receptor, low density lipoprotein receptor, high density lipoprotein receptor, leptin receptor, interleukin receptors including IL-1, IL-2, IL-3, IL-4, IL-5, IL-6, IL-7, IL-8, IL-9, IL-11, IL-12, IL-13, IL-15 and IL-17 receptors, VEGF receptor, PDGF receptor, EPO receptor, TPO receptor, ciliary neurotrophic factor receptor, prolactin receptor, and T-cell receptors. Similarly, there is a wide body of literature relating to the development of binding partners based on combinatorial chemistry methods.

In this embodiment, when the binding ligand is a nucleic acid, preferred compositions and techniques are outlined in WO 98/20162; PCT/US98/12430; PCT/US98/12082; PCT/US99/01705; PCT/US99/01703; and U.S. Ser. Nos. 09/135, 183; 60/105,875; and 09/295,691, all of which are hereby expressly incorporated by reference.

The method of attachment of the capture binding ligands to the attachment linker (either an insulator or conductive oligomer) will generally be done as is known in the art, and will depend on both the composition of the attachment linker and the capture binding ligand. In general, the capture binding ligands are attached to the attachment linker through the use of functional groups on each that can then be used for attachment. Preferred functional groups for attachment are amino groups, carboxy groups, oxo groups and thiol groups. These functional groups can then be attached, either directly or indirectly through the use of a linker, sometimes depicted herein as "Z". Linkers are well known in the art; for example, homo-or hetero-bifunctional linkers as are well known (see 1994 Pierce Chemical Company catalog, technical section on cross-linkers, pages 155–200, incorporated herein by reference). Preferred Z linkers include, but are not limited to, alkyl groups (including substituted alkyl groups and alkyl groups containing heteroatom moieties), with short alkyl groups, esters, amide, amine, epoxy groups and ethylene glycol and derivatives being preferred, with propyl, acetylene, and $C_2$ alkene being especially preferred. Z may also be a sulfone group, forming sulfonamide linkages.

In this way, capture binding ligands comprising proteins, lectins, nucleic acids, small organic molecules, carbohydrates, etc. can be added.

A preferred embodiment utilizes proteinaceous capture binding ligands. As is known in the art, any number of techniques may be used to attach a proteinaceous capture binding ligand to an attachment linker. A wide variety of techniques are known to add moieties to proteins.

A preferred embodiment utilizes nucleic acids as the capture binding ligand. While most of the following discussion focuses on nucleic acids, as will be appreciated by those in the art, many of the techniques outlined below apply in a similar manner to non-nucleic acid systems as well.

The capture probe nucleic acid is covalently attached to the electrode, via an "attachment linker", that can be either a conductive oligomer (required for mechanism-1 systems) or an insulator. By "covalently attached" herein is meant that two moieties are attached by at least one bond, including sigma bonds, pi bonds and coordination bonds.

Thus, one end of the attachment linker is attached to a nucleic acid (or other binding ligand), and the other end (although as will be appreciated by those in the art, it need not be the exact terminus for either) is attached to the electrode. Thus, any of structures depicted herein may further comprise a nucleic acid effectively as a terminal group. Thus, the present invention provides compositions comprising nucleic acids covalently attached to electrodes as is generally depicted below in Structure 17:

Structure 17

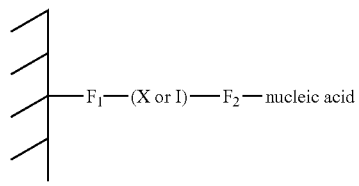

In Structure 17, the hatched marks on the left represent an electrode. X is a conductive oligomer and I is an insulator as defined herein. $F_1$ is a linkage that allows the covalent attachment of the electrode and the conductive oligomer or insulator, including bonds, atoms or linkers such as is described herein, for example as "A", defined below. $F_2$ is a linkage that allows the covalent attachment of the conductive oligomer or insulator to the nucleic acid, and may be a bond, an atom or a linkage as is herein described. $F_2$ may be part of the conductive oligomer, part of the insulator, part of the nucleic acid, or exogenous to both, for example, as defined herein for "Z".

In a preferred embodiment, the capture probe nucleic acid is covalently attached to the electrode via a conductive oligomer. The covalent attachment of the nucleic acid and the conductive oligomer may be accomplished in several ways. In a preferred embodiment, the attachment is via attachment to the base of the nucleoside, via attachment to the backbone of the nucleic acid (either the ribose, the phosphate, or to an analogous group of a nucleic acid analog backbone), or via a transition metal ligand, as described below. The techniques outlined below are generally described for naturally occuring nucleic acids, although as will be appreciated by those in the art, similar techniques may be used with nucleic acid analogs, and in some cases with other binding ligands.

In a preferred embodiment, the conductive oligomer is attached to the base of a nucleoside of the nucleic acid. This may be done in several ways, depending on the oligomer, as is described below. In one embodiment, the oligomer is attached to a terminal nucleoside, i.e. either the 3' or 5' nucleoside of the nucleic acid. Alternatively, the conductive oligomer is attached to an internal nucleoside.

The point of attachment to the base will vary with the base. Generally, attachment at any position is possible. In some embodiments, for example when the probe containing the ETMs may be used for hybridization (i.e. mechanism-1 systems), it is preferred to attach at positions not involved in hydrogen bonding to the complementary base. Thus, for example, generally attachment is to the 5 or 6 position of pyrimidines such as uridine, cytosine and thymine. For purines such as adenine and guanine, the linkage is preferably via the 8 position. Attachment to non-standard bases is preferably done at the comparable positions.

In one embodiment, the attachment is direct; that is, there are no intervening atoms between the conductive oligomer and the base. In this embodiment, for example, conductive oligomers with terminal acetylene bonds are attached directly to the base. Structure 18 is an example of this linkage, using a Structure 3 conductive oligomer and uridine as the base, although other bases and conductive oligomers can be used as will be appreciated by those in the art:

Structure 18

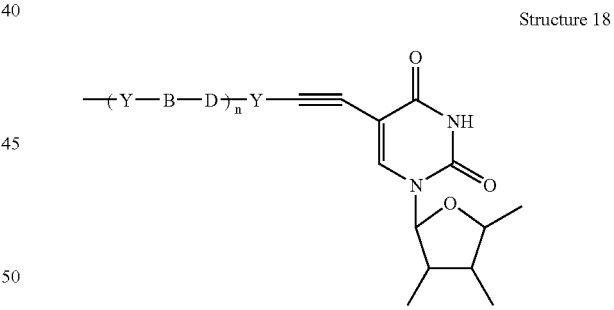

It should be noted that the pentose structures depicted herein may have hydrogen, hydroxy, phosphates or other groups such as amino groups attached. In addition, the pentose and nucleoside structures depicted herein are depicted non-conventionally, as mirror images of the normal rendering. In addition, the pentose and nucleoside structures may also contain additional groups, such as protecting groups, at any position, for example as needed during synthesis.

In addition, the base may contain additional modifications as needed, i.e. the carbonyl or amine groups may be altered or protected.

In an alternative embodiment, the attachment is any number of different Z linkers, including amide and amine linkages, as is generally depicted in Structure 19 using uridine as the base and a Structure 3 oligomer:

Structure 19

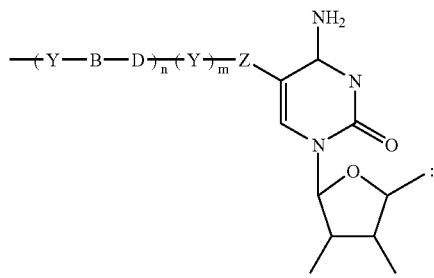

In this embodiment, Z is a linker. Preferably, Z is a short linker of about 1 to about 10 atoms, with from 1 to 5 atoms being preferred, that may or may not contain alkene, alkynyl, amine, amide, azo, imine, etc., bonds. Linkers are known in the art; for example, homo-or hetero-bifunctional linkers as are well known (see 1994 Pierce Chemical Company catalog, technical section on cross-linkers, pages 155–200, incorporated herein by reference). Preferred Z linkers include, but are not limited to, alkyl groups (including substituted alkyl groups and alkyl groups containing heteroatom moieties), with short alkyl groups, esters, amide, amine, epoxy groups and ethylene glycol and derivatives being preferred, with propyl, acetylene, and $C_2$ alkene being especially preferred. Z may also be a sulfone group, forming sulfonamide linkages as discussed below.

In a preferred embodiment, the attachment of the nucleic acid and the conductive oligomer is done via attachment to the backbone of the nucleic acid. This may be done in a number of ways, including attachment to a ribose of the ribose-phosphate backbone, or to the phosphate of the backbone, or other groups of analogous backbones.

As a preliminary matter, it should be understood that the site of attachment in this embodiment may be to a 3' or 5' terminal nucleotide, or to an internal nucleotide, as is more fully described below.

In a preferred embodiment, the conductive oligomer is attached to the ribose of the ribose-phosphate backbone. This may be done in several ways. As is known in the art, nucleosides that are modified at either the 2' or 3' position of the ribose with amino groups, sulfur groups, silicone groups, phosphorus groups, or oxo groups can be made (Imazawa et al., J. Org. Chem., 44:2039 (1979); Hobbs et al., J. Org. Chem. 42(4):714 (1977); Verheyden et al., J. Orrg. Chem. 36(2):250 (1971); McGee et al., J. Org. Chem. 61:781–785 (1996); Mikhailopulo et al., Liebigs. Ann. Chem. 513–519 (1993); McGee et al., Nucleosides & Nucleotides 14(6): 1329 (1995), all of which are incorporated by reference). These modified nucleosides are then used to add the conductive oligomers.

A preferred embodiment utilizes amino-modified nucleosides. These amino-modified riboses can then be used to form either amide or amine linkages to the conductive oligomers. In a preferred embodiment, the amino group is attached directly to the ribose, although as will be appreciated by those in the art, short linkers such as those described herein for "Z" may be present between the amino group and the ribose.

In a preferred embodiment, an amide linkage is used for attachment to the ribose. Preferably, if the conductive oligomer of Structures 1–3 is used, m is zero and thus the conductive oligomer terminates in the amide bond. In this embodiment, the nitrogen of the amino group of the amino-modified ribose is the "D" atom of the conductive oligomer. Thus, a preferred attachment of this embodiment is depicted in Structure 20 (using the Structure 3 conductive oligomer):

Structure 20

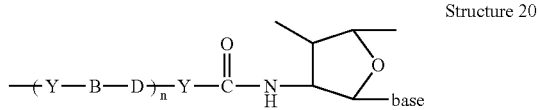

As will be appreciated by those in the art, Structure 20 has the terminal bond fixed as an amide bond.

In a preferred embodiment, a heteroatom linkage is used, i.e. oxo, amine, sulfur, etc. A preferred embodiment utilizes an amine linkage. Again, as outlined above for the amide linkages, for amine linkages, the nitrogen of the amino-modified ribose may be the "D" atom of the conductive oligomer when the Structure 3 conductive oligomer is used. Thus, for example, Structures 21 and 22 depict nucleosides with the Structures 3 and 9 conductive oligomers, respectively, using the nitrogen as the heteroatom, athough other heteroatoms can be used:

Structure 21

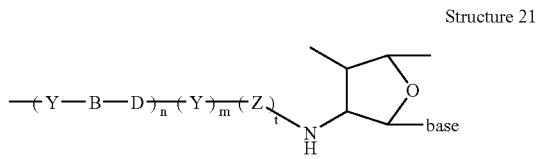

In Structure 21, preferably both m and t are not zero. A preferred Z here is a methylene group, or other aliphatic alkyl linkers. One, two or three carbons in this position are particularly useful for synthetic reasons.

Structure 22

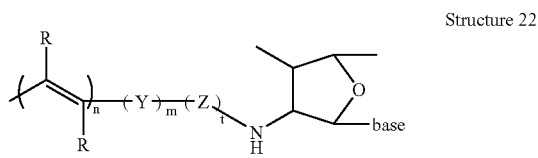

In Structure 22, Z is as defined above. Suitable linkers include methylene and ethylene.

In an alternative embodiment, the conductive oligomer is covalently attached to the nucleic acid via the phosphate of the ribose-phosphate backbone (or analog) of a nucleic acid. In this embodiment, the attachment is direct, utilizes a linker or via an amide bond. Structure 23 depicts a direct linkage, and Structure 24 depicts linkage via an amide bond (both utilize the Structure 3 conductive oligomer, although Structure 8 conductive oligomers are also possible). Structures 23 and 24 depict the conductive oligomer in the 3' position, although the 5' position is also possible. Furthermore, both Structures 23 and 24 depict naturally occurring phosphodiester bonds, although as those in the art will appreciate, non-standard analogs of phosphodiester bonds may also be used.

Structure 23

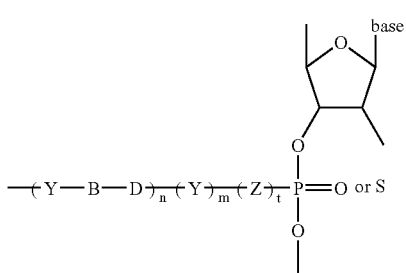

In Structure 23, if the terminal Y is present (i.e. m=1), then preferably Z is not present (i.e. t=0). If the terminal Y is not present, then Z is preferably present.

Structure 24 depicts a preferred embodiment, wherein the terminal B-D bond is an amide bond, the terminal Y is not present, and Z is a linker, as defined herein.

Structure 24

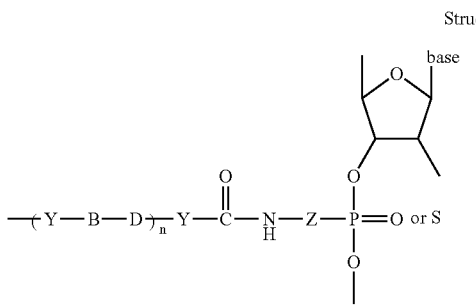

In a preferred embodiment, the conductive oligomer is covalently attached to the nucleic acid via a transition metal ligand. In this embodiment, the conductive oligomer is covalently attached to a ligand which provides one or more of the coordination atoms for a transition metal. In one embodiment, the ligand to which the conductive oligomer is attached also has the nucleic acid attached, as is generally depicted below in Structure 25. Alternatively, the conductive oligomer is attached to one ligand, and the nucleic acid is attached to another ligand, as is generally depicted below in Structure 26. Thus, in the presence of the transition metal, the conductive oligomer is covalently attached to the nucleic acid. Both of these structures depict Structure 3 conductive oligomers, although other oligomers may be utilized. Structures 25 and 26 depict two representative structures:

Structure 25

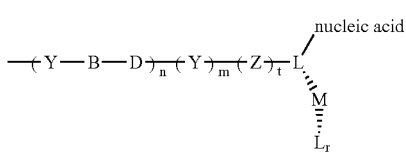

Structure 26

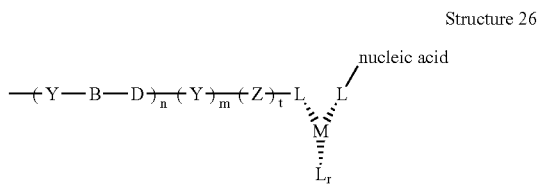

In the structures depicted herein, M is a metal atom, with transition metals being preferred. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinium (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, are preferred. Particularly preferred are ruthenium, rhenium, osmium, platinium, cobalt and iron.

L are the co-ligands, that provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the L from the terminus of the conductive oligomer, the L contributed from the nucleic acid, and r, add up to six. Thus, when the metal has a coordination number of six, r may range from zero (when all coordination atoms are provided by the other two ligands) to four, when all the co-ligands are monodentate. Thus generally, r will be from 0 to 8, depending on the coordination number of the metal ion and the choice of the other ligands.

In one embodiment, the metal ion has a coordination number of six and both the ligand attached to the conductive oligomer and the ligand attached to the nucleic acid are at least bidentate; that is, r is preferably zero, one (i.e. the remaining co-ligand is bidentate) or two (two monodentate co-ligands are used).

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma (σ) donors) and organometallic ligands such as metallocene ligands (generally referred to in the literature as pi (π) donors, and depicted herein as $L_m$). Suitable nitrogen donating ligands are well known in the art and include, but are not limited to, $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetraazacyclotetradecane (abbreviated cyclam), EDTA, EGTA and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp 73–98), 21.1 (pp. 813–898) and 21.3 (pp 915–957), all of which are hereby expressly incorporated by reference.

Suitable sigma donating ligands using carbon, oxygen, sulfur and phosphorus are known in the art. For example, suitable sigma carbon donors are found in Cotton and Wilkenson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkenson.

The oxygen, sulfur, phosphorus and nitrogen-donating ligands are attached in such a manner as to allow the heteroatoms to serve as coordination atoms.

In a preferred embodiment, organometallic ligands are used. In addition to purely organic compounds for use as redox moieties, and various transition metal coordination complexes with δ-bonded organic ligand with donor atoms as heterocyclic or exocyclic substituents, there is available a wide variety of transition metal organometallic compounds with π-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982–1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion [$C_5H_5$(−1)] and various ring substituted and ring fused derivatives, such as the indenylide (−1) ion, that yield a class of bis(cyclopentadieyl) metal compounds, (i.e. the metallocenes); see for example Robins et al., J. Am. Chem. Soc. 104:1882–1893 (1982); and Gassman et al., J. Am. Chem. Soc. 108:4228–4229 (1986), incorporated by reference. Of these, ferrocene [($C_5H_5$)$_2$Fe] and its derivatives are prototypical examples which have been used in a wide variety of chemical (Connelly et al., Chem. Rev. 96:877–910 (1996), incorporated by reference) and electrochemical (Geiger et al., Advances in Organometallic Chemistry 23:1–93; and Geiger et al., Advances in Organometallic Chemistry 24:87, incorporated by reference) electron transfer or "redox" reactions. Metallocene derivatives of a variety of the first, second and third row transition metals are potential candidates as redox moieties that are covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene)chromium is a prototypical example, Other acyclic π-bonded ligands such as the allyl(−1) ion, or butadiene yield potentially suitable organometallic compounds, and all such ligands, in conduction with other π-bonded and δ-bonded ligands constitute the general class of organometallic compounds in which there is a metal to carbon bond. Electrochemical studies of various dimers and oligomers of such compounds with bridging organic ligands, and additional non-bridging ligands, as well as with and without metal—metal bonds are potential candidate redox moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized.

As described herein, any combination of ligands may be used. Preferred combinations include: a) all ligands are nitrogen donating ligands; b) all ligands are organometallic ligands; and c) the ligand at the terminus of the conductive oligomer is a metallocene ligand and the ligand provided by the nucleic acid is a nitrogen donating ligand, with the other ligands, if needed, are either nitrogen donating ligands or metallocene ligands, or a mixture. These combinations are depicted in representative structures using the conductive oligomer of Structure 3 are depicted in Structures 27 (using phenanthroline and amino as representative ligands), 28 (using ferrocene as the metal-ligand combination) and 29 (using cyclopentadienyl and amino as representative ligands).

Structure 27

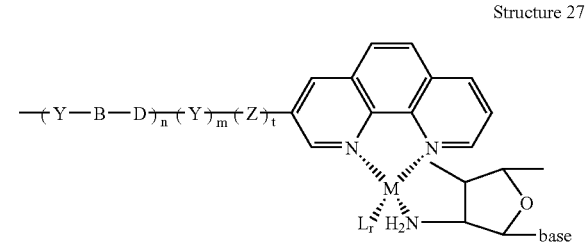

Structure 28

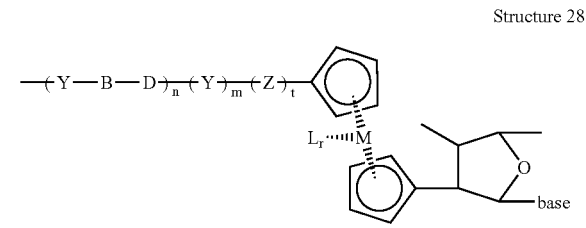

Structure 29

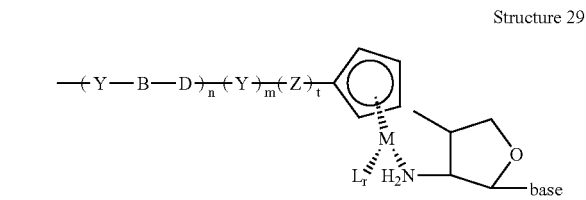

In a preferred embodiment, the ligands used in the invention show altered fluoroscent properties depending on the redox state of the chelated metal ion. As described below, this thus serves as an additional mode of detection of electron transfer between the ETM and the electrode.

In addition, similar methods can be used to attach proteins to the detection electrode; see for example U.S. Pat. No. 5,620,850, hereby incorporated by reference.

In a preferred embodiment, as is described more fully below, the ligand attached to the nucleic acid is an amino group attached to the 2' or 3' position of a ribose of the ribose-phosphate backbone. This ligand may contain a multiplicity of amino groups so as to form a polydentate ligand which binds the metal ion. Other preferred ligands include cyclopentadiene and phenanthroline.

The use of metal ions to connect the nucleic acids can serve as an internal control or calibration of the system, to evaluate the number of available nucleic acids on the surface. However, as will be appreciated by those in the art, if metal ions are used to connect the nucleic acids to the conductive oligomers, it is generally desirable to have this metal ion complex have a different redox potential than that of the ETMs used in the rest of the system, as described below. This is generally true so as to be able to distinguish the presence of the capture probe from the presence of the target sequence. This may be useful for identification, calibration and/or quantification. Thus, the amount of capture probe on an electrode may be compared to the amount of hybridized double stranded nucleic acid to quantify the amount of target sequence in a sample. This is quite significant to serve as an internal control of the sensor or system. This allows a measurement either prior to the addition of target or after, on the same molecules that will be used for detection, rather than rely on a similar but different control system. Thus, the actual molecules that will be used for the detection can be quantified prior to any experiment. This is a significant advantage over prior methods.

In a preferred embodiment, the capture probe nucleic acids (or other binding ligands) are covalently attached to the electrode via an insulator. The attachment of nucleic acids (and other binding ligands) to insulators such as alkyl groups is well known, and can be done to the base or the backbone, including the ribose or phosphate for backbones containing these moieties, or to alternate backbones for nucleic acid analogs.

In a preferred embodiment, there may be one or more different capture probe species on the surface. In some embodiments, there may be one type of capture probe, or one type of capture probe extender, as is more fully described below. Alternatively, different capture probes, or one capture probes with a multiplicity of different capture extender probes can be used. Similarly, it may be desirable (particular in the case of nucleic acid analytes and binding ligands in mechanism-2 systems) to use auxiliary capture probes that comprise relatively short probe sequences, that can be used to "tack down" components of the system, for example the recruitment linkers, to increase the concentration of ETMs at the surface.

Thus the present invention provides substrates comprising at least one detection electrode comprising monolayers and capture binding ligands, useful in target analyte detection systems.

In a preferred embodiment, the compositions further comprise a solution or soluble binding ligand, although as is more fully described below, for mechanism-1 systems, the ETMs may be added in the form of non-covalently attached hybridization indicators. Solution binding ligands are similar to capture binding ligands, in that they bind, preferably specifically, to target analytes. The solution binding ligand may be the same or different from the capture binding ligand. Generally, the solution binding ligands are not directed attached to the surface, although as depicted in FIG. 5A they may be. The solution binding ligand either directly comprises a recruitment linker that comprises at least one ETM (FIG. 4A), or the recruitment linker binds, either directly (FIG. 4A) or indirectly (FIG. 4E), to the solution binding ligand.

Thus, "solution binding ligands" or "soluble binding ligands" or "signal carriers" or "label probes" or "label binding ligands" with recruitment linkers comprising covalently attached ETMs are provided.

That is, one portion of the label probe or solution binding ligand directly or indirectly binds to the target analyte, and one portion comprises a recruitment linker comprising covalently attached ETMs. In some systems, for example in mechanism-1 nucleic acid systems, these may be the same. Similarly, for mechanism-1 systems, the recruitment linker comprises nucleic acid that will hybridize to detection probes. The terms "electron donor moiety", "electron acceptor moiety", and "ETMs" (ETMs) or grammatical equivalents herein refers to molecules capable of electron transfer under certain conditions. It is to be understood that electron donor and acceptor capabilities are relative; that is, a molecule which can lose an electron under certain experimental conditions will be able to accept an electron under different experimental conditions. It is to be understood that the number of possible electron donor moieties and electron acceptor moieties is very large, and that one skilled in the art of electron transfer compounds will be able to utilize a number of compounds in the present invention. Preferred ETMs include, but are not limited to, transition metal complexes, organic ETMs, and electrodes.

In a preferred embodiment, the ETMs are transition metal complexes. Transition metals are those whose atoms have a partial or complete d shell of electrons. Suitable transition metals for use in the invention are listed above.

The transition metals are complexed with a variety of ligands, L, defined above, to form suitable transition metal complexes, as is well known in the art.

In addition to transition metal complexes, other organic electron donors and acceptors may be covalently attached to the nucleic acid for use in the invention. These organic molecules include, but are not limited to, riboflavin, xanthene dyes, azine dyes, acridine orange, N,N'-dimethyl-2,7-diazapyrenium dichloride ($DAP^{2+}$), methylviologen, ethidium bromide, quinones such as N,N'-dimethylanthra(2, 1,9-def:6,5,10-d'e'f')diisoquinoline dichloride ($ADIQ^{2+}$); porphyrins ([meso-tetrakis(N-methyl-x-pyridinium)porphyrin tetrachloride], varlamine blue B hydrochloride, Bindschedler's green; 2,6-dichloroindophenol, 2,6-dibromophenolindophenol; Brilliant crest blue (3-amino-9-dimethylamino-10-methylphenoxyazine chloride), methylene blue; Nile blue A (aminoaphthodiethylaminophenoxazine sulfate), indigo-5,5',7,7'-tetrasulfonic acid, indigo-5,5',7-trisulfonic acid; phenosafranine, indigo-5-monosulfonic acid; safranine T; bis(dimethylglyoximato)-iron(II) chloride; induline scarlet, neutral red, anthracene, coronene, pyrene, 9-phenylanthracene, rubrene, binaphthyl, DPA, phenothiazene, fluoranthene, phenanthrene, chrysene, 1,8-diphenyl-1,3,5,7-octatetracene, naphthalene, acenaphthalene, perylene, TMPD and analogs and subsitituted derivatives of these compounds.

In one embodiment, the electron donors and acceptors are redox proteins as are known in the art. However, redox proteins in many embodiments are not preferred.

In one embodiment, particularly when an electrophoresis step is used, the ETMs are chosen to be charged molecules, preferably when the target analyte is not charged. Thus, for example, solution binding ligands that either directly or indirectly contain a number of charged ETMs can be bound to the target analyte prior to electrophoresis, to allow the target analyte to have a sufficient charge to move within the electric field, thus providing a dual purpose of providing charge and a detection moiety. Thus for example, label probes that contain charged ETMs may be used, that bind either directly to the target analyte or to an intermediate species such as an amplifier probe can be used. Alternatively, other charged species can be added in addition to the ETMs. Alternatively, these charges species may also be an integral part of the system; for example, part of the label probe may be a charged polymer such as polylysine. However, in this embodiment, the migration of non-specifically bound label probes to the detection surface can result in an increase in non-specific signals. Therefore, in this embodiment, the use of a reverse electric field (generally a pulse of reverse polarity) after electrophoresis can result in the non-specifically bound label probes being driven off or away from the detection probe surface, to decrease the background non-specific signal.

The choice of the specific ETMs will be influenced by the type of electron transfer detection used, as is generally outlined below. Preferred ETMs are metallocenes, with ferrocene, including derivatives, being particularly preferred.

In a preferred embodiment, a plurality of ETMs are used. As is shown in the examples, the use of multiple ETMs provides signal amplification and thus allows more sensitive detection limits. As discussed below, while the use of multiple ETMs on nucleic acids that hybridize to complementary strands can cause decreases in $T_m$s of the hybridization complexes depending on the number, site of attachment and spacing between the multiple ETMs, this is not a factor when the ETMs are on the recruitment linker (i.e. "mechanism-2" systems), since this does not hybridize to a complementary sequence. Accordingly, pluralities of ETMs are preferred, with at least about 2 ETMs per recruitment linker being preferred, and at least about 10 being particularly preferred, and at least about 20 to 50 being especially preferred. In some instances, very large numbers of ETMs (50 to 1000) can be used.

Thus, solution binding ligands, or label probes, with covalently attached ETMs are provided. The method of attachment of the ETM to the solution binding ligand will vary depending on the mode of detection (i.e. mechanism-1 or -2 systems) and the composition of the solution binding ligand. As is more fully outlined below, in mechanism-2 systems, the portion of the solution binding ligand (or label probe) that comprises the ETM is referred to as a "recruitment linker" and can comprise either nucleic acid or non-nucleic acid. For mechanism-1 systems, the recruitment linker must be nucleic acid.

Thus, as will be appreciated by those in the art, there are a variety of configurations that can be used. In a preferred embodiment, the recruitment linker is nucleic acid (including analogs), and attachment of the ETMs can be via (1) a base; (2) the backbone, including the ribose, the phosphate, or comparable structures in nucleic acid analogs; (3) nucleoside replacement, described below; or (4) metallocene polymers, as described below. In a preferred embodiment, the recruitment linker is non-nucleic acid, and can be either a metallocene polymer or an alkyl-type polymer (including heteroalkyl, as is more fully described below) containing ETM substitution groups. These options are generally depicted in FIG. 7.

In a preferred embodiment, the recruitment linker is a nucleic acid, and comprises covalently attached ETMs. The ETMs may be attached to nucleosides within the nucleic acid in a variety of positions. Preferred embodiments include, but are not limited to, (1) attachment to the base of the nucleoside, (2) attachment of the ETM as a base replacement, (3) attachment to the backbone of the nucleic acid, including either to a ribose of the ribose-phosphate backbone or to a phosphate moiety, or to analogous structures in nucleic acid analogs, and (4) attachment via metallocene polymers.

In addition, as is described below, when the recruitment linker is nucleic acid, it may be desirable to use secondary label probes, that have a first portion that will hybridize to a portion of the primary label probes and a second portion comprising a recruitment linker as is defined herein. This is generally depicted in FIGS. 6Q and 6R; this is similar to the use of an amplifier probe, except that both the primary and the secondary label probes comprise ETMs.

In a preferred embodiment, the ETM is attached to the base of a nucleoside as is generally outlined above for attachment of the conductive oligomer. Attachment can be to an internal nucleoside or a terminal nucleoside.

The covalent attachment to the base will depend in part on the ETM chosen, but in general is similar to the attachment of conductive oligomers to bases, as outlined above. Attachment may generally be done to any position of the base. In a preferred embodiment, the ETM is a transition metal complex, and thus attachment of a suitable metal ligand to the base leads to the covalent attachment of the ETM. Alternatively, similar types of linkages may be used for the attachment of organic ETMs, as will be appreciated by those in the art.

In one embodiment, the C4 attached amino group of cytosine, the C6 attached amino group of adenine, or the C2 attached amino group of guanine may be used as a transition metal ligand.

Ligands containing aromatic groups can be attached via acetylene linkages as is known in the art (see Comprehensive Organic Synthesis, Trost et al., Ed., Pergamon Press, Chapter 2.4: Coupling Reactions Between Sp$^2$ and sp Carbon Centers, Sonogashira, pp 521–549, and pp950–953, hereby incorporated by reference). Structure 30 depicts a representative structure in the presence of the metal ion and any other necessary ligands; Structure 30 depicts uridine, although as for all the structures herein, any other base may also be used.

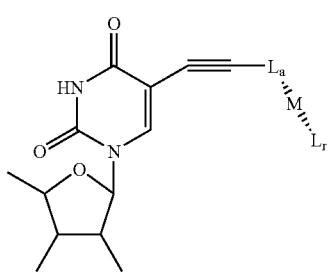

Structure 30

$L_a$ is a ligand, which may include nitrogen, oxygen, sulfur or phosphorus donating ligands or organometallic ligands such as metallocene ligands. Suitable $L_a$ ligands include, but not limited to, phenanthroline, imidazole, bpy and terpy. $L_r$ and M are as defined above. Again, it will be appreciated by those in the art, a linker ("Z") may be included between the nucleoside and the ETM.

Similarly, as for the conductive oligomers, the linkage may be done using a linker, which may utilize an amide linkage (see generally Telser et al., J. Am. Chem. Soc. 111:7221–7226 (1989); Telser et al., J. Am. Chem. Soc. 111:7226–7232 (1989), both of which are expressly incorporated by reference). These structures are generally depicted below in Structure 31, which again uses uridine as the base, although as above, the other bases may also be used:

Structure 31

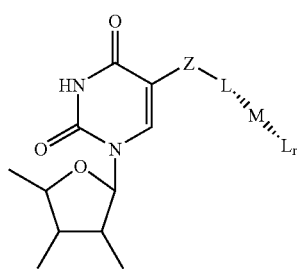

In this embodiment, L is a ligand as defined above, with $L_r$ and M as defined above as well. Preferably, L is amino, phen, byp and terpy.

In a preferred embodiment, the ETM attached to a nucleoside is a metallocene; i.e. the L and $L_r$ of Structure 31 are both metallocene ligands, $L_m$, as described above. Structure 32 depicts a preferred embodiment wherein the metallocene is ferrocene, and the base is uridine, although other bases may be used:

Structure 32

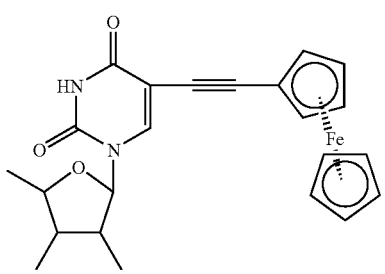

Preliminary data suggest that Structure 32 may cyclize, with the second acetylene carbon atom attacking the carbonyl oxygen, forming a furan-like structure. Preferred metallocenes include ferrocene, cobaltocene and osmiumocene.

In a preferred embodiment, the ETM is attached to a ribose at any position of the ribose-phosphate backbone of the nucleic acid, i.e. either the 5' or 3' terminus or any internal nucleoside. Ribose in this case can include ribose analogs. As is known in the art, nucleosides that are modified at either the 2' or 3' position of the ribose can be made, with nitrogen, oxygen, sulfur and phosphorus-containing modifications possible. Amino-modified and oxygen-modified ribose is preferred. See generally PCT publication WO 95/15971, incorporated herein by reference. These modification groups may be used as a transition metal ligand, or as a chemically functional moiety for attachment of other transition metal ligands and organometallic ligands, or organic electron donor moieties as will be appreciated by those in the art. In this embodiment, a linker such as depicted herein for "Z" may be used as well, or a conductive oligomer between the ribose and the ETM. Preferred embodiments utilize attachment at the 2' or 3' position of the ribose, with the 2' position being preferred. Thus for example, the conductive oligomers depicted in Structure 13, 14 and 15 may be replaced by ETMs; alternatively, the ETMs may be added to the free terminus of the conductive oligomer.

In a preferred embodiment, a metallocene serves as the ETM, and is attached via an amide bond as depicted below in Structure 33. The examples outline the synthesis of a preferred compound when the metallocene is ferrocene.

Structure 33

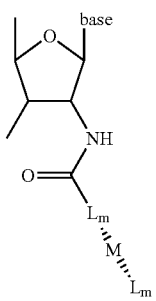

In a preferred embodiment, amine linkages are used, as is generally depicted in Structure 34.

Structure 34

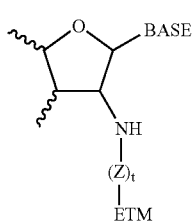

Z is a linker, as defined herein, with 1–16 atoms being preferred, and 2–4 atoms being particularly preferred, and t is either one or zero.

In a preferred embodiment, oxo linkages are used, as is generally depicted in Structure 35.

Structure 35

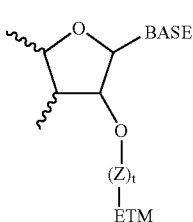

In Structure 35, Z is a linker, as defined herein, and t is either one or zero. Preferred Z linkers include alkyl groups including heteroalkyl groups such as $(CH_2)n$ and $(CH_2CH_2O)n$, with n from 1 to 10 being preferred, and n=1 to 4 being especially preferred, and n=4 being particularly preferred.

Linkages utilizing other heteroatoms are also possible.

In a preferred embodiment, an ETM is attached to a phosphate at any position of the ribose-phosphate backbone of the nucleic acid. This may be done in a variety of ways. In one embodiment, phosphodiester bond analogs such as phosphoramide or phosphoramidite linkages may be incorporated into a nucleic acid, where the heteroatom (i.e. nitrogen) serves as a transition metal ligand (see PCT publication WO 95/15971, incorporated by reference). Alternatively, the conductive oligomers depicted in Structures 23 and 24 may be replaced by ETMs. In a preferred embodiment, the composition has the structure shown in Structure 36.

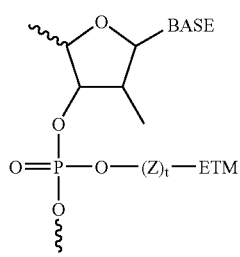

Structure 36

In Structure 36, the ETM is attached via a phosphate linkage, generally through the use of a linker, Z. Preferred Z linkers include alkyl groups, including heteroalkyl groups such as $(CH_2)_n$, $(CH_2CH_2O)_n$, with n from 1 to 10 being preferred, and n=1 to 4 being especially preferred, and n=4 being particularly preferred.

In mechanism-2 systems, when the ETM is attached to the base or the backbone of the nucleoside, it is possible to attach the ETMs via "dendrimer" structures, as is more fully outlined below. As is generally depicted in FIG. 8, alkyl-based linkers can be used to create multiple branching structures comprising one or more ETMs at the terminus of each branch. Generally, this is done by creating branch points containing multiple hydroxy groups, which optionally can then be used to add additional branch points. The terminal hydroxy groups can then be used in phosphoramidite reactions to add ETMs, as is generally done below for the nucleoside replacement and metallocene polymer reactions.

In a preferred embodiment, an ETM such as a metallocene is used as a "nucleoside replacement", serving as an ETM. For example, the distance between the two cyclopentadiene rings of ferrocene is similar to the orthongonal distance between two bases in a double stranded nucleic acid. Other metallocenes in addition to ferrocene may be used, for example, air stable metallocenes such as those containing cobalt or ruthenium. Thus, metallocene moieties may be incorporated into the backbone of a nucleic acid, as is generally depicted in Structure 37 (nucleic acid with a ribose-phosphate backbone) and Structure 38 (peptide nucleic acid backbone). Structures 37 and 38 depict ferrocene, although as will be appreciated by those in the art, other metallocenes may be used as well. In general, air stable metallocenes are preferred, including metallocenes utilizing ruthenium and cobalt as the metal.

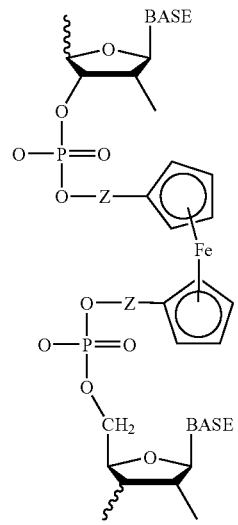

Structure 37

In Structure 37, Z is a linker as defined above, with generally short, alkyl groups, including heteroatoms such as oxygen being preferred. Generally, what is important is the length of the linker, such that minimal perturbations of a double stranded nucleic acid is effected, as is more fully described below. Thus, methylene, ethylene, ethylene glycols, propylene and butylene are all preferred, with ethylene and ethylene glycol being particularly preferred. In addition, each Z linker may be the same or different. Structure 37 depicts a ribose-phosphate backbone, although as will be appreciated by those in the art, nucleic acid analogs may also be used, including ribose analogs and phosphate bond analogs.

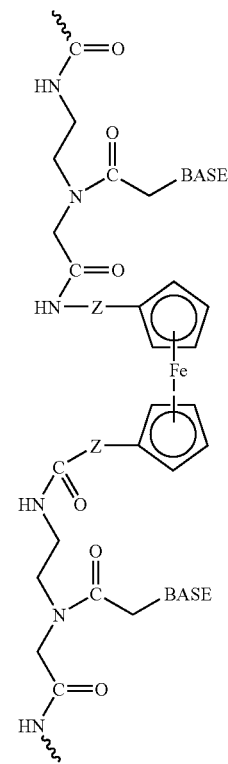

Structure 38

In Structure 38, preferred Z groups are as listed above, and again, each Z linker can be the same or different. As above, other nucleic acid analogs may be used as well.

In addition, although the structures and discussion above depicts metallocenes, and particularly ferrocene, this same general idea can be used to add ETMs in addition to metallocenes, as nucleoside replacements or in polymer embodiments, described below. Thus, for example, when the ETM is a transition metal complex other than a metallocene, comprising one, two or three (or more) ligands, the ligands can be functionalized as depicted for the ferrocene to allow the addition of phosphoramidite groups. Particularly preferred in this embodiment are complexes comprising at least two ring (for example, aryl and substituted aryl) ligands, where each of the ligands comprises functional groups for attachment via phosphoramidite chemistry. As will be appreciated by those in the art, this type of reaction, creating polymers of ETMs either as a portion of the backbone of the nucleic acid or as "side groups" of the nucleic acids, to allow amplification of the signals generated herein, can be done with virtually any ETM that can be functionalized to contain the correct chemical groups.

Thus, by inserting a metallocene such as ferrocene (or other ETM) into the backbone of a nucleic acid, nucleic acid analogs are made; that is, the invention provides nucleic acids having a backbone comprising at least one metallocene. This is distinguished from nucleic acids having metallocenes attached to the backbone, i.e. via a ribose, a phosphate, etc. That is, two nucleic acids each made up of a traditional nucleic acid or analog (nucleic acids in this case including a single nucleoside), may be covalently attached to each other via a metallocene. Viewed differently, a metallocene derivative or substituted metallocene is provided, wherein each of the two aromatic rings of the metallocene has a nucleic acid substitutent group.

In addition, as is more fully outlined below, it is possible to incorporate more than one metallocene into the backbone, either with nucleotides in between and/or with adjacent metallocenes. When adjacent metallocenes are added to the backbone, this is similar to the process described below as "metallocene polymers"; that is, there are areas of metallocene polymers within the backbone.

In addition to the nucleic acid substitutent groups, it is also desirable in some instances to add additional substituent groups to one or both of the aromatic rings of the metallocene (or ETM). For example, as these nucleoside replacements are generally part of probe sequences to be hybridized with a substantially complementary nucleic acid, for example a target sequence or another probe sequence, it is possible to add substitutent groups to the metallocene rings to facilitate hydrogen bonding to the base or bases on the opposite strand. These may be added to any position on the metallocene rings. Suitable substitutent groups include, but are not limited to, amide groups, amine groups, carboxylic acids, and alcohols, including substituted alcohols. In addition, these substitutent groups can be attached via linkers as well, although in general this is not preferred.

In addition, substituent groups on an ETM, particularly metallocenes such as ferrocene, may be added to alter the redox properties of the ETM. Thus, for example, in some embodiments, as is more fully described below, it may be desirable to have different ETMs attached in different ways (i.e. base or ribose attachment), on different probes, or for different purposes (for example, calibration or as an internal standard). Thus, the addition of substituent groups on the metallocene may allow two different ETMs to be distinguished.

In order to generate these metallocene-backbone nucleic acid analogs, the intermediate components are also provided. Thus, in a preferred embodiment, the invention provides phosphoramidite metallocenes, as generally depicted in Structure 39:

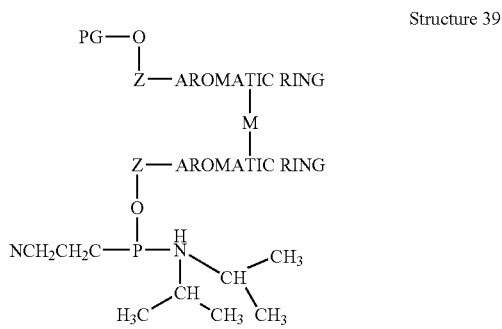

Structure 39

In Structure 39, PG is a protecting group, generally suitable for use in nucleic acid synthesis, with DMT, MMT and TMT all being preferred. The aromatic rings can either be the rings of the metallocene, or aromatic rings of ligands for transition metal complexes or other organic ETMs. The aromatic rings may be the same or different, and may be substituted as discussed herein. Structure 40 depicts the ferrocene derivative:

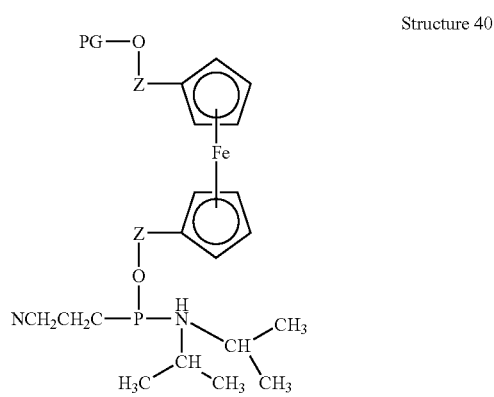

Structure 40

These phosphoramidite analogs can be added to standard oligonucleotide syntheses as is known in the art.

Structure 41 depicts the ferrocene peptide nucleic acid (PNA) monomer, that can be added to PNA synthesis as is known in the art:

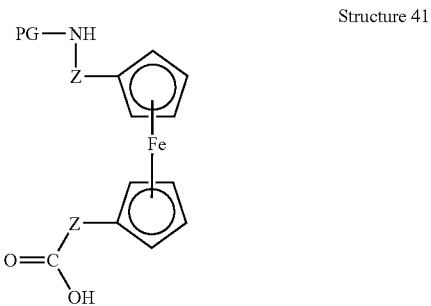

Structure 41

In Structure 41, the PG protecting group is suitable for use in peptide nucleic acid synthesis, with MMT, boc and Fmoc being preferred.

These same intermediate compounds can be used to form ETM or metallocene polymers, which are added to the nucleic acids, rather than as backbone replacements, as is more fully described below.

In a preferred embodiment, particularly for use in mechanism-2 systems, the ETMs are attached as polymers, for example as metallocene polymers, in a "branched" configuration similar to the "branched DNA" embodiments herein and as outlined in U.S. Pat. No. 5,124,246, using modified functionalized nucleotides. The general idea is as follows. A modified phosphoramidite nucleotide is generated that can ultimately contain a free hydroxy group that can be used in the attachment of phosphoramidite ETMs such as metallocenes. This free hydroxy group could be on the base or the backbone, such as the ribose or the phosphate (although as will be appreciated by those in the art, nucleic acid analogs containing other structures can also be used). The modified nucleotide is incorporated into a nucleic acid, and any hydroxy protecting groups are removed, thus leaving the free hydroxyl. Upon the addition of a phosphoramidite ETM such as a metallocene, as described above in structures 39 and 40, ETMs, such as metallocene ETMs, are added. Additional phosphoramidite ETMs such as metallocenes can be added, to form "ETM polymers", including "metallocene polymers" as depicted in FIG. 9 with ferrocene. In addition, in some embodiments, it is desirable to increase the solubility of the polymers by adding a "capping" group to the terminal ETM in the polymer, for example a final phosphate group to the metallocene as is generally depicted in FIG. 9. Other suitable solubility enhancing "capping" groups will be appreciated by those in the art. It should be noted that these solubility enhancing groups can be added to the polymers in other places, including to the ligand rings, for example on the metallocenes as discussed herein A preferred embodiment of this general idea is outlined in the Figures. In this embodiment, the 2' position of a ribose of a phosphoramidite nucleotide is first functionalized to contain a protected hydroxy group, in this case via an oxo-linkage, although any number of linkers can be used, as is generally described herein for Z linkers. The protected modified nucleotide is then incorporated via standard phosphoramidite chemistry into a growing nucleic acid. The protecting group is removed, and the free hydroxy group is used, again using standard phosphoramidite chemistry to add a phosphoramidite metallocene such as ferrocene. A similar reaction is possible for nucleic acid analogs. For example, using peptide nucleic acids and the metallocene monomer shown in Structure 41, peptide nucleic acid structures containing metallocene polymers could be generated.

Thus, the present invention provides recruitment linkers of nucleic acids comprising "branches" of metallocene polymers as is generally depicted in FIGS. 8 and 9. Preferred embodiments also utilize metallocene polymers from one to about 50 metallocenes in length, with from about 5 to about 20 being preferred and from about 5 to about 10 being especially preferred.

In addition, when the recruitment linker is nucleic acid, any combination of ETM attachments may be done. In general, as outlined herein, when mechanism-1 systems are used, clusters of nucleosides containing ETMs can decrease the Tm of hybridization of the probe to its target sequence; thus in general, for mechanism-1 systems, the ETMs are spaced out over the length of the sequence, or only small numbers of them are used.

In mechanism-1 systems, non-covalently attached ETMs may be used. In one embodiment, the ETM is a hybridization indicator. Hybridization indicators serve as an ETM that will preferentially associate with double stranded nucleic acid is added, usually reversibly, similar to the method of Millan et al., Anal. Chem. 65:2317–2323 (1993); Millan et al., Anal. Chem. 662943–2948 (1994), both of which are hereby expressly incorporated by reference. In this embodiment, increases in the local concentration of ETMs, due to the association of the ETM hybridization indicator with double stranded nucleic acid at the surface, can be monitored using the monolayers comprising the conductive oligomers. Hybridization indicators include intercalators and minor and/or major groove binding moieties. In a preferred embodiment, intercalators may be used; since intercalation generally only occurs in the presence of double stranded nucleic acid, only in the presence of double stranded nucleic acid will the ETMs concentrate. Intercalating transition metal complex ETMs are known in the art. Similarly, major or minor groove binding moieties, such as methylene blue, may also be used in this embodiment.

In addition, the binding acceleration systems of the invention may be used in virtually any method that relies on electrochemical detection of target analytes, with particular utility in nucleic acid detection. For example, the methods and compositions of the invention can be used in nucleic acid detection methods that rely on the detection of ETMs that are inherent to the target analyte. For example, as is generally described in Napier et al., Bioconj. Chem. 8:906 (1997), hereby expressly incorporated by reference, the guanine bases of nucleic acid can be detected via changes in the redox state, i.e. guanine oxidation by ruthenium complexes. Similarly, the methods of the invention find use in detection systems that utilize copper surfaces as catalytic electrodes to oxidize the riboses of nucleic acids.

In a preferred embodiment, the recruitment linker is not nucleic acid, and instead may be any sort of linker or polymer. As will be appreciated by those in the art, generally any linker or polymer that can be modified to contain ETMs can be used. In general, the polymers or linkers should be reasonably soluble and contain suitable functional groups for the addition of ETMs.

As used herein, a "recruitment polymer" comprises at least two or three subunits, which are covalently attached. At least some portion of the monomeric subunits contain functional groups for the covalent attachment of ETMs. In some embodiments coupling moieties are used to covalently link the subunits with the ETMs. Preferred functional groups for attachment are amino groups, carboxy groups, oxo groups and thiol groups, with amino groups being particularly preferred. As will be appreciated by those in the art, a wide variety of recruitment polymers are possible.

Suitable linkers include, but are not limited to, alkyl linkers (including heteroalkyl (including (poly)ethylene glycol-type structures), substituted alkyl, aryalkyl linkers, etc. As above for the polymers, the linkers will comprise one or more functional groups for the attachment of ETMs, which will be done as will be appreciated by those in the art, for example through the use homo-or hetero-bifunctional linkers as are well known (see 1994 Pierce Chemical Company catalog, technical section on cross-linkers, pages 155–200, incorporated herein by reference).

Suitable recruitment polymers include, but are not limited to, functionalized styrenes, such as amino styrene, functionalized dextrans, and polyamino acids. Preferred polymers are polyamino acids (both poly-D-amino acids and poly-L-amino acids), such as polylysine, and polymers containing lysine and other amino acids being particularly preferred. As outlined above, in some embodiments, charged recruitment linkers are preferred, for example when non-charged target analytes are to be detected. Other suitable polyamino acids are polyglutamic acid, polyaspartic acid, co-polymers of lysine and glutamic or aspartic acid, co-polymers of lysine with alanine, tyrosine, phenylalanine, serine, tryptophan, and/or proline.

In a preferred embodiment, the recruitment linker comprises a metallocene polymer, as is described above.

The attachment of the recruitment linkers to the first portion of the label probe, i.e. the portion that binds either directly or indirectly to the target analyte, will depend on the composition of the recruitment linker, as will be appreciated by those in the art. When the recruitment linker is nucleic acid, it is generally formed during the synthesis of the first portion of the label probe, with incorporation of nucleosides containing ETMs as required. Alternatively, the first portion of the label probe and the recruitment linker may be made separately, and then attached. For example, there may be an overlapping section of complementarity, forming a section of double stranded nucleic acid that can then be chemically crosslinked, for example by using psoralen as is known in the art.

When non-nucleic acid recruitment linkers are used, attachment of the linker/polymer of the recruitment linker will be done generally using standard chemical techniques, such as will be appreciated by those in the art. For example, when alkyl-based linkers are used, attachment can be similar to the attachment of insulators to nucleic acids.

In addition, it is possible to have recruitment linkers that are mixtures of nucleic acids and non-nucleic acids, either in a linear form (i.e. nucleic acid segments linked together with alkyl linkers) or in branched forms (nucleic acids with alkyl "branches" that may contain ETMs and may be additionally branched).

In a preferred embodiment, for example when the target analyte is a nucleic acid, it is the target sequence itself that carries the ETMs, rather than the recruitment linker of a label probe. For example, as is more fully described below, it is possible to enzymatically add triphosphate nucleotides comprising the ETMs of the invention to a growing nucleic acid, for example during a polymerase chain reaction (PCR). As will be recognized by those in the art, while several enzymes have been shown to generally tolerate modified nucleotides, some of the modified nucleotides of the invention, for example the "nucleoside replacement" embodiments and putatively some of the phosphate attachments, may or may not be recognized by the enzymes to allow incorporation into a growing nucleic acid. Therefore, preferred attachments in this embodiment are to the base or ribose of the nucleotide.

Thus, for example, PCR amplification of a target sequence, as is well known in the art, will result in target sequences comprising ETMs, generally randomly incorporated into the sequence. The system of the invention can then be configured to allow detection using these ETMs, as is generally depicted in FIGS. 6A and 6B.

Alternatively, as outlined more fully below, it is possible to enzymatically add nucleotides comprising ETMs to the terminus of a nucleic acid, for example a target nucleic acid. In this embodiment, an effective "recruitment linker" is added to the terminus of the target sequence, that can then be used for detection, as is generally depicted in FIG. 6Q. Thus the invention provides compositions utilizing electrodes comprising monolayers of conductive oligomers and capture probes, and target sequences that comprises a first portion that is capable of hybridizing to a component of an assay complex, and a second portion that does not hybridize to a component of an assay complex and comprises at least one covalently attached electron transfer moiety. Similarly, methods utilizing these compositions are also provided.

It is also possible to have ETMs connected to probe sequences, i.e. sequences designed to hybridize to complementary sequences, i.e. in mechanism-1 sequences, although this may also be used in mechanism-2 systems. Thus, ETMs may be added to non-recruitment linkers as well. For example, there may be ETMs added to sections of label probes that do hybridize to components of the assay complex, for example the first portion, or to the target sequence as outlined above and depicted in FIG. 6R. These ETMs may be used for electron transfer detection in some embodiments, or they may not, depending on the location and system. For example, in some embodiments, when for example the target sequence containing randomly incorporated ETMs is hybridized directly to the capture probe, as is depicted in FIGS. 6A and 6B, there may be ETMs in the portion hybridizing to the capture probe. If the capture probe is attached to the electrode using a conductive oligomer, these ETMs can be used to detect electron transfer as has been previously described. Alternatively, these ETMs may not be specifically detected.

Similarly, in some embodiments, when the recruitment linker is nucleic acid, it may be desirable in some instances to have some or all of the recruitment linker be double stranded, for example in the mechanism-2 systems. In one embodiment, there may be a second recruitment linker, substantially complementary to the first recruitment linker, that can hybridize to the first recruitment linker. In a preferred embodiment, the first recruitment linker comprises the covalently attached ETMs. In an alternative embodiment, the second recruitment linker contains the ETMs, and the first recruitment linker does not, and the ETMs are recruited to the surface by hybridization of the second recruitment linker to the first. In yet another embodiment, both the first and second recruitment linkers comprise ETMs. It should be noted, as discussed above, that nucleic acids comprising a large number of ETMs may not hybridize as well, i.e. the $T_m$ may be decreased, depending on the site of attachment and the characteristics of the ETM. Thus, in general, when multiple ETMs are used on hybridizing strands, i.e. in mechanism-1 systems, generally there are less than about 5, with less than about 3 being preferred, or alternatively the ETMs should be spaced sufficiently far apart that the intervening nucleotides can sufficiently hybridize to allow good kinetics.

In a preferred embodiment, the compositions of the invention are used to detect target analytes in a sample. In a preferred embodiment, the target analyte is a nucleic acid, and target sequences are detected. The term "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art. The target sequence may also be comprised of different target domains; for example, a first target domain of the sample target sequence may hybridize to a capture probe or a portion of capture extender probe, a second target domain may hybridize to a portion of an amplifier probe, a label probe, or a different capture or capture extender probe, etc. The target domains may be adjacent or separated. The terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

If required, the target analyte is prepared using known techniques. For example, the sample may be treated to lyse the cells, using known lysis buffers, electroporation, etc., with purification and/or amplification such as PCR occuring as needed, as will be appreciated by those in the art.

For nucleic acid systems, the probes of the present invention are designed to be complementary to a target sequence (either the target sequence of the sample or to other probe sequences, as is described below), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions.

Generally, the nucleic acid compositions of the invention are useful as oligonucleotide probes. As is appreciated by those in the art, the length of the probe will vary with the length of the target sequence and the hybridization and wash conditions. Generally, oligonucleotide probes range from about 8 to about 50 nucleotides, with from about 10 to about 30 being preferred and from about 12 to about 25 being especially preferred. In some cases, very long probes may be used, e.g. 50 to 200–300 nucleotides in length. Thus, in the structures depicted herein, nucleosides may be replaced with nucleic acids.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

The hybridization conditions may also vary when a nonionic backbone, i.e. PNA is used, as is known in the art. In addition, cross-linking agents may be added after target binding to cross-link, i.e. covalently attach, the two strands of the hybridization complex.

As will be appreciated by those in the art, the systems of the invention may take on a large number of different configurations, as is generally depicted in FIGS. 3, 4, 5 and 6. In general, there are three types of systems that can be used: (1) systems in which the target sequence itself is labeled with ETMs (see FIGS. 4A, 5A, 5B and 5D; this is generally useful for nucleic acid systems); (2) systems in which label probes directly bind to the target analytes (see FIGS. 4C and 4H for nucleic acid examples and FIGS. 6A, 6B, 6D and 6E, for examples of non-nucleic acid analytes); and (3) systems in which label probes are indirectly bound to the target sequences, for example through the use of amplifier probes (see FIGS. 4C, 5E, 5F and 5G for nucleic acid examples and FIG. 6C for representative non-nucleic acid target analytes).

In all three of these systems, it is preferred, although not required, that the target sequence be immobilized on the electrode surface. This is preferably done using capture probes and optionally one or more capture extender probes; see FIG. 3 for representative nucleic acid examples. When only capture probes are utilized, it is necessary to have unique capture probes for each target sequence; that is, the surface must be customized to contain unique capture probes. Alternatively, capture extender probes may be used, that allow a "universal" surface, i.e. a surface containing a single type of capture probe that can be used to detect any target sequence. "Capture extender" probes are generally depicted in FIGS. 4C, 5C, 5E, 5G and 5H, as well as FIG. 6B, etc., and have a first portion that will hybridize to all or part of the capture probe, and a second portion that will hybridize to a portion of the target sequence. This then allows the generation of customized soluble probes, which as will be appreciated by those in the art is generally simpler and less costly. As shown herein, two capture extender probes may be used. This has generally been done to stabilize assay complexes (for example when the target sequence is large, or when large amplifier probes (particularly branched or dendrimer amplifier probes) are used.

While the discussion and figures herein generally depict nucleic acid embodiments, these same ideas can be used for non-nucleic acid target analytes. For example, capture extender ligands can be generated, as will be appreciated by those in the art. For example, a nucleic acid "tail" can be added to a binding ligand, as is generally depicted in FIG. 6B.

In a preferred embodiment, the binding ligands are added after the formation of the SAM ((4) above). This may be done in a variety of ways, as will be appreciated by those in the art. In one embodiment, conductive oligomers with terminal functional groups are made, with preferred embodiments utilizing activated carboxylates and isothiocyanates, that will react with primary amines that are either present or put onto the binding ligand such as a nucleic acid, using an activated carboxylate. These two reagents have the advantage of being stable in aqueous solution, yet react with primary alkylamines. However, the primary aromatic amines and secondary and tertiary amines of the bases should not react, thus allowing site specific addition of nucleic acids to the surface. Similar techniques can be used with non-nucleic acid components; for example, as outlined above, the attachment of proteins to SAMs comprising metal chelates is known; see U.S. Pat. No. 5,620,850. This allows the spotting of probes (either capture or detection probes, or both) using known methods (ink jet, spotting, etc.) onto the surface.

In addition, there are a number of non-nucleic acid methods that can be used to immobilize a nucleic acid on a surface. For example, binding partner pairs can be utilized; i.e. one binding partner is attached to the terminus of the conductive oligomer, and the other to the end of the nucleic acid. This may also be done without using a nucleic acid capture probe; that is, one binding partner serves as the capture probe and the other is attached to either the target sequence or a capture extender probe. That is, either the target sequence comprises the binding partner, or a capture extender probe that will hybridize to the target sequence comprises the binding partner. Suitable binding partner pairs include, but are not limited to, hapten pairs such as biotin/streptavidin; antigens/antibodies; NTA/histidine tags; etc. In general, smaller binding partners are preferred, such that the electrons can pass from the nucleic acid into the conductive oligomer to allow detection.

In a preferred embodiment, when the target sequence itself is modified to contain a binding partner, the binding partner is attached via a modified nucleotide that can be enzymatically attached to the target sequence, for example during a PCR target amplification step. Alternatively, the binding partner should be easily attached to the target sequence.

Alternatively, a capture extender probe may be utilized that has a nucleic acid portion for hybridization to the target as well as a binding partner (for example, the capture extender probe may comprise a non-nucleic acid portion such as an alkyl linker that is used to attach a binding partner). In this embodiment, it may be desirable to cross-link the double-stranded nucleic acid of the target and capture extender probe for stability, for example using psoralen as is known in the art.

In one embodiment, the target is not bound to the electrode surface using capture probes. In this embodiment, what is important, as for all the assays herein, is that excess label probes be removed prior to detection and that the assay complex (the recruitment linker) be in proximity to the surface. As will be appreciated by those in the art, this may be accomplished in other ways. For example, the assay complex may be present on beads that are added to the electrode comprising the monolayer. The recruitment linkers comprising the ETMs may be placed in proximity to the conductive oligomer surface using techniques well known in the art, including gravity settling of the beads on the surface, electrostatic or magnetic interactions between bead components and the surface, using binding partner attachment as outlined above. Alternatively, after the removal of excess reagents such as excess label probes, the assay complex may be driven down to the surface, for example via electrophoresis as is outlined herein.

However, preferred embodiments utilize assay complexes attached via nucleic acid capture probes.

In a preferred embodiment, the target sequence itself contains the ETMs. As discussed above, this may be done using target sequences that have ETMs incorporated at any number of positions, as outlined above. In this embodiment, as for the others of the system, the 3'–5' orientation of the probes and targets is chosen to get the ETM-containing structures (i.e. recruitment linkers or target sequences) as close to the surface of the monolayer as possible, and in the correct orientation. This may be done using attachment via insulators or conductive oligomers as is generally shown in the Figures. In addition, as will be appreciated by those in the art, multiple capture probes can be utilized, either in a configuration such as depicted in FIG. 5D, wherein the 5'–3' orientation of the capture probes is different, or where "loops" of target form when multiples of capture probes are used.

In a preferred embodiment, the label probes directly hybridize to the target sequences, as is generally depicted in the figures. In these embodiments, the target sequence is preferably, but not required to be, immobilized on the surface using capture probes, including capture extender probes. Label probes are then used to bring the ETMs into proximity of the surface of the monolayer comprising conductive oligomers. In a preferred embodiment, multiple label probes are used; that is, label probes are designed such that the portion that hybridizes to the target sequence can be different for a number of different label probes, such that amplification of the signal occurs, since multiple label probes can bind for every target sequence. Thus, as depicted in the figures, n is an integer of at least one. Depending on the sensitivity desired, the length of the target sequence, the number of ETMs per label probe, etc., preferred ranges of n are from 1 to 50, with from about 1 to about 20 being particularly preferred, and from about 2 to about 5 being especially preferred. In addition, if "generic" label probes are desired, label extender probes can be used as generally described below for use with amplifier probes.

As above, generally in this embodiment the configuration of the system and the label probes are designed to recruit the ETMs as close as possible to the monolayer surface.

In a preferred embodiment, the label probes are hybridized to the target sequence indirectly. That is, the present invention finds use in novel combinations of signal amplification technologies and electron transfer detection on electrodes, which may be particularly useful in sandwich hybridization assays, as generally depicted in the Figures for nucleic acid embodiments; similar systems can be developed for non-nucleic acid target analytes. In these embodiments, the amplifier probes of the invention are bound to the target sequence in a sample either directly or indirectly. Since the amplifier probes preferably contain a relatively large number of amplification sequences that are available for binding of label probes, the detectable signal is significantly increased, and allows the detection limits of the target to be significantly improved. These label and amplifier probes, and the detection methods described herein, may be used in essentially any known nucleic acid hybridization formats, such as those in which the target is bound directly to a solid phase or in sandwich hybridization assays in which the target is bound to one or more nucleic acids that are in turn bound to the solid phase.

In general, these embodiments may be described as follows with particular reference to nucleic acids. An amplifier probe is hybridized to the target sequence, either directly (e.g. FIGS. 4C and 5E), or through the use of a label extender probe (e.g. FIGS. 5F and 5G), which serves to allow "generic" amplifier probes to be made. The target sequence is preferably, but not required to be, immobilized on the electrode using capture probes. Preferably, the amplifier probe contains a multiplicity of amplification sequences, although in some embodiments, as described below, the amplifier probe may contain only a single amplification sequence. The amplifier probe may take on a number of different forms; either a branched conformation, a dendrimer conformation, or a linear "string" of amplification sequences. These amplification sequences are used to form hybridization complexes with label probes, and the ETMs can be detected using the electrode.

Accordingly, the present invention provides assay complexes comprising at least one amplifier probe. By "amplifier probe" or "nucleic acid multimer" or "amplification multimer" or grammatical equivalents herein is meant a nucleic acid probe that is used to facilitate signal amplification. Amplifier probes comprise at least a first single-stranded nucleic acid probe sequence, as defined below, and at least one single-stranded nucleic acid amplification sequence, with a multiplicity of amplification sequences being preferred.

Figure 5E:
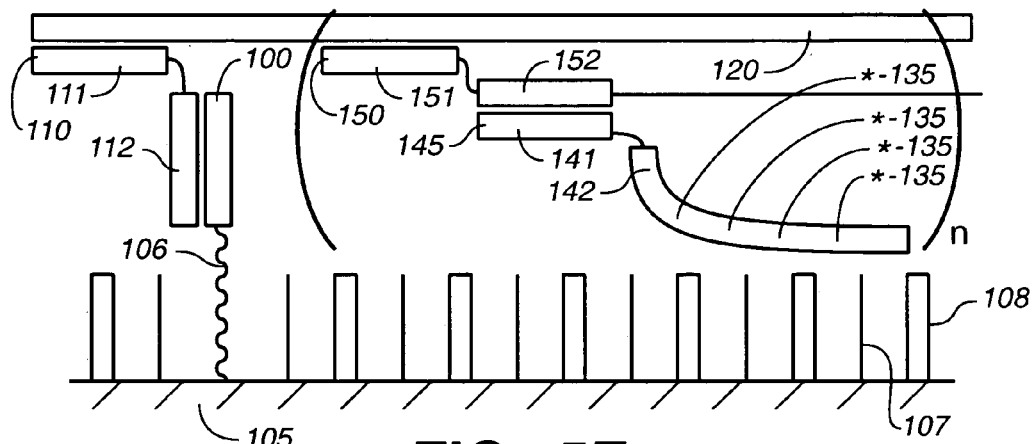

Amplifier probes comprise a first probe sequence that is used, either directly or indirectly, to hybridize to the target sequence. That is, the amplifier probe itself may have a first probe sequence that is substantially complementary to the target sequence (e.g. FIG. 5E), or it has a first probe sequence that is substantially complementary to a portion of an additional probe, in this case called a label extender probe, that has a first portion that is substantially complementary to the target sequence (e.g. FIGS. 5F and 5G). In a preferred embodiment, the first probe sequence of the amplifier probe is substantially complementary to the target sequence, as is generally depicted in FIG. 5E.

In general, as for all the probes herein, the first probe sequence is of a length sufficient to give specificity and stability. Thus generally, the probe sequences of the invention that are designed to hybridize to another nucleic acid (i.e. probe sequences, amplification sequences, portions or domains of larger probes) are at least about 5 nucleosides long, with at least about 10 being preferred and at least about 15 being especially preferred.

In a preferred embodiment, the amplifier probes, or any of the other probes of the invention, may form hairpin stem-loop structures in the absence of their target. The length of the stem double-stranded sequence will be selected such that the hairpin structure is not favored in the presence of target. The use of these type of probes, in the systems of the invention or in any nucleic acid detection systems, can result in a significant decrease in non-specific binding and thus an increase in the signal to noise ratio.

Generally, these hairpin structures comprise four components. The first component is a target binding sequence, i.e. a region complementary to the target (which may be the sample target sequence or another probe sequence to which binding is desired), that is about 10 nucleosides long, with about 15 being preferred. The second component is a loop sequence, that can facilitate the formation of nucleic acid loops. Particularly preferred in this regard are repeats of GTC, which has been identified in Fragile X Syndrome as forming turns. (When PNA analogs are used, turns comprising proline residues may be preferred). Generally, from three to five repeats are used, with four to five being preferred. The third component is a self-complementary region, which has a first portion that is complementary to a portion of the target sequence region and a second portion that comprises a first portion of the label probe binding sequence. The fourth component is substantially complementary to a label probe (or other probe, as the case may be). The fourth component further comprises a "sticky end", that is, a portion that does not hybridize to any other portion of the probe, and preferably contains most, if not all, of the ETMs. As will be appreciated by those in the art, the any or all of the probes described herein may be configured to form hairpins in the absence of their targets, including the amplifier, capture, capture extender, label and label extender probes.

In a preferred embodiment, several different amplifier probes are used, each with first probe sequences that will hybridize to a different portion of the target sequence. That is, there is more than one level of amplification; the amplifier probe provides an amplification of signal due to a multiplicity of labelling events, and several different amplifier probes, each with this multiplicity of labels, for each target sequence is used. Thus, preferred embodiments utilize at least two different pools of amplifier probes, each pool having a different probe sequence for hybridization to different portions of the target sequence; the only real limitation on the number of different amplifier probes will be the length of the original target sequence. In addition, it is also possible that the different amplifier probes contain different amplification sequences, although this is generally not preferred.

Figure 5F:
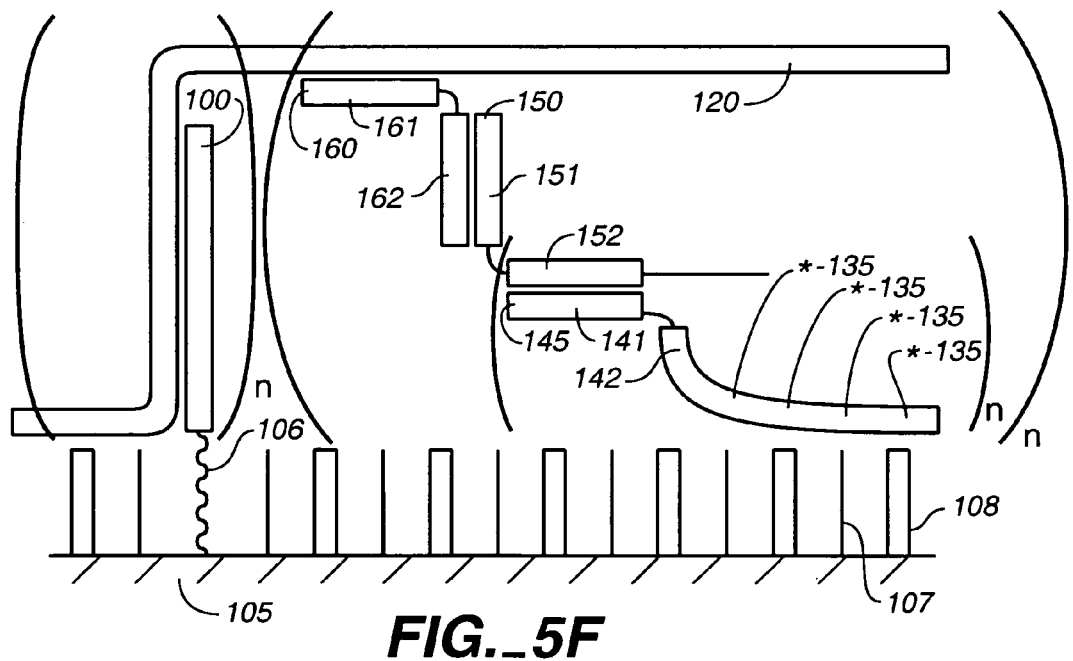

In a preferred embodiment, the amplifier probe does not hybridize to the sample target sequence directly, but instead hybridizes to a first portion of a label extender probe, as is generally depicted in FIG. 5F. This is particularly useful to allow the use of "generic" amplifier probes, that is, amplifier probes that can be used with a variety of different targets. This may be desirable since several of the amplifier probes require special synthesis techniques. Thus, the addition of a relatively short probe as a label extender probe is preferred. Thus, the first probe sequence of the amplifier probe is substantially complementary to a first portion or domain of a first label extender single-stranded nucleic acid probe. The label extender probe also contains a second portion or domain that is substantially complementary to a portion of the target sequence. Both of these portions are preferably at least about 10 to about 50 nucleotides in length, with a range of about 15 to about 30 being preferred. The terms "first" and "second" are not meant to confer an orientation of the sequences with respect to the 5'–3' orientation of the target or probe sequences. For example, assuming a 5'–3' orientation of the complementary target sequence, the first portion may be located either 5' to the second portion, or 3' to the second portion. For convenience herein, the order of probe sequences are generally shown from left to right.

In a preferred embodiment, more than one label extender probe-amplifier probe pair may be used, tht is, n is more than 1. That is, a plurality of label extender probes may be used, each with a portion that is substantially complementary to a different portion of the target sequence; this can serve as another level of amplification. Thus, a preferred embodiment utilizes pools of at least two label extender probes, with the upper limit being set by the length of the target sequence.

In a preferred embodiment, more than one label extender probe is used with a single amplifier probe to reduce non-specific binding, as is depicted in FIG. 5G and generally outlined in U.S. Pat. No. 5,681,697, incorporated by reference herein. In this embodiment, a first portion of the first label extender probe hybridizes to a first portion of the target sequence, and the second portion of the first label extender probe hybridizes to a first probe sequence of the amplifier probe. A first portion of the second label extender probe hybridizes to a second portion of the target sequence, and the second portion of the second label extender probe hybridizes to a second probe sequence of the amplifier probe. These form structures sometimes referred to as "cruciform" structures or configurations, and are generally done to confer stability when large branched or dendrimeric amplifier probes are used.

In addition, as will be appreciated by those in the art, the label extender probes may interact with a preamplifier probe, described below, rather than the amplifier probe directly.

Similarly, as outlined above, a preferred embodiment utilizes several different amplifier probes, each with first probe sequences that will hybridize to a different portion of the label extender probe. In addition, as outlined above, it is also possible that the different amplifier probes contain different amplification sequences, although this is generally not preferred.

In addition to the first probe sequence, the amplifier probe also comprises at least one amplification sequence. An "amplification sequence" or "amplification segment" or grammatical equivalents herein is meant a sequence that is used, either directly or indirectly, to bind to a first portion of a label probe as is more fully described below. Preferably, the amplifier probe comprises a multiplicity of amplification sequences, with from about 3 to about 1000 being preferred, from about 10 to about 100 being particularly preferred, and about 50 being especially preferred. In some cases, for example when linear amplifier probes are used, from 1 to about 20 is preferred with from about 5 to about 10 being particularly preferred.

The amplification sequences may be linked to each other in a variety of ways, as will be appreciated by those in the art. They may be covalently linked directly to each other, or to intervening sequences or chemical moieties, through nucleic acid linkages such as phosphodiester bonds, PNA bonds, etc., or through interposed linking agents such amino acid, carbohydrate or polyol bridges, or through other cross-linking agents or binding partners. The site(s) of linkage may be at the ends of a segment, and/or at one or more internal nucleotides in the strand. In a preferred embodiment, the amplification sequences are attached via nucleic acid linkages.

In a preferred embodiment, branched amplifier probes are used, as are generally described in U.S. Pat. No. 5,124,246, hereby incorporated by reference. Branched amplifier probes may take on "fork-like" or "comb-like" conformations. "Fork-like" branched amplifier probes generally have three or more oligonucleotide segments emanating from a point of origin to form a branched structure. The point of origin may be another nucleotide segment or a multifunctional molecule to whcih at least three segments can be covalently or tightly bound. "Comb-like" branched amplifier probes have a linear backbone with a multiplicity of sidechain oligonucleotides extending from the backbone. In either conformation, the pendant segments will normally depend from a modified nucleotide or other organic moiety having the appropriate functional groups for attachment of oligonucleotides. Furthermore, in either conformation, a large number of amplification sequences are available for binding, either directly or indirectly, to detection probes. In general, these structures are made as is known in the art, using modified multifunctional nucleotides, as is described in U.S. Pat. Nos. 5,635,352 and 5,124,246, among others.

In a preferred embodiment, dendrimer amplifier probes are used, as are generally described in U.S. Pat. No. 5,175,270, hereby expressly incorporated by reference. Dendrimeric amplifier probes have amplification sequences that are attached via hybridization, and thus have portions of double-stranded nucleic acid as a component of their structure. The outer surface of the dendrimer amplifier probe has a multiplicity of amplification sequences.

In a preferred embodiment, linear amplifier probes are used, that have individual amplification sequences linked end-to-end either directly or with short intervening sequences to form a polymer. As with the other amplifier configurations, there may be additional sequences or moieties between the amplification sequences. In addition, as outlined herein, linear amplification probes may form hairpin stem-loop structures, as is depicted in FIG. 12.

In one embodiment, the linear amplifier probe has a single amplification sequence. This may be useful when cycles of hybridization/disassociation occurs, forming a pool of amplifier probe that was hybridized to the target and then removed to allow more probes to bind, or when large numbers of ETMs are used for each label probe. However, in a preferred embodiment, linear amplifier probes comprise a multiplicity of amplification sequences.

In addition, the amplifier probe may be totally linear, totally branched, totally dendrimeric, or any combination thereof.

The amplification sequences of the amplifier probe are used, either directly or indirectly, to bind to a label probe to allow detection. In a preferred embodiment, the amplification sequences of the amplifier probe are substantially complementary to a first portion of a label probe. Alternatively, amplifier extender probes are used, that have a first portion that binds to the amplification sequence and a second portion that binds to the first portion of the label probe.

In addition, the compositions of the invention may include "preamplifier" molecules, which serves a bridging moiety between the label extender molecules and the amplifier probes. In this way, more amplifier and thus more ETMs are ultimately bound to the detection probes. Preamplifier molecules may be either linear or branched, and typically contain in the range of about 30–3000 nucleotides.

The reactions outlined below may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

Generally, the methods are as follows. In a preferred embodiment, the target is initially driven down to the vicinity of the detection probe using any one of the methods outlined above. In general, two methods may be employed; the assay complexes as described below are formed first (i.e. all the soluble components are added together, either simultaneously or sequentially, including capture extender probes, label probes, amplification probes, label extender probes, etc.), including any hybridization accelerators, and then the complex is added to the surface for binding to a detection electrode. Alternatively, the target may be added, hybridization acceleration occurs to allow the target to bind the capture binding ligand and then additional components are added to form the assay complex. The latter is described in detail below, but either procedure may be followed. Similarly, some components may be added, electrophoresed, and other components added; for example, the target analyte may be combined with any capture extender probes and then transported, etc. In addition, as outlined herein, electrophoretic steps may be used to effect "washing" steps, wherein excess reagents (non-bound analytes, excess probes, etc.) can be driven from the surface.

In a preferred embodiment, non-specific interactions can be decreased using several electrophoretic methods. In a preferred embodiment, label probes that are not specifically directly or indirectly bound to a target sequence can be removed from the surface by a pulse of an opposite electric field, i.e. the electric field is reversed for some period of time. The strength of the reverse electric field is chosen such that specifically bound label probes are not removed (or any of the other required components of the attachment and assay complexes).

In a preferred embodiment, for example when electrophoresis is used, the label probes or label binding ligands comprising the ETMs carry a charge opposite to the target analyte. This can be done either with nucleic acid label probes or charged solution binding ligands, although the discussion focuses on nucleic acid embodiments. This can be useful in two different systems. In a preferred embodiment, the target analyte carries a large excess of charge, i.e. a negative charge in the case of nucleic acid. The binding of one or more positively charged label probes does not significantly change the net negative charge on the target complex; that is, the target will still be attracted to the cathode. However, un-bound label probes, or label probes not specifically bound to the target, are repulsed, thus resulting in a decrease of non-specific binding. For example, PNA backbones can be modified to carry a net positive charge, and there are other nucleic acid analogs as known in the art that are positively charged.

In a preferred embodiment, the label probe is has a high amount of opposite charge, such that upon binding to the target analyte, the net charge of the target analyte changes. Thus, for example, for nucleic acids, the label probes carry a sufficient positive charge to render the label probe-target analyte complex positively charged. This results in the specific target analyte being drawn to the anode, but all other negatively charged elements, i.e. other nucleic acids, will be repulsed. This is particularly useful when there is an excess of other targets present; for example, when the target analyte is a minor species of a large excess of other nucleic acids, for example.

In a preferred embodiment, the target analyte is initially electrophoretically transported to the detection electrode, and then immobilized or attached to the detection electrode. In one embodiment, this is done by forming an attachment complex (frequently referred to herein as a hybridization complex when nucleic acid components are used) between a capture probe and a portion of the target analyte. A preferred embodiment utilizes capture extender binding ligands (also called capture extender probes herein); in this embodiment, an attachment complex is formed between a portion of the target sequence and a first portion of a capture extender probe, and an additional attachment complex between a second portion of the capture extender probe and a portion of the capture probe. Additional preferred embodiments utilize additional capture probes, thus forming an attachment complex between a portion of the target sequence and a first portion of a second capture extender probe, and an attachment complex between a second portion of the second capture extender probe and a second portion of the capture probe.

Alternatively, the attachment of the target sequence to the electrode is done simultaneously with the other reactions.

The method proceeds with the introduction of amplifier probes, if utilized. In a preferred embodiment, the amplifier probe comprises a first probe sequence that is substantially complementary to a portion of the target sequence, and at least one amplification sequence.

In one embodiment, the first probe sequence of the amplifier probe is hybridized to the target sequence, and any unhybridized amplifier probe is removed. This will generally be done as is known in the art, and depends on the type of assay. When the target sequence is immobilized on a surface such as an electrode, the removal of excess reagents generally is done via one or more washing steps, as will be appreciated by those in the art. In this embodiment, the target may be immobilized on any solid support. When the target sequence is not immobilized on a surface, the removal of excess reagents such as the probes of the invention may be done by adding beads (i.e. solid support particles) that contain complementary sequences to the probes, such that the excess probes bind to the beads. The beads can then be removed, for example by centrifugation, filtration, the application of magnetic or electrostatic fields, etc.

The reaction mixture is then subjected to conditions (temperature, high salt, changes in pH, etc.) under which the amplifier probe disassociates from the target sequence, and the amplifier probe is collected. The amplifier probe may then be added to an electrode comprising capture probes for the amplifier probes, label probes added, and detection is achieved.

In a preferred embodiment, a larger pool of probe is generated by adding more amplifier probe to the target sequence and the hybridization/disassociation reactions are repeated, to generate a larger pool of amplifier probe. This pool of amplifier probe is then added to an electrode comprising amplifier capture probes, label probes added, and detection proceeds.

In this embodiment, it is preferred that the target sequence be immobilized on a solid support, including an electrode, using the methods described herein; although as will be appreciated by those in the art, alternate solid support attachment technologies may be used, such as attachment to glass, polymers, etc. It is possible to do the reaction on one solid support and then add the pooled amplifier probe to an electrode for detection.

In a preferred embodiment, the amplifier probe comprises a multiplicity of amplification sequences.

In one embodiment, the first probe sequence of the amplifier probe is hybridized to the target sequence, and any unhybridized amplifier probe is removed. Again, preferred embodiments utilize immobilized target sequences, wherein the target sequences are immobilized by hybridization with capture probes that are attached to the electrode, or hybridization to capture extender probes that in turn hybridize with immobilized capture probes as is described herein. Generally, in these embodiments, the capture probes and the detection probes are immobilized on the electrode, generally at the same "address".

In a preferred embodiment, the first probe sequence of the amplifier probe is hybridized to a first portion of at least one label extender probe, and a second portion of the label extender probe is hybridized to a portion of the target sequence. Other preferred embodiments utilize more than one label extender probe, as is generally shown in FIG. 5G.

In a preferred embodiment, the amplification sequences of the amplifier probe are used directly for detection, by hybridizing at least one label probe sequence.

The invention thus provides assay complexes that minimally comprise a target sequence and a label probe. "Assay complex" herein is meant the collection of attachment or hybridization complexes comprising analytes, including binding ligands and targets, that allows detection. The composition of the assay complex depends on the use of the different probe component outlined herein. Thus, in FIG. 6A, the assay complex comprises the capture probe and the target sequence. The assay complexes may also include capture extender probes, label extender probes, and amplifier probes, as outlined herein, depending on the configuration used.

The assays are generally run under stringency conditions which allows formation of the label probe attachment complex only in the presence of target. Stringency can be controlled by altering a step parameter that is a thermodynamic variable, including, but not limited to, temperature, formamide concentration, salt concentration, chaotropic salt concentration pH, organic solvent concentration, etc. Stringency may also include the use of an electrophoretic step to drive non-specific (i.e. low stringency) materials away from the detection electrode.

These parameters may also be used to control non-specific binding, as is generally outlined in U.S. Pat. No. 5,681,697. Thus it may be desirable to perform certain steps at higher stringency conditions; for example, when an initial hybridization step is done between the target sequence and the label extender and capture extender probes. Running this step at conditions which favor specific binding can allow the reduction of non-specific binding.

In a preferred nucleic acid embodiment, when all of the components outlined herein are used, a preferred method is as follows. Single-stranded target sequence is incubated under hybridization conditions with the capture extender probes and the label extender probes. A preferred embodiment does this reaction in the presence of the electrode with immobilized capture probes, although this may also be done in two steps, with the initial incubation and the subsequent addition to the electrode. Excess reagents are washed off, and amplifier probes are then added. If preamplifier probes are used, they may be added either prior to the amplifier probes or simultaneously with the amplifier probes. Excess reagents are washed off, and label probes are then added. Excess reagents are washed off, and detection proceeds as outlined below.

In one embodiment, a number of capture probes (or capture probes and capture extender probes) that are each substantially complementary to a different portion of the target sequence are used.

Again, as outlined herein, when amplifier probes are used, the system is generally configured such that upon label probe binding, the recruitment linkers comprising the ETMs are placed in proximity either to the monolayer surface containing conductive oligomers (mechanism-2) or in proximity to detection probes. Thus for example, for mechanism-2 systems, when the ETMs are attached via "dendrimer" type structures as outlined herein, the length of the linkers from the nucleic acid point of attachment to the ETMs may vary, particularly with the length of the capture probe when capture extender probes are used. That is, longer capture probes, with capture extenders, can result in the target sequences being "held" further away from the surface than for shorter capture probes. Adding extra linking sequences between the probe nucleic acid and the ETMs can result in the ETMs being spatially closer to the surface, giving better results. Similarly, for mechanism-1 systems, the length of the recruitment linker, the length of the detection probe, and their distance, may be optimized.

In addition, if desirable, nucleic acids utilized in the invention may also be ligated together prior to detection, if applicable, by using standard molecular biology techniques such as the use of a ligase. Similarly, if desirable for stability, cross-linking agents may be added to hold the structures stable.

As will be appreciated by those in the art, while described for nucleic acids, the systems outlined herein can be used for other target analytes as well.

The compositions of the invention are generally synthesized as outlined below and in U.S. Ser. Nos. 08/743,798, 08/873,978, 08/911,085, 08/911,085, and PCT US97/20014, all of which are expressly incorporated by reference, generally utilizing techniques well known in the art. As will be appreciated by those in the art, many of the techniques outlined below are directed to nucleic acids containing a ribose-phosphate backbone. However, as outlined above, many alternate nucleic acid analogs may be utilized, some of which may not contain either ribose or phosphate in the backbone. In these embodiments, for attachment at positions other than the base, attachment is done as will be appreciated by those in the art, depending on the backbone. Thus, for example, attachment can be made at the carbon atoms of the PNA backbone, as is described below, or at either terminus of the PNA.

The compositions may be made in several ways. A preferred method first synthesizes a conductive oligomer attached to a nucleoside, with addition of additional nucleosides to form the capture probe followed by attachment to the electrode. Alternatively, the whole capture probe may be made and then the completed conductive oligomer added, followed by attachment to the electrode. Alternatively, a monolayer of conductive oligomer (some of which have functional groups for attachment of capture probes) is attached to the electrode first, followed by attachment of the capture probe. The latter two methods may be preferred when conductive oligomers are used which are not stable in the solvents and under the conditions used in traditional nucleic acid synthesis.

In a preferred embodiment, the compositions of the invention are made by first forming the conductive oligomer covalently attached to the nucleoside, followed by the addition of additional nucleosides to form a capture probe nucleic acid, with the last step comprising the addition of the conductive oligomer to the electrode.

The attachment of the conductive oligomer to the nucleoside may be done in several ways. In a preferred embodiment, all or part of the conductive oligomer is synthesized first (generally with a functional group on the end for attachment to the electrode), which is then attached to the nucleoside. Additional nucleosides are then added as required, with the last step generally being attachment to the electrode. Alternatively, oligomer units are added one at a time to the nucleoside, with addition of additional nucleosides and attachment to the electrode. A number of representative syntheses are shown in the Figures of WO 98/20162; PCT/US98112430; PCT/US98/12082; PCT/US99/01705; PCT/US99/01703; and U.S. Ser. Nos. 09/135,183; 60/105,875; and 09/295,691, all of which are incorporated by reference.

The conductive oligomer is then attached to a nucleoside that may contain one (or more) of the oligomer units, attached as depicted herein.

In a preferred embodiment, attachment is to a ribose of the ribose-phosphate backbone, including amide and amine linkages. In a preferred embodiment, there is at least a methylene group or other short aliphatic alkyl groups (as a Z group) between the nitrogen attached to the ribose and the aromatic ring of the conductive oligomer.

Alternatively, attachment is via a phosphate of the ribose-phosphate backbone, as generally outlined in PCT US97/20014.

In a preferred embodiment, attachment is via the base. In a preferred embodiment, protecting groups may be added to the base prior to addition of the conductive oligomers, as is generally known in the art. In addition, the palladium cross-coupling reactions may be altered to prevent dimerization problems; i.e. two conductive oligomers dimerizing, rather than coupling to the base.

Alternatively, attachment to the base may be done by making the nucleoside with one unit of the oligomer, followed by the addition of others.

Once the modified nucleosides are prepared, protected and activated, prior to attachment to the electrode, they may be incorporated into a growing oligonucleotide by standard synthetic techniques (Gait, Oligonucleotide Synthesis: A Practical Approach, IRL Press, Oxford, UK 1984; Eckstein) in several ways.

In one embodiment, one or more modified nucleosides are converted to the triphosphate form and incorporated into a growing oligonucleotide chain by using standard molecular biology techniques such as with the use of the enzyme DNA polymerase 1, T4 DNA polymerase, T7 DNA polymerase, Taq DNA polymerase, reverse transcriptase, and RNA polymerases. For the incorporation of a 3' modified nucleoside to a nucleic acid, terminal deoxynucleotidyltransferase may be used. (Ratliff, Terminal deoxynucleotidyltransferase. In The Enzymes, Vol 14A. P. D. Boyer ed. pp 105–118. Academic Press, San Diego, Calif. 1981). Thus, the present invention provides deoxyribonucleoside triphosphates comprising a covalently attached ETM. Preferred embodiments utilize ETM attachment to the base or the backbone, such as the ribose (preferably in the 2' position), as is generally depicted below in Structures 42 and 43:

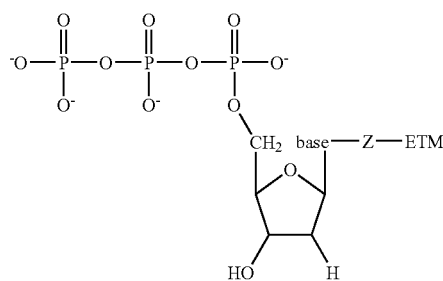

Structure 42

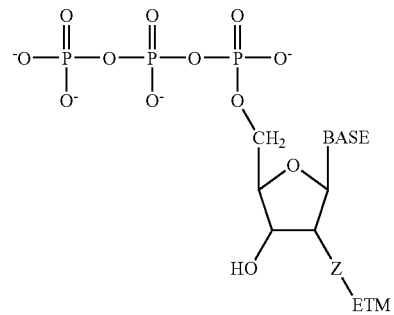

Structure 43

Thus, in some embodiments, it may be possible to generate the nucleic acids comprising ETMs in situ. For example, a target sequence can hybridize to a capture probe (for example on the surface) in such a way that the terminus of the target sequence is exposed, i.e. unhybridized. The addition of enzyme and triphosphate nucleotides labelled with ETMs allows the in situ creation of the label. Similarly, using labeled nucleotides recognized by polymerases can allow simultaneous PCR and detection; that is, the target sequences are generated in situ.

In a preferred embodiment, the modified nucleoside is converted to the phosphoramidite or H-phosphonate form, which are then used in solid-phase or solution syntheses of oligonucleotides. In this way the modified nucleoside, either for attachment at the ribose (i.e. amino- or thiol-modified nucleosides) or the base, is incorporated into the oligonucleotide at either an internal position or the 5' terminus. This is generally done in one of two ways. First, the 5' position of the ribose is protected with 4',4-dimethoxytrityl (DMT) followed by reaction with either 2-cyanoethoxy-bis-diisopropylaminophosphine in the presence of diisopropylammonium tetrazolide, or by reaction with chlorodiisopropylamino 2'-cyanoethyoxyphosphine, to give the phosphoramidite as is known in the art; although other techniques may be used as will be appreciated by those in the art. See Gait, supra; Caruthers, Science 230:281 (1985), both of which are expressly incorporated herein by reference.

For attachment of a group to the 3' terminus, a preferred method utilizes the attachment of the modified nucleoside (or the nucleoside replacement) to controlled pore glass (CPG) or other oligomeric supports. In this embodiment, the modified nucleoside is protected at the 5' end with DMT, and then reacted with succinic anhydride with activation. The resulting succinyl compound is attached to CPG or other oligomeric supports as is known in the art. Further phosphoramidite nucleosides are added, either modified or not, to the 5' end after deprotection. Thus, the present invention provides conductive oligomers or insulators covalently attached to nucleosides attached to solid oligomeric supports such as CPG, and phosphoramidite derivatives of the nucleosides of the invention.

The invention further provides methods of making label probes with recruitment linkers comprising ETMs. These synthetic reactions will depend on the character of the recruitment linker and the method of attachment of the ETM, as will be appreciated by those in the art. For nucleic acid recruitment linkers, the label probes are generally made as outlined herein with the incorporation of ETMs at one or more positions. When a transition metal complex is used as the ETM, synthesis may occur in several ways. In a preferred embodiment, the ligand(s) are added to a nucleoside, followed by the transition metal ion, and then the nucleoside with the transition metal complex attached is added to an oligonucleotide, i.e. by addition to the nucleic acid synthesizer. Alternatively, the ligand(s) may be attached, followed by incorporation into a growing oligonucleotide chain, followed by the addition of the metal ion.

In a preferred embodiment, ETMs are attached to a ribose of the ribose-phosphate backbone. This is generally done as is outlined herein for conductive oligomers, as described herein, and in PCT publication WO 95/15971, using amino-modified or oxo-modified nucleosides, at either the 2' or 3' position of the ribose. The amino group may then be used either as a ligand, for example as a transition metal ligand for attachment of the metal ion, or as a chemically functional group that can be used for attachment of other ligands or organic ETMs, for example via amide linkages, as will be appreciated by those in the art. For example, the examples describe the synthesis of nucleosides with a variety of ETMs attached via the ribose.

In a preferred embodiment, ETMs are attached to a phosphate of the ribose-phosphate backbone. As outlined herein, this may be done using phosphodiester analogs such as phosphoramidite bonds, see generally PCT publication WO 95/15971, or can be done in a similar manner to that described in PCT US97/20014, where the conductive oligomer is replaced by a transition metal ligand or complex or an organic ETM.

Attachment to alternate backbones, for example peptide nucleic acids or alternate phosphate linkages will be done as will be appreciated by those in the art.

In a preferred embodiment, ETMs are attached to a base of the nucleoside. This may be done in a variety of ways. In one embodiment, amino groups of the base, either naturally occurring or added as is described herein (see the fiigures, for example), are used either as ligands for transition metal complexes or as a chemically functional group that can be used to add other ligands, for example via an amide linkage, or organic ETMs. This is done as will be appreciated by those in the art. Alternatively, nucleosides containing halogen atoms attached to the heterocyclic ring are commercially available. Acetylene linked ligands may be added using the halogenated bases, as is generally known; see for example, Tzalis et al., Tetrahedron Lett. 36(34):6017–6020 (1995); Tzalis et al., Tetrahedron Lett. 36(2):3489–3490 (1995); and Tzalis et al., Chem. Communications (in press) 1996, all of which are hereby expressly incorporated by reference. See also the figures and the examples, which describes the synthesis of metallocenes (in this case, ferrocene) attached via acetylene linkages to the bases.

In one embodiment, the nucleosides are made with transition metal ligands, incorporated into a nucleic acid, and then the transition metal ion and any remaining necessary ligands are added as is known in the art. In an alternative embodiment, the transition metal ion and additional ligands are added prior to incorporation into the nucleic acid.

Once the nucleic acids of the invention are made, with a covalently attached attachment linker (i.e. either an insulator or a conductive oligomer), the attachment linker is attached to the electrode. The method will vary depending on the type of electrode used. As is described herein, the attachment linkers are generally made with a terminal "A" linker to facilitate attachment to the electrode. For the purposes of this application, a sulfur-gold attachment is considered a covalent attachment.

In a preferred embodiment, conductive oligomers, insulators, and attachment linkers are covalently attached via sulfur linkages to the electrode. However, surprisingly, traditional protecting groups for use of attaching molecules to gold electrodes are generally not ideal for use in both synthesis of the compositions described herein and inclusion in oligonucleotide synthetic reactions. Accordingly, the present invention provides novel methods for the attachment of conductive oligomers to gold electrodes, utilizing unusual protecting groups, including ethylpyridine, and trimethylsilylethyl as is depicted in the Figures. However, as will be appreciated by those in the art, when the conductive oligomers do not contain nucleic acids, traditional protecting groups such as acetyl groups and others may be used. See Greene et al., supra.

This may be done in several ways. In a preferred embodiment, the subunit of the conductive oligomer which contains the sulfur atom for attachment to the electrode is protected with an ethyl-pyridine or trimethylsilylethyl group. For the former, this is generally done by contacting the subunit containing the sulfur atom (preferably in the form of a sulfhydryl) with a vinyl pyridine group or vinyl trimethylsilylethyl group under conditions whereby an ethylpyridine group or trimethylsilylethyl group is added to the sulfur atom.

This subunit also generally contains a functional moiety for attachment of additional subunits, and thus additional subunits are attached to form the conductive oligomer. The conductive oligomer is then attached to a nucleoside, and additional nucleosides attached. The protecting group is then removed and the sulfur-gold covalent attachment is made. Alternatively, all or part of the conductive oligomer is made, and then either a subunit containing a protected sulfur atom is added, or a sulfur atom is added and then protected. The conductive oligomer is then attached to a nucleoside, and additional nucleosides attached. Alternatively, the conductive oligomer attached to a nucleic acid is made, and then either a subunit containing a protected sulfur atom is added, or a sulfur atom is added and then protected. Alternatively, the ethyl pyridine protecting group may be used as above, but removed after one or more steps and replaced with a standard protecting group like a disulfide. Thus, the ethyl pyridine or trimethylsilylethyl group may serve as the protecting group for some of the synthetic reactions, and then removed and replaced with a traditional protecting group.

By "subunit" of a conductive polymer herein is meant at least the moiety of the conductive oligomer to which the sulfur atom is attached, although additional atoms may be present, including either functional groups which allow the addition of additional components of the conductive oligomer, or additional components of the conductive oligomer. Thus, for example, when Structure 1 oligomers are used, a subunit comprises at least the first Y group.

A preferred method comprises 1) adding an ethyl pyridine or trimethylsilylethyl protecting group to a sulfur atom attached to a first subunit of a conductive oligomer, generally done by adding a vinyl pyridine or trimethylsilylethyl group to a sulfhydryl; 2) adding additional subunits to form the conductive oligomer; 3) adding at least a first nucleoside to the conductive oligomer; 4) adding additional nucleosides to the first nucleoside to form a nucleic acid; 5) attaching the conductive oligomer to the gold electrode. This may also be done in the absence of nucleosides, as is described in the Examples.

The above method may also be used to attach insulator molecules to a gold electrode.

In a preferred embodiment, a monolayer comprising conductive oligomers (and optionally insulators) is added to the electrode. Generally, the chemistry of addition is similar to or the same as the addition of conductive oligomers to the electrode, i.e. using a sulfur atom for attachment to a gold electrode, etc. Compositions comprising monolayers in addition to the conductive oligomers covalently attached to nucleic acids may be made in at least one of five ways: (1) addition of the monolayer, followed by subsequent addition of the attachment linker-nucleic acid complex; (2) addition of theattachment linker-nucleic acid complex followed by addition of the monolayer; (3) simultaneous addition of the monolayer and attachment linker-nucleic acid complex; (4) formation of a monolayer (using any of 1, 2 or 3) which includes attachment linkers which terminate in a functional moiety suitable for attachment of a completed nucleic acid; or (5) formation of a monolayer which includes attachment linkers which terminate in a functional moiety suitable for nucleic acid synthesis, i.e. the nucleic acid is synthesized on the surface of the monolayer as is known in the art. Such suitable functional moieties include, but are not limited to, nucleosides, amino groups, carboxyl groups, protected sulfur moieties, or hydroxyl groups for phosphoramidite additions. The examples describe the formation of a monolayer on a gold electrode using the preferred method (1).

In a preferred embodiment, the nucleic acid is a peptide nucleic acid or analog. In this embodiment, the invention provides peptide nucleic acids with at least one covalently attached ETM or attachment linker. In a preferred embodiment, these moieties are covalently attached to an monomeric subunit of the PNA. By "monomeric subunit of PNA" herein is meant the —NH—$CH_2CH_2$—N($COCH_2$-Base)-$CH_2$—CO-monomer, or derivatives (herein included within the definition of "nucleoside") of PNA. For example, the number of carbon atoms in the PNA backbone may be altered; see generally Nielsen et al., Chem. Soc. Rev. 1997 page 73, which discloses a number of PNA derivatives, herein expressly incorporated by reference. Similarly, the amide bond linking the base to the backbone may be altered; phosphoramide and sulfuramide bonds may be used. Alternatively, the moieties are attached to an internal monomeric subunit. By "internal" herein is meant that the monomeric subunit is not either the N-terminal monomeric subunit or the C-terminal monomeric subunit. In this embodiment, the moieties can be attached either to a base or to the backbone of the monomeric subunit. Attachment to the base is done as outlined herein or known in the literature. In general, the moieties are added to a base which is then incorporated into a PNA as outlined herein. The base may be either protected, as required for incorporation into the PNA synthetic reaction, or derivatized, to allow incorporation, either prior to the addition of the chemical substituent or afterwards. Protection and derivatization of the bases is shown in PCT US97/20014. The bases can then be incorporated into monomeric subunits.

In a preferred embodiment, the moieties are covalently attached to the backbone of the PNA monomer. The attachment is generally to one of the unsubstituted carbon atoms of the monomeric subunit, preferably the α-carbon of the backbone, although attachment at either of the carbon 1 or 2 positions, or the α-carbon of the amide bond linking the base to the backbone may be done. In the case of PNA analogs, other carbons or atoms may be substituted as well. In a preferred embodiment, moieties are added at the α-carbon atoms, either to a terminal monomeric subunit or an internal one.

In this embodiment, a modified monomeric subunit is synthesized with an ETM or an attachment linker, or a functional group for its attachment, and then the base is added and the modified monomer can be incorporated into a growing PNA chain.

Once generated, the monomeric subunits with covalently attached moieties are incorporated into a PNA using the techniques outlined in Will et al., Tetrahedron 51(44):12069–12082 (1995), and Vanderlaan et al., Tett. Let. 38:2249–2252 (1997), both of which are hereby expressly incorporated in their entirety. These procedures allow the addition of chemical substituents to peptide nucleic acids without destroying the chemical substituents.

As will be appreciated by those in the art, electrodes may be made that have any combination of nucleic acids, conductive oligomers and insulators.

The compositions of the invention may additionally contain one or more labels at any position. By "label" herein is meant an element (e.g. an isotope) or chemical compound that is attached to enable the detection of the compound. Preferred labels are radioactive isotopic labels, and colored or fluorescent dyes. The labels may be incorporated into the compound at any position. In addition, the compositions of the invention may also contain other moieties such as cross-linking agents to facilitate cross-linking of the target-probe complex. See for example, Lukhtanov et al., Nucl. Acids. Res. 24(4):683 (1996) and Tabone et al., Biochem. 33:375 (1994), both of which are expressly incorporated by reference.

Once made, the compositions find use in a number of applications, as described herein. In particular, the compositions of the invention find use in binding assays for the detection of target analytes, in particular nucleic acid target sequences. As will be appreciated by those in the art, electrodes can be made that have a single species of binding ligand, or multiple binding ligand species, i.e. in an array format.

In addition, as outlined herein, the use of a solid support such as an electrode enables the use of these assays in an array form. For example, the use of oligonucleotide arrays are well known in the art. In addition, techniques are known for "addressing" locations within an electrode and for the surface modification of electrodes. Thus, in a preferred embodiment, arrays of different binding ligands, including nucleic acids, are laid down on the electrode, each of which are covalently attached to the electrode via an attachment linker. In this embodiment, the number of different binding ligands may vary widely, from one to thousands, with from about 4 to about 100,000 being preferred, and from about 10 to about 10,000 being particularly preferred.

Once the assay complexes of the invention are made, that minimally comprise a target analyte and a label probe, detection proceeds with electronic initiation. Without being limited by the mechanism or theory, detection is based on the transfer of electrons from the ETM to the electrode, including via the "π-way".

Detection of electron transfer, i.e. the presence of the ETMs, is generally initiated electronically, with voltage being preferred. A potential is applied to the assay complex. Precise control and variations in the applied potential can be via a potentiostat and either a three electrode system (one reference, one sample (or working) and one counter electrode) or a two electrode system (one sample and one counter electrode). This allows matching of applied potential to peak potential of the system which depends in part on the choice of ETMs and in part on the conductive oligomer used, the composition and integrity of the monolayer, and what type of reference electrode is used. As described herein, ferrocene is a preferred ETM.

In a preferred embodiment, a co-reductant or co-oxidant (collectively, co-redoxant) is used, as an additional electron source or sink. See generally Sato et al., Bull. Chem. Soc. Jpn 66:1032 (1993); Uosaki et al., Electrochimica Acta 36:1799 (1991); and Alleman et al., J. Phys. Chem 100: 17050 (1996); all of which are incorporated by reference.

In a preferred embodiment, an input electron source in solution is used in the initiation of electron transfer, preferably when initiation and detection are being done using DC current or at AC frequencies where diffusion is not limiting. In general, as will be appreciated by those in the art, preferred embodiments utilize monolayers that contain a minimum of "holes", such that short-circuiting of the system is avoided. This may be done in several general ways. In a preferred embodiment, an input electron source is used that has a lower or similar redox potential than the ETM of the label probe. Thus, at voltages above the redox potential of the input electron source, both the ETM and the input electron source are oxidized and can thus donate electrons; the ETM donates an electron to the electrode and the input source donates to the ETM. For example, ferrocene, as a ETM attached to the compositions of the invention as described in the examples, has a redox potential of roughly 200 mV in aqueous solution (which can change significantly depending on what the ferrocene is bound to, the manner of the linkage and the presence of any substitution groups). Ferrocyanide, an electron source, has a redox potential of roughly 200 mV as well (in aqueous solution). Accordingly, at or above voltages of roughly 200 mV, ferrocene is converted to ferricenium, which then transfers an electron to the electrode. Now the ferricyanide can be oxidized to transfer an electron to the ETM. In this way, the electron source (or co-reductant) serves to amplify the signal generated in the system, as the electron source molecules rapidly and repeatedly donate electrons to the ETM attached to the nucleic acid. The rate of electron donation or acceptance will be limited by the rate of diffusion of the co-reductant, the electron transfer between the co-reductant and the ETM, which in turn is affected by the concentration and size, etc.

Alternatively, input electron sources that have lower redox potentials than the ETM are used. At voltages less than the redox potential of the ETM, but higher than the redox potential of the electron source, the input source such as ferrocyanide is unable to be oxidized and thus is unable to donate an electron to the ETM; i.e. no electron transfer occurs. Once ferrocene is oxidized, then there is a pathway for electron transfer.

In an alternate preferred embodiment, an input electron source is used that has a higher redox potential than the ETM of the label probe. For example, luminol, an electron source, has a redox potential of roughly 720 mV. At voltages higher than the redox potential of the ETM, but lower than the redox potential of the electron source, i.e. 200–720 mV, the ferrocene is oxided, and transfers a single electron to the electrode via the conductive oligomer. However, the ETM is unable to accept any electrons from the luminol electron source, since the voltages are less than the redox potential of the luminol. However, at or above the redox potential of luminol, the luminol then transfers an electron to the ETM, allowing rapid and repeated electron transfer. In this way, the electron source (or co-reductant) serves to amplify the signal generated in the system, as the electron source molecules rapidly and repeatedly donate electrons to the ETM of the label probe.

Luminol has the added benefit of becoming a chemiluminescent species upon oxidation (see Jirka et al., Analytica Chimica Acta 284:345 (1993)), thus allowing photo-detection of electron transfer from the ETM to the electrode. Thus, as long as the luminol is unable to contact the electrode directly, i.e. in the presence of the SAM such that there is no efficient electron transfer pathway to the electrode, luminol can only be oxidized by transferring an electron to the ETM on the label probe. When the ETM is not present, i.e. when the target sequence is not hybridized to the composition of the invention, luminol is not significantly oxidized, resulting in a low photon emission and thus a low (if any) signal from the luminol. In the presence of the target, a much larger signal is generated. Thus, the measure of luminol oxidation by photon emission is an indirect measurement of the ability of the ETM to donate electrons to the electrode. Furthermore, since photon detection is generally more sensitive than electronic detection, the sensitivity of the system may be increased. Initial results suggest that luminescence may depend on hydrogen peroxide concentration, pH, and luminol concentration, the latter of which appears to be non-linear.

Suitable electron source molecules are well known in the art, and include, but are not limited to, ferricyanide, and luminol.

Alternatively, output electron acceptors or sinks could be used, i.e. the above reactions could be run in reverse, with the ETM such as a metallocene receiving an electron from the electrode, converting it to the metallicenium, with the output electron acceptor then accepting the electron rapidly and repeatedly. In this embodiment, cobalticenium is the preferred ETM.

The presence of the ETMs at the surface of the monolayer can be detected in a variety of ways. A variety of detection methods may be used, including, but not limited to, optical detection (as a result of spectral changes upon changes in redox states), which includes fluorescence, phosphorescence, luminiscence, chemiluminescence, electrochemiluminescence, and refractive index; and electronic detection, including, but not limited to, amperommetry, voltammetry, capacitance an d impedance. These methods include time or frequency dependent methods based on AC or DC currents, pulsed methods, lock-in techniques, filtering (high pass, low pass, band pass), and time-resolved techniques including time-resolved fluorescence.

In one embodiment, the efficient transfer of electrons from the ETM to the electrode results in stereotyped changes in the redox state of the ETM. With many ETMs including the complexes of ruthenium containing bipyridine, pyridine and imidazole rings, these changes in redox state are associated with changes in spectral properties. Significant differences in absorbance are observed between reduced and oxidized states for these molecules. See for example Fabbrizzi et al., Chem. Soc. Rev. 1995 pp197–202). These differences can be monitored using a spectrophotometer or simple photomultiplier tube device.

In this embodiment, possible electron donors and acceptors include all the derivatives listed above for photoactivation or initiation. Preferred electron donors and acceptors have characteristically large spectral changes upon oxidation and reduction resulting in highly sensitive monitoring of electron transfer. Such examples include $Ru(NH_3)_4py$ and $Ru(bpy)_2im$ as preferred examples. It should be understood that only the donor or acceptor that is being monitored by absorbance need have ideal spectral characteristics.

In a preferred embodiment, the electron transfer is detected fluorometrically. Numerous transition metal complexes, including those of ruthenium, have distinct fluorescence properties. Therefore, the change in redox state of the electron donors and electron acceptors attached to the nucleic acid can be monitored very sensitively using fluorescence, for example with $Ru(4,7\text{-biphenyl}_2\text{-phenanthroline})_3^{2+}$. The production of this compound can be easily measured using standard fluorescence assay techniques. For example, laser induced fluorescence can be recorded in a standard single cell fluorimeter, a flow through "on-line" fluorimeter (such as those attached to a chromatography system) or a multi-sample "plate-reader" similar to those marketed for 96-well immuno assays.

Alternatively, fluorescence can be measured using fiber optic sensors with nucleic acid probes in solution or attached to the fiber optic. Fluorescence is monitored using a photomultiplier tube or other light detection instrument attached to the fiber optic. The advantage of this system is the extremely small volumes of sample that can be assayed.

In addition, scanning fluorescence detectors such as the FluorImager sold by Molecular Dynamics are ideally suited to monitoring the fluorescence of modified nucleic acid molecules arrayed on solid surfaces. The advantage of this system is the large number of electron transfer probes that can be scanned at once using chips covered with thousands of distinct nucleic acid probes.

Many transition metal complexes display fluorescence with large Stokes shifts. Suitable examples include bis- and trisphenanthroline complexes and bis- and trisbipyridyl complexes of transition metals such as ruthenium (see Juris, A., Balzani, V., et. al. Coord. Chem. Rev., V. 84, p. 85–277, 1988). Preferred examples display efficient fluorescence (reasonably high quantum yields) as well as low reorganization energies. These include $Ru(4,7\text{-biphenyl}_2\text{-phenanthroline})_3^{2+}$, $Ru(4,4'\text{-diphenyl-2,2-bipyridine})_3^{2+}$ and platinum complexes (see Cummings et al., J. Am. Chem. Soc. 118:1949–1960 (1996), incorporated by reference). Alternatively, a reduction in fluorescence associated with hybridization can be measured using these systems.

In a further embodiment, electrochemiluminescence is used as the basis of the electron transfer detection. With some ETMs such as $Ru^{2+}$ $(bpy)_3$, direct luminescence accompanies excited state decay. Changes in this property are associated with nucleic acid hybridization and can be monitored with a simple photomultiplier tube arrangement (see Blackburn, G. F. Clin. Chem. 37: 1534–1539 (1991); and Juris et al., supra.

In a preferred embodiment, electronic detection is used, including amperommetry, voltammetry, capacitance, and impedance. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (anodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry; and photoelectrochemistry.

In a preferred embodiment, monitoring electron transfer is via amperometric detection. This method of detection involves applying a potential (as compared to a separate reference electrode) between the nucleic acid-conjugated electrode and a reference (counter) electrode in the sample containing target genes of interest. Electron transfer of differing efficiencies is induced in samples in the presence or absence of target nucleic acid; that is, the presence or absence of the target nucleic acid, and thus the label probe, can result in different currents.

The device for measuring electron transfer amperometrically involves sensitive current detection and includes a means of controlling the voltage potential, usually a potentiostat. This voltage is optimized with reference to the potential of the electron donating complex on the label probe. Possible electron donating complexes include those previously mentioned with complexes of iron, osmium, platinum, cobalt, rhenium and ruthenium being preferred and complexes of iron being most preferred.

In a preferred embodiment, alternative electron detection modes are utilized. For example, potentiometric (or voltammetric) measurements involve non-faradaic (no net current flow) processes and are utilized traditionally in pH and other ion detectors. Similar sensors are used to monitor electron transfer between the ETM and the electrode. In addition, other properties of insulators (such as resistance) and of conductors (such as conductivity, impedance and capicitance) could be used to monitor electron transfer between ETM and the electrode. Finally, any system that generates a current (such as electron transfer) also generates a small magnetic field, which may be monitored in some embodiments.

It should be understood that one benefit of the fast rates of electron transfer observed in the compositions of the invention is that time resolution can greatly enhance the signal-to-noise results of monitors based on absorbance, fluorescence and electronic current. The fast rates of electron transfer of the present invention result both in high signals and stereotyped delays between electron transfer initiation and completion. By amplifying signals of particular delays, such as through the use of pulsed initiation of electron transfer and "lock-in" amplifiers of detection, and Fourier transforms.

In a preferred embodiment, electron transfer is initiated using alternating current (AC) methods. Without being bound by theory, it appears that ETMs, bound to an electrode, generally respond similarly to an AC voltage across a circuit containing resistors and capacitors. Basically, any methods which enable the determination of the nature of these complexes, which act as a resistor and capacitor, can be used as the basis of detection. Surprisingly, traditional electrochemical theory, such as exemplified in Laviron et al., J. Electroanal. Chem. 97:135 (1979) and Laviron et al., J. Electroanal. Chem. 105:35 (1979), both of which are incorporated by reference, do not accurately model the systems described herein, except for very small $E_{AC}$ (less than 10 mV) and relatively large numbers of molecules. That is, the AC current (I) is not accurately described by Laviron's equation. This may be due in part to the fact that this theory assumes an unlimited source and sink of electrons, which is not true in the present systems.

The AC voltametry theory that models these systems well is outlined in O'Connor et al., J. Electroanal. Chem. 466 (2):197–202 (1999), hereby expressly incorporated by reference. The equation that predicts these systems is shown below as Equation 1:

$$i_{avg} = 2nfFN_{total} \cdot \frac{\sinh\left[\frac{nF}{RT} \cdot E_{AC}\right]}{\cosh\left[\frac{nF}{RT} \cdot E_{AC}\right] + \cosh\left[\frac{nF}{RT}(E_{DC} - E_O)\right]} \quad \text{Equation 1}$$

In Equation 1, n is the number of electrons oxidized or reduced per redox molecule, f is the applied frequency, F is Faraday's constant, $N_{total}$ is the total number of redox molecules, $E_O$ is the formal potential of the redox molecule, R is the gas constant, T is the temperature in degrees Kelvin, and $E_{DC}$ is the electrode potential. The model fits the experimental data very well. In some cases the current is smaller than predicted, however this has been shown to be caused by ferrocene degradation which may be remedied in a number of ways.

In addition, the faradaic current can also be expressed as a function of time, as shown in Equation 2:

$$I_f(t) = \frac{q_e N_{total} nF}{2RT\left(\cosh\left[\frac{nF}{RT}(V(t) - E_O)\right] + 1\right)} \cdot \frac{dV(t)}{dt} \quad \text{Equation 2}$$

$I_F$ is the Faradaic current and $q_e$ is the elementary charge.

However, Equation 1 does not incorporate the effect of electron transfer rate nor of instrument factors. Electron transfer rate is important when the rate is close to or lower than the applied frequency. Thus, the true $i_{AC}$ should be a function of all three, as depicted in Equation 3.

Equation 3

$i_{AC} = f(\text{Nernst factors}) f(k_{ET}) f(\text{instrument factors})$

These equations can be used to model and predict the expected AC currents in systems which use input signals comprising both AC and DC components. As outlined above, traditional theory surprisingly does not model these systems at all, except for very low voltages.

In general, non-specifically bound label probes/ETMs show differences in impedance (i.e. higher impedances) than when the label probes containing the ETMs are specifically bound in the correct orientation. In a preferred embodiment, the non-specifically bound material is washed away, resulting in an effective impedance of infinity. Thus, AC detection gives several advantages as is generally discussed below, including an increase in sensitivity, and the ability to "filter out" background noise. In particular, changes in impedance (including, for example, bulk impedance) as between non-specific binding of ETM-containing probes and target-specific assay complex formation may be monitored.

Accordingly, when using AC initiation and detection methods, the frequency response of the system changes as a result of the presence of the ETM. By "frequency response" herein is meant a modification of signals as a result of electron transfer between the electrode and the ETM. This modification is different depending on signal frequency. A frequency response includes AC currents at one or more frequencies, phase shifts, DC offset voltages, faradaic impedance, etc.

Once the assay complex including the target sequence and label probe is made, a first input electrical signal is then applied to the system, preferably via at least the sample electrode (containing the complexes of the invention) and the counter electrode, to initiate electron transfer between the electrode and the ETM. Three electrode systems may also be used, with the voltage applied to the reference and working electrodes. The first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 500 mV being especially preferred. The AC frequency ranges from about 0.01 Hz to about 100 MHz, with from about 10 Hz to about 10 MHz being preferred, and from about 100 Hz to about 20 MHz being especially preferred.

The use of combinations of AC and DC signals gives a variety of advantages, including surprising sensitivity and signal maximization.

In a preferred embodiment, the first input signal comprises a DC component and an AC component. That is, a DC offset voltage between the sample and counter electrodes is swept through the electrochemical potential of the ETM (for example, when ferrocene is used, the sweep is generally from 0 to 500 mV) (or alternatively, the working electrode is grounded and the reference electrode is swept from 0 to –500 mV). The sweep is used to identify the DC voltage at which the maximum response of the system is seen. This is generally at or about the electrochemical potential of the ETM. Once this voltage is determined, either a sweep or one or more uniform DC offset voltages may be used. DC offset voltages of from about –1 V to about +1.1 V are preferred, with from about –500 mV to about +800 mV being especially preferred, and from about –300 mV to about 500 mV being particularly preferred. In a preferred embodiment, the DC offset voltage is not zero. On top of the DC offset voltage, an AC signal component of variable amplitude and frequency is applied. If the ETM is present, and can respond to the AC perturbation, an AC current will be produced due to electron transfer between the electrode and the ETM.

For defined systems, it may be sufficient to apply a single input signal to differentiate between the presence and absence of the ETM (i.e. the presence of the target sequence) nucleic acid. Alternatively, a plurality of input signals are applied. As outlined herein, this may take a variety of forms, including using multiple frequencies, multiple DC offset voltages, or multiple AC amplitudes, or combinations of any or all of these.

Thus, in a preferred embodiment, multiple DC offset voltages are used, although as outlined above, DC voltage sweeps are preferred. This may be done at a single frequency, or at two or more frequencies.

In a preferred embodiment, the AC amplitude is varied. Without being bound by theory, it appears that increasing the amplitude increases the driving force. Thus, higher amplitudes, which result in higher overpotentials give faster rates of electron transfer. Thus, generally, the same system gives an improved response (i.e. higher output signals) at any single frequency through the use of higher overpotentials at that frequency. Thus, the amplitude may be increased at high frequencies to increase the rate of electron transfer through the system, resulting in greater sensitivity. In addition, this may be used, for example, to induce responses in slower systems such as those that do not possess optimal spacing configurations.

In a preferred embodiment, measurements of the system are taken at at least two separate amplitudes or overpotentials, with measurements at a plurality of amplitudes being preferred. As noted above, changes in response as a result of changes in amplitude may form the basis of identification, calibration and quantification of the system. In addition, one or more AC frequencies can be used as well.

In a preferred embodiment, the AC frequency is varied. At different frequencies, different molecules respond in different ways. As will be appreciated by those in the art, increasing the frequency generally increases the output current. However, when the frequency is greater than the rate at which electrons may travel between the electrode and the ETM, higher frequencies result in a loss or decrease of output signal. At some point, the frequency will be greater than the rate of electron transfer between the ETM and the electrode, and then the output signal will also drop.

In one embodiment, detection utilizes a single measurement of output signal at a single frequency. That is, the frequency response of the system in the absence of target sequence, and thus the absence of label probe containing ETMs, can be previously determined to be very low at a particular high frequency. Using this information, any response at a particular frequency, will show the presence of the assay complex. That is, any response at a particular frequency is characteristic of the assay complex. Thus, it may only be necessary to use a single input high frequency, and any changes in frequency response is an indication that the ETM is present, and thus that the target sequence is present.

In addition, the use of AC techniques allows the significant reduction of background signals at any single frequency due to entities other than the ETMs, i.e. "locking out" or "filtering" unwanted signals. That is, the frequency response of a charge carrier or redox active molecule in solution will be limited by its diffusion coefficient and charge transfer coefficient. Accordingly, at high frequencies, a charge carrier may not diffuse rapidly enough to transfer its charge to the electrode, and/or the charge transfer kinetics may not be fast enough. This is particularly significant in embodiments that do not have good monolayers, i.e. have partial or insufficient monolayers, i.e. where the solvent is accessible to the electrode. As outlined above, in DC techniques, the presence of "holes" where the electrode is accessible to the solvent can result in solvent charge carriers "short circuiting" the system, i.e. the reach the electrode and generate background signal. However, using the present AC techniques, one or more frequencies can be chosen that prevent a frequency response of one or more charge carriers in solution, whether or not a monolayer is present. This is particularly significant since many biological fluids such as blood contain significant amounts of redox active molecules which can interfere with amperometric detection methods.

In a preferred embodiment, measurements of the system are taken at at least two separate frequencies, with measurements at a plurality of frequencies being preferred. A plurality of frequencies includes a scan. For example, measuring the output signal, e.g., the AC current, at a low input frequency such as 1–20 Hz, and comparing the response to the output signal at high frequency such as 10–100 kHz will show a frequency response difference between the presence and absence of the ETM. In a preferred embodiment, the frequency response is determined at at least two, preferably at least about five, and more preferably at least about ten frequencies.

After transmitting the input signal to initiate electron transfer, an output signal is received or detected. The presence and magnitude of the output signal will depend on a number of factors, including the overpotential/amplitude of the input signal; the frequency of the input AC signal; the composition of the intervening medium; the DC offset; the environment of the system; the nature of the ETM; the solvent; and the type and concentration of salt. At a given input signal, the presence and magnitude of the output signal will depend in general on the presence or absence of the ETM, the placement and distance of the ETM from the surface of the monolayer and the character of the input signal. In some embodiments, it may be possible to distinguish between non-specific binding of label probes and the formation of target specific assay complexes containing label probes, on the basis of impedance.

In a preferred embodiment, the output signal comprises an AC current. As outlined above, the magnitude of the output current will depend on a number of parameters. By varying these parameters, the system may be optimized in a number of ways.

In general, AC currents generated in the present invention range from about 1 femtoamp to about 1 milliamp, with currents from about 50 femtoamps to about 100 microamps being preferred, and from about 1 picoamp to about 1 microamp being especially preferred.

In a preferred embodiment, the output signal is phase shifted in the AC component relative to the input signal. Without being bound by theory, it appears that the systems of the present invention may be sufficiently uniform to allow phase-shifting based detection. That is, the complex biomolecules of the invention through which electron transfer occurs react to the AC input in a homogeneous manner, similar to standard electronic components, such that a phase shift can be determined. This may serve as the basis of detection between the presence and absence of the ETM, and/or differences between the presence of target-specific assay complexes comprising label probes and non-specific binding of the label probes to the system components.

The output signal is characteristic of the presence of the ETM; that is, the output signal is characteristic of the presence of the target-specific assay complex comprising label probes and ETMs. In a preferred embodiment, the basis of the detection is a difference in the faradaic impedance of the system as a result of the formation of the assay complex. Faradaic impedance is the impedance of the system between the electrode and the ETM. Faradaic impedance is quite different from the bulk or dielectric impedance, which is the impedance of the bulk solution between the electrodes. Many factors may change the faradaic impedance which may not effect the bulk impedance, and vice versa. Thus, the assay complexes comprising the nucleic acids in this system have a certain faradaic impedance, that will depend on the distance between the ETM and the electrode, their electronic properties, and the composition of the intervening medium, among other things. Of importance in the methods of the invention is that the faradaic impedance between the ETM and the electrode is signficantly different depending on whether the label probes containing the ETMs are specifically or non-specifically bound to the electrode.

Accordingly, the present invention further provides electronic devices or apparatus for the detection of analytes using the compositions of the invention. The apparatus includes a test chamber for receiving a sample solution which has at least a first measuring or sample electrode, and a second measuring or counter electrode. Three electrode systems are also useful. The first and second measuring electrodes are in contact with a test sample receiving region, such that in the presence of a liquid test sample, the two electrophoresis electrodes may be in electrical contact.

In a preferred embodiment, the apparatus also includes detection electrodes comprising a single stranded nucleic acid capture probe covalently attached via an attachment linker, and a monolayer comprising conductive oligomers, such as are described herein.

The apparatus further comprises an AC voltage source electrically connected to the test chamber; that is, to the measuring electrodes. Preferably, the AC voltage source is capable of delivering DC offset voltage as well.

In a preferred embodiment, the apparatus further comprises a processor capable of comparing the input signal and the output signal. The processor is coupled to the electrodes and configured to receive an output signal, and thus detect the presence of the target nucleic acid.

Thus, the compositions of the present invention may be used in a variety of research, clinical, quality control, or field testing settings.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, clymidia and other sexually transmitted diseases, may also be detected.

In a preferred embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, *Salmonella, Campylobacter, Vibrio cholerae, Leishmania*, enterotoxic strains of *E. coli*, and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization.

Thus, the present invention provides for extremely specific and sensitive probes, which may, in some embodiments, detect target sequences without removal of unhybridized probe. This will be useful in the generation of automated gene probe assays.

Alternatively, the compositions of the invention are useful to detect successful gene amplification in PCR, thus allowing successful PCR reactions to be an indication of the presence or absence of a target sequence. PCR may be used in this manner in several ways. For example, in one embodiment, the PCR reaction is done as is known in the art, and then added to a composition of the invention comprising the target nucleic acid with a ETM, covalently attached to an electrode via a conductive oligomer with subsequent detection of the target sequence. Alternatively, PCR is done using nucleotides labelled with a ETM, either in the presence of, or with subsequent addition to, an electrode with a conductive oligomer and a target nucleic acid. Binding of the PCR product containing ETMs to the electrode composition will allow detection via electron transfer. Finally, the nucleic acid attached to the electrode via a conductive polymer may be one PCR primer, with addition of a second primer labelled with an ETM. Elongation results in double stranded nucleic acid with a ETM and electrode covalently attached. In this way, the present invention is used for PCR detection of target sequences.

In a preferred embodiment, the arrays are used for mRNA detection. A preferred embodiment utilizes either capture probes or capture extender probes that hybridize close to the 3' polyadenylation tail of the mRNAs. This allows the use of one species of target binding probe for detection, i.e. the probe contains a poly-T portion that will bind to the poly-A tail of the mRNA target. Generally, the probe will contain a second portion, preferably non-poly-T, that will bind to the detection probe (or other probe). This allows one target-binding probe to be made, and thus decreases the amount of different probe synthesis that is done.

In a preferred embodiment, the use of restriction enzymes and ligation methods allows the creation of "universal" arrays. In this embodiment, monolayers comprising capture probes that comprise restriction endonuclease ends, as is generally depicted in FIG. 6. By utilizing complementary portions of nucleic acid, while leaving "sticky ends", an array comprising any number of restriction endonuclease sites is made. Treating a target sample with one or more of these restriction endonucleases allows the targets to bind to the array. This can be done without knowing the sequence of the target. The target sequences can be ligated, as desired, using standard methods such as ligases, and the target sequence detected, using either standard labels or the methods of the invention.

The present invention provides methods which can result in sensitive detection of nucleic acids. In a preferred embodiment, less than about $10 \times 10^6$ molecules are detected, with less than about $10 \times 10^5$ being preferred, less than $10 \times 10^4$ being particularly preferred, less than about $10 \times 10^3$ being especially preferred, and less than about $10 \times 10^2$ being most preferred. As will be appreciated by those in the art, this assumes a 1:1 correlation between target sequences and reporter molecules; if more than one reporter molecule (i.e. electron transfer moeity) is used for each target sequence, the sensitivity will go up.

While the limits of detection are currently being evaluated, based on the published electron transfer rate through DNA, which is roughly $1 \times 10^6$ electrons/sec/duplex for an 8 base pair separation (see Meade et al., Angw. Chem. Eng. Ed., 34:352 (1995)) and high driving forces, AC frequencies of about 100 kHz should be possible. As the preliminary results show, electron transfer through these systems is quite efficient, resulting in nearly $100 \times 10^3$ electrons/sec, resulting in potential femtoamp sensitivity for very few molecules.

All references cited herein are incorporated by reference in their entireity.

EXAMPLES

Example 1

General Methods of Making Substrates and Monolayers

SAM formation on Substrates—General Procedure

The self-assembled monolayers were formed on a clean gold surface. The gold surface can be prepared by a variety of different methods: melted or polished gold wire, sputtered or evaporated gold on glass or mica or silicon wafers or some other substrate, electroplated or electroless gold on circuit board material or glass or silicon or some other substrate. Both the vacuum deposited gold samples (evaporated and sputtered) and the solution deposited gold samples (electroless and electroplated) often require the use of an adhesion layer between the substrate and the gold in order to insure good mechanical stability. Chromium, Titanium, Titanium/Tungsten or Tantalum is frequently employed with sputtered and evaporated gold. Electroplated nickel is usually employed with electroplated and electroless gold, however other adhesion materials can be used.

The gold substrate is cleaned prior to monolayer formation. A variety of different procedures have been employed. Cleaning with a chemical solution is the most prevalent. Piranha solution (hydrogen peroxide/sulfuric acid) or aqua regia cleaning (Hydrochloric acid/Nitric acid) is most prevalent, however electrochemical methods, flame treatment and plasma methods have also been employed.

Following cleaning, the gold substrate is incubated in a deposition solution. The deposition solution consists of a mixture of various thiols in a solvent. A mixture of alkane thiols in an organic solvent like ethanol is the most prevalent procedure, however numerous variations have been developed. Alternative procedures involve gas phase deposition of the alkane thiol, microcontact printing, deposition using neat thiol, deposition from aqueous solvent and two step procedures have been developed. The concentration of the alkane thiol in the deposition solution ranges from molar to submicromolar range with 0.5–2.0 millimolar being the most prevalent. The gold substrate is incubated/placed in contact with the deposition solution for less than a second to days depending on the procedure. The most common time is 1 hr to overnight incubation. The incubation is usually performed at room temperature, however temperatures up to 50° C. are common.

Mixed monolayers that contain DNA are usually prepared using a two step procedure. The thiolated DNA is deposited during the first deposition step and the mixed monolayer formation is completed during the second step in which a second thiol solution minus DNA is added. The second step frequently involves mild heating to promote monolayer reorganization.

General Procedure for SAM Formation—Deposited from Organic Solution

A clean gold surface was placed into a clean vial. A DNA deposition solution in organic solvent was prepared in which the total thiol concentration was between 400 uM and 1.0 mM. The deposition solution contained thiol modified DNA and thiol diluent molecules. The ratio of DNA to diluent was usually between 10:1 and 1:10 with 1:1 being preferred. The preferred solvents are tetrahydrofuran (THF), acetonitrile, dimethylforamide (DMF) or mixtures thereof. Sufficient DNA deposition solution is added to the vial so as to completely cover the electrode surface. The gold substrate is allowed to incubate at ambient temperature or slightly above ambient temperature for 5–30 minutes. After the initial incubation, the deposition solution is removed and a solution of diluent molecule only (100 uM–1.0 mM) in organic solvent is added. The gold substrate is allowed to incubate at room temperature or above room temperature until a complete monolayer is formed (10 minutes–24 hours). The gold sample is removed from the solution, rinsed in clean solvent and used.

General Procedure for SAM Formation—Deposited from Aqueous Solution

A clean gold surface is placed into a clean vial. A DNA deposition solution in water is prepared in which the total thiol concentration is between 1 uM and 200 uM. The aqueous solution frequently has salt present (approximately 1 M), however pure water can be used. The deposition solution contains thiol modified DNA and often a thiol diluent molecule. The ratio of DNA to diluent is usually between 10:1 and 1:10 with 1:1 being preferred. The DNA deposition solution is added to the vial in such a volume so as to completely cover the electrode surface. The gold substrate is allowed to incubate at ambient temperature or slightly above ambient temperature for 1–30 minutes with 5 minutes usually being sufficient. After the initial incubation, the deposition solution is removed and a solution of diluent molecule only (10 uM–1.0 mM) in either water or organic solvent is added. The gold substrate is allowed to incubate at room temperature or above room temperature until a complete monolayer is formed (10 minutes–24 hours). The gold sample is removed from the solution, rinsed in clean solvent and used.

Monolayers on Au Ball Electrodes

Creating Au Ball Electrodes: Use a razor blade to cut 10 cm lengths of gold wire (127 μm diameter, 99.99% pure; e.g. from Aldrich). Use a 16 gauge needle to pass the wire through a #4 natural rubber septum (of the size to fit over a ½ mL PCR eppendorf tube). (This serves to support the wire and seal the tubes during deposition. See below.) Use a clean-burning flame (methane or propane) to melt one centimeter of the wire and form a sphere attached to the wire terminus. Adjust the wire length such that when sealed in a PCR tube the gold ball would be positioned near the bottom, able to be submerged in 20 μL of liquid. On the day of use, dip the electrodes in aqua regia (4:3:1 $H_2O:HCl:HNO_3$) for 20 seconds and then rinse thoroughly with water.

Derivatization: For 5 minutes, heat 20 μL aliquots of deposition solutions (2:2:1 DNA/H6/M44 at 833 μM total in DMF) in PCR tubes on a PCR block at 50° C. Then put each electrode into a tube of deposition solution (submerging just the gold ball—as little of the wire "stem" as possible) and remove to room temperature. Incubate for fifteen minutes before transferring the electrodes into PCR tubes with 200 μL of 400 μM M44 in DMF (submerging much of the wire stem as well). Let sit in M44 at room temperature for 5 minutes, then put on the PCR block and run HCLONG. Take electrodes out of the M44 solution, dip in 6×SSC, and place in PCR tubes with 20 μL of hybridization solution. Dip electrodes in 6×SSC prior to ACV measurement.

HCLONG: 65° C. 2', −0.3° C./s to 40° C., 40° C. 2', +0.3° C./s to 55° C., 55° C. 2', −0.3° C./s to 30° C., 30° C. 2', +0.3° C./s to 35° C., 35° C. 2', −0.3° C./s to 22° C.

Manufacture of Circuit Boards

An 18"×24"×0.047" panel of FR-4 (General Electric) with a half-ounce copper foil on both sides was drilled according to specifications (Gerber files). The FR-4 panel is plated with electroless copper (500 microinches) to make the specified drill-holes conductive and then panel is plated with an additional 500 microinches of electroplated copper. Following copper plating, the panel is etched according to specifications via cupric chloride etching (acid etching). The etched panel is then plated with 400 microinches of electroplated nickel with brightner followed by 50 microinches of soft gold (99.99% purity). The gold panel is coated with liquid photoimagable solder mask (Probimer 52, Ciba-Geigy Co.) on both sides of the panel. The imaging is done according to specifications. 14 sensor electrodes that are 250 micron in diameter and 2 larger electrodes (500 microns in diameter) are created with insulated leads leading to gold plated contacts at the edge of the board. The solder masked panel is then scored according to specifications to create individual wafers that are 1"×1". A silver/silver chloride paste is applied to one of the two larger electrodes (ERCON R-414). The panel is then plasma cleaned with an Argon/Oxygen Plasma mixture. Following cleaning, the panel is stored in a foil-lined bag until use.

Monolayer Deposition on Circuit Boards

The circuit boards are removed from the foil-lined bags and immersed in a 10% sulfuric acid solution for 30 seconds. Following the sulfuric acid treatment, the boards are immersed in two Milli-Q water baths for 1 minute each. The boards are then dried under a stream of nitrogen. The boards are placed on a X-Y table in a humidity chamber and a 30 nanoliter drop of DNA deposition solution is placed on each of the 14 electrodes. The DNA deposition solution consists of 33 uM thiolated DNA, 33 uM 2-unit phenylacetylene wire (H6), and 16 uM M44 in 6×SSC (900 mM sodium chloride, 90 mM sodium Citrate, pH 7) w/ 1% Triethylamine. The drop is incubated at room temperature for 5 minutes and then 33 uM 2-unit phenylacetylene wire (H6), and 16 uM undec-1-en-11yltri(ethylene glycol)(HS—$CH_2$)$_{11}$—(O$CH_2$$CH_2$)$_3$—OH) in 6×SSC (900 mM sodium chloride, 90 mM sodium Citrate, pH 7) w/1% Triethylamine. 3 electrodes were spotted with a solution containing DNA 1 (5'-ACCATGGACACAGAT($CH_2$)$_{16}$SH-3'). 4 electrodes were spotted with a solution containing DNA 2 (5'TCATTGATGGTCTCTTTTAACA(($CH_2$)$_{16}$SH-3'). 4 electrodes were spotted with DNA 3 (5'CACAGTGGGGGGACATCAAGCAGCCATGCAAA($CH_2$)$_{16}$SH-3'). 3 electrodes were spotted with DNA 4 (5'-TGTGCAGTTGACGTGGAT($CH_2$)$_{16}$SH-3'). The deposition solution was allowed to incubate at room temperature for 5 minutes and then the drop was removed by rinsing in a Milli-Q water bath. The boards were immersed in a 45° C. bath of M44 in acetonitrile. After 30 minutes, the boards were removed and immersed in an acetonitrile bath for 30 seconds followed by a milli-Q water bath for 30 seconds. The boards were dried under a stream of nitrogen and stored in foiled-lined bags flushed with nitrogen until use.

Hybridization and Measurement

The modified boards were removed from the foil-lined bags and fitted with an injection molded sample chamber (cartridge). The chamber was adhered to the board using double-sided sticky tape and had a total volume of 250 microliters. A hybridization solution was prepared. The solution contains 10 nM DNA target (5'-TGTGCAGTTGACGTGGATTGTTAAAAGAGACCATCAATGAGGAAGCTGCA GMTGGGATAGAGTCATCCAGT-3' (D-998), 30 nM signaling probe (D-1055) and 10 nm 5'-TCTACAG(N6)C(N6)ATCTGTGTCCATGGT-3' (N6 is shown in FIG. 1D of PCTUS99/01705; it comprises a ferrocene connected by a 4 carbon chain to the 2' oxygen of the ribose of a nucleoside).

The signalling probe is as follows:

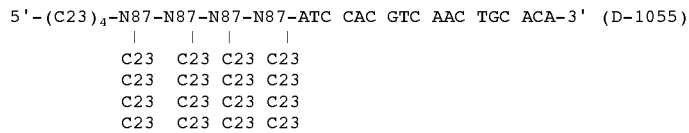

the drop is removed by rinsing in a Milli-Q water bath. The boards are immersed in a 45° C. bath of M44 in acetontrile. After 30 minutes, the boards are removed and immersed in an acetonitrile bath for 30 seconds followed by a milli-Q water bath for 30 seconds. The boards are dried under a stream of nitrogen.

Example 2

Detection of Target Sequences

Monolayer Deposition on Circuit Boards

As above, the circuit boards were removed from the foil-lined bags and immersed in a 10% sulfuric acid solution for 30 seconds. Following the sulfuric acid treatment, the boards were immersed in two Milli-Q water baths for 1 minute each. The boards were then dried under a stream of nitrogen. The boards were placed on a X-Y table in a humidity chamber and a 30 nanoliter drop of DNA deposition solution was placed on each of the 14 electrodes. The DNA deposition solution consisted of 33 uM thiolated DNA, N87 is a branch point comprising a ring structure. C23 is shown in FIG. 1F of PCTUS99/01705. In a solution containing 25% Qiagen lysis buffer AL, 455 mM NaClO$_4$, 195 mM NaCl, 1.0 mM mercaptohexanol and 10% fetal calf serum. 250 microliters of hybrid solution was injected into the cartridge and allowed to hybridize for 12 hours. After 12 hours, the hybridized chip was plugged into a homemade transconductance amplifier with switching circuitry. The transconductance amplifier was equipped with summing circuitry that combines a DC ramp from the computer DAQ card and an AC sine wave from the lock-in amplifier (SR830 Stanford Instruments). Each electrode was scanned sequentially and the data was saved and manipulated using a homemade program designed using Labview (National Instruments). The chip was scanned at between −100 mV and 500 mV (pseudo Ag/Ag/Cl reference electrode) DC with a 25 mV (50 mV peak to peak), 1000 Hz superimposed sine wave. The output current was fed into the lock-in amplifier and the 1000 Hz signal was recorded (ACV technique). The data for each set of pads was compiled and averaged.

|  | Ip | Relative Intensity Ip |
| --- | --- | --- |
| DNA 1 (Positive 2 Fc) | 34 nA | 0.11 |
| DNA 2 (Positive Sandwich Assay) | 218 nA | 0.7 |
| DNA 3 (Negative) | 0.3 nA | 0.001 |
| DNA 4 (Positive Sandwich Assay) | 317 nA | 1 |

The results are shown in FIG. 14.

The invention claimed is:

1. A device comprising a substrate comprising:
 a) a first surface comprising:
  i) an array of detection electrodes each comprising a covalently attached capture ligand;
  ii) at least a first electrophoresis electrode;
 b) a second surface comprising at least a second electrophoresis electrode; and
 c) at least one channel connecting said first surface and second surface.

2. A device according to claim 1 wherein said channel comprises a permeation layer material.

3. A device according to claim 2 wherein said channel comprises a membrane.

4. A device according to claim 1 further comprising a detection chamber, wherein said detection chamber comprises said surfaces.

5. A device according to claim 1 wherein said detection electrodes further comprise a self-assembled monolayer.

6. A device according to claim 1 wherein said substrate is Printed Circuit (PC) board.

7. A device according to claim 1 wherein said capture ligand is nucleic acid.

8. A device comprising a detection chamber comprising:
 a) a first subchamber comprising an array of detection electrodes each comprising a covalently attached capture ligand;
 b) a second subchamber comprising an absorbent material; and
 c) a substrate comprising:
  i) a first surface in contact with said array of detection electrodes;
  ii) a second surface in contact with said absorbent material;
  iii) at least one channel connecting said first surface and said second surface; and
  iv) a size exclusion partition at either end of said at least one channel.

9. A device according to claim 8 wherein said channel comprises a permeation layer material.

10. A device according to claim 8 wherein said channel comprises a membrane.

11. A device according to claim 8 wherein said detection electrodes further comprise a self-assembled monolayer.

12. A device according to claim 8 wherein said substrate is PC board.

13. A device according to claim 8 wherein said capture ligand is nucleic acid.

14. The device according to claim 8, wherein said size exclusion partition is in contact with said first surface.

15. The device according to claim 8, wherein said size exclusion partition is in contact with said second surface.

16. The device according to claim 8, wherein said size exclusion partition is a semi-permeable membrane.

17. A method of detecting a target analyte in a sample comprising:
 a) concentrating said target analyte in a detection chamber comprising:
  i) a first surface comprising:
   1) an array of detection electrodes each comprising a covalently attached capture ligand;
   2) at least a first electrophoresis electrode;
  ii) a second surface comprising at least a second electrophoresis electrode; and
  iii) at least one channel connecting said first surface and second surface;
 b) binding said target analyte to said capture ligand to form an assay complex, wherein said assay complex further comprises at least one electron transfer moiety (ETM); and
 c) detecting the presence of said ETM using said detection electrode.

18. A method according to claim 17 wherein said detection electrodes further comprise a self-assembled monolayer.

19. A method according to claim 17 wherein said detection chamber further comprises a substrate.

20. A method according to claim 19 wherein said substrate is a PC board.

21. A method according to claim 17 wherein said capture ligand is nucleic acid.

22. A method according to claim 17 wherein said assay complex comprises said target analyte, said capture ligand, and a label probe and wherein said label probe comprises said ETM.

23. A method according to claim 17 wherein said assay complex comprises said target analyte and said capture ligand and said target analyte comprises said ETM.

24. A method according to claim 17 wherein said ETM is a transition metal complex.

25. A method of detecting a target analyte in a sample comprising:
 a) concentrating said target analyte in a detection chamber comprising:
  i) a substrate comprising:
   1) a first surface comprising:
    A) an array of detection electrodes each comprising a covalently attached capture ligand;
   2) a second surface;
   3) at least one channel connecting said first surface and second surface; and
  ii) an absorbent material in contact with said second surface;
 b) binding said target analyte to said capture ligand to form an assay complex, wherein said assay complex further comprises at least one electron transfer moiety (ETM); and
 c) detecting the presence of said ETM using said detection electrode.

26. A method according to claim 25 wherein said detection electrodes further comprise a self-assembled monolayer.

27. A method according to claim 25 wherein said substrate is PC board.

28. A method according to claim 25 wherein said capture ligand is nucleic acid.

29. A method according to claim 25 wherein said assay complex comprises said target analyte, said capture ligand, and a label probe and wherein said label probe comprises said ETM.

30. A method according to claim 25 wherein said assay complex comprises said target analyte and said capture ligand and said target analyte comprises said ETM.

31. A method according to claim 25 wherein said ETM is a transition metal complex.

32. The method according to claim 25 wherein said detection chamber further comprises a size exclusion partition at either end of said at least one channel.

* * * * *